(12) United States Patent
Babu et al.

(10) Patent No.: US 6,653,340 B1
(45) Date of Patent: Nov. 25, 2003

(54) COMPOUNDS USEFUL IN THE COMPLEMENT, COAGULAT AND KALLIKREIN PATHWAYS AND METHOD FOR THEIR PREPARATION

(75) Inventors: Yarlagadda S. Babu, Birmingham, AL (US); J. Claude Bennett, Birmingham, AL (US); Shri Niwas, Birmingham, AL (US); R. Scott Rowland, Hoover, AL (US)

(73) Assignee: BioCryst Pharmaceuticals, Inc., Birmingham, AL (US)

( * ) Notice: Subject to any disclaimer, the term of this patent is extended or adjusted under 35 U.S.C. 154(b) by 0 days.

(21) Appl. No.: 09/647,154

(22) PCT Filed: Jun. 3, 1998

(86) PCT No.: PCT/US98/11255

§ 371 (c)(1),
(2), (4) Date: Sep. 27, 2000

(87) PCT Pub. No.: WO98/55471

PCT Pub. Date: Dec. 10, 1998

Related U.S. Application Data

(60) Provisional application No. 60/079,669, filed on Mar. 27, 1998, and provisional application No. 60/048,122, filed on Jun. 3, 1997.

(51) Int. Cl.[7] .................. A61K 31/343; A61K 31/381; C07D 307/78; C07D 333/52
(52) U.S. Cl. .................. 514/443; 514/444; 514/469; 549/51; 549/467; 549/470
(58) Field of Search ................. 514/443, 444, 514/469; 549/51, 60, 467, 470

(56) References Cited

U.S. PATENT DOCUMENTS 4,046,770 A  *  9/1977  Paget et al.
4,454,338 A     6/1984  Fujii et al. ............... 560/34
4,490,388 A    12/1984  Fujii et al. ............... 424/278
4,596,822 A     6/1986  Powers et al. ............ 514/459
5,281,721 A     1/1994  Powers et al. ............ 549/23

FOREIGN PATENT DOCUMENTS

EP       0798295       10/1997
JP      61286361       12/1986
JP      10101556        4/1998

OTHER PUBLICATIONS

Aoyama, et al., Synthesis and Structure–Activity Study of Protease Inhibitors. IV.[1] Amidinonaphthols and Related Acyl Derivatives[2]), Chem. Pharm. Bull. XP–002110067, vol. 33(4) pp. 1458–1471 (1985).
Iwanowicz, et al., Derivatives of 5–Amidine Indole As Inhibitors of Thrombin Catalytic Activity, Pergamon, Bioorganic & Medicinal Chemistry Letters. vol. 6, No. 12 pp. 1339–1344, (1996).

* cited by examiner

Primary Examiner—T. A. Solola
(74) Attorney, Agent, or Firm—Connolly Bove Lodge & Hutz LLP

(57) ABSTRACT

The present invention is concerned with new compounds, and particularly those having a fused bicyclic ring substituted with an amidine moiety. These compounds are each potent inhibitors of Factor D of the alternate pathway of complement, C1s of the classical pathway of complement, Factors Xa, XIIa, VIIa and thrombin of the coagulation pathway, plasmin in the fibrinolytic pathway, and kallikrein and high molecular weight kininogen in the inflammatory pathways. These proteases, which have serine in their active site, are called serine proteases and they are pivotal to most of the processes of inflammation and coagulation. In fact, these various systems are interactive with one another and it is difficult to activate one pathway without it influencing the others.

19 Claims, No Drawings

COMPOUNDS USEFUL IN THE COMPLEMENT, COAGULAT AND KALLIKREIN PATHWAYS AND METHOD FOR THEIR PREPARATION

DESCRIPTION

This Appn. is a 371 of PCT/US98/11255 filed Jun. 3, 1998 which claims the benefit of Prov. Applns. 60/079,669, filed Mar. 27, 1998 and 60/048,122, filed Jun. 3, 1997.

TECHNICAL FIELD

The present invention is concerned with new compounds, and particularly those having a fused bicyclic ring substituted with an amidine moiety. These compounds are each potent inhibitors of Factor D of the alternate pathway of complement, C1s of the classical pathway of complement, Factors Xa, XIIa, VIIa and thrombin of the coagulation pathway, plasmin in the fibrinolytic pathway, and kallikrein and high molecular weight kininogen in the inflammatory pathways. These proteases, which have serine in their active site, are called serine proteases and they are pivotal to most of the processes of inflammation and coagulation. In fact, these various systems are interactive with one another and it is difficult to activate one pathway without it influencing the others (see Diagram 1).

BACKGROUND OF INVENTION

Early in this century, it was noted that antibodies were not able to lyse bacteria by themselves. Factors were identified in serum which were required for the lysis of bacteria by antibodies. In 1989 Ehrlich and Morgenroth proposed the term "complements" for these factors because they complemented the activity of antibodies.

For many years cytolysis was the only known function of complement. During the past twenty five years, data in animals, including man, have identified the considerable biological potential of the complement system. The complement system functions as a "cascade." Namely, once an activator of the system converts a zymogen to an active enzyme, the activated enzyme then activates one or more proteins at the next stage, which in turn activates other zymogens. This can lead to profound biological effects, if the system is not controlled. Normally, well-defined regulatory (inhibitory) mechanisms are in place to regulate complement activation. However, in a host of pathophysiological conditions, inappropriate activation of the complement system occurs, and cell damage and cytolysis occur in major organ systems. Inappropriate complement activation has been identified in preclinical and clinical models of a host of inflammatory diseases, including autoimmune diseases such as inflammatory arthritis, cerebral and cardiac ischemic insult, and adult respiratory distress syndrome, as a major pathophysiological pathway.

The complement system is composed of 20 plasma proteins that interact in a cascading series of enzymatic activations and feedback loops and provides an important effector mechanism for the humoral immune system. Activation of the complement system leads to induction of the inflammatory process, stimulation of phagocytosis, chemotaxis of white blood cells, release of inflammatory mediators from mast cells, increasing blood vessel permeability and ultimately the lysis and cell death of cancer cells, bacteria, and viral-infected cells and neutralization of viruses.

Complement proteins are produced by most cells in the body on a continual basis, and circulate through the blood in a non-activated form. Activation can be initiated by two pathways: the "classical" pathway and the "alternative" pathway. While both pathways end up with activation of the key component C3, each pathway plays a distinctive role in host defense. The components of each pathway participate in a cascade of limited proteolysis reactions, cleaving the inactive form of the next component into a minor fragment (which itself may have biological properties) and a major fragment that goes on to participate in the next reaction. The major fragments of the final five components form a "membrane attachment complex" (MAC) that lyses cell membranes.

The complement system has profound biological effects other than cell lysis. Most immune system effector cells have surface receptors for complement fragments. The complement fragments C3a, C4a and C5a induce inflammation and smooth muscle contraction and vasodilation. The binding of C3a, C4a or C5a to receptors on mast cells and basophils promotes the secretion of histamine and other mediators of inflammation. C5a also induces production of leukotrienes and affects neutrophils and monocytes in a variety of ways: increases adherence to endothelial cells, causes these cells to migrate toward the source of C5a, increases oxygen consumption and generation of free radicals and induces secretion of glycolytic and proteolytic enzymes. C5a also induces production of IL-1 by macrophages. C3a induces the release of granulocytes from bone marrow, leading to leukocytosis.

C3b and C4b act as opsonins, coating invading bacteria, parasites or other cells at the site of complement activation. This coating provides a recognition signal for phagocytic cells which then bind to and engulf the invading cells. Neutrophils, monocytes and eosinophils all have C3b receptors.

There are two mechanisms principally responsible for the inflammatory response and tissue destruction in autoimmune disease. In the first mechanisms, circulating autoantibodies bind to tissues carrying the antigen. The antigen-antibody complex on the tissue surface then triggers the classical pathway of complement and activates immune system cells that have Fc receptors. This in turn leads to cell lysis.

A second mechanism involves circulating immune complexes in the blood or intracellular fluids. The immune complexes are deposited in the kidneys, lungs, blood vessels and joints where they activate the complement cascade. Complement activation then leads to tissue destruction. This mechanism account for many of the serious complications of rheumatoid arthritis, systemic lupus, myasthenia gravis and autoimmune hemolytic anemia. In these diseases, immune complexes are continually being deposited and complement destruction of tissue is chronic. When the complexes deposit in joints, inflammation results and when they deposit in the kidney glomeruli complement activation destroys renal function.

Complement Factor D is a crucial enzyme in the alternative pathway of complement (see Volanakis, J. E., The complement system, In Clinical Rheumatology; Boll, G.; Koopman, W., Eds., W. B. Saunders: New York, 1986, pp. 21–27 and Volanakis, J. E., Narayana, S. V. L. Complement Factor D, a novel serine protease, Protein Sci. 1996, 5, p.553–564). Complement Factor D is essential for the formation and function of the C3- and C5-convertase of the alternative pathway of complement. Factor D is an enzyme necessary for the cleavage of C3b -bound factor B. It is a single polypeptide chain serine proteinase of Mr, 24,000. Human Factor D isolated from serum of normal individuals or from urine of patients with Fanconi's syndrome exhibits esterolytic activity against peptide thioester substrates.

The low esterolytic activity of purified Factor D is compatible with the apparent absence of a structural zymogen for the enzyme in blood. That "native" factor D in blood is in enzymatically active form was demonstrated by Lesavre and Muller-Eberhard, Mechanism of Action of Factor D of the Alternate Complement Pathway, *J. Exp. Med.*, 148:1498–1509, 1978. They showed that distribution of Factor D hemolytic activity always overlapped that of antigenically measured Factor D protein when plasma or serum were subjected to various separation procedures. In addition, it has been shown that Factor D in serum can be inactivated by diisopropyl fluorophosphate and also by a series of serine proteinase inhibitors derived from isocoumarin. Inhibition of Factor D by these inhibitors results in inhibition of the alternative pathway indicating that no other proteinase can substitute for Factor D. Factor D was also shown to be synthesized and secreted in hemolytically active form by U937 cells, human blood-derived macrophages and HepG2 cells.

The serum concentration of Factor D, 1.8±0.4 ug/mL is the lowest of any complement protein. Studies on patients with renal insufficiency and in vivo microperfusion experiments using rat kidneys have indicated that the low concentration of Factor D is maintained by an extremely rapid catabolic rate. Due to its small size, Factor D is filtered through the glomerular membrane and is catabolized by the proximal renal tubules. Low serum levels of the enzyme may contribute to the regulation of its activity. In fact, Factor D has been shown to be the limiting enzyme in the activation sequence of the alternative pathway.

Factor D belongs to the serine protease family of enzymes. Some of the other members of this family include trypsin, thrombin, factor Xa, factor XIIa, plasmin, kallilcrein and elastase. Factor D has extensive sequence and structural homology with these enzymes. In spite of the similarities, most of the general serine protease inhibitors do not inhibit Factor D.

There are suggestions of certain amidino compounds being serine protease inhibitors (see U.S. Pat. No. 4,454,338 to Fujii et al; U.S. Pat. No. 4,490,388 to Fujii et al. and U.S. Pat. No. 4,634,783 to Fujii et al.; French Patent No. 2500826 to Fujii et al.; Yaegashi et al., Synthesis and structure-activity of protease inhibitors. III. Amidinophenols and their benzoyl esters. *Chem. Phamr. Bull.*, 1984, Volume 32 (11), pp.4466–4476; and Aoyama et al., Synthesis and structure-activity study of protease inhibitors. IV. Amidinonaphthols and related acyl derivatives. *Chem. Pharm. Bull.* 1985, Volume 33, pp. 1458–1471).

However, although some of these compounds have weak activity against Factor D, none are known to exhibit a strong inhibiting action against Factor D, and are not useful in suppressing alternate pathway activity. However, a potent inhibitor of Factor D would modulate the activation of the alternative pathway of the complement system.

It would therefore be desirable to identify serine protease inhibitors that are not only potent against enzymes in the coagulation, kinin and classical complement pathways, but also potent against Factor D of the alternate complement pathway. Although there have been various efforts to pharmacologically manipulate complement activation, to date there are no potent, useful inhibitors of Factor D reported.

The natural serine protease inhibitor, aprotinin, is currently in use in cardiovascular bypass graft surgery and its effectiveness in inhibiting plasmin has resulted in dramatic reduction in the need for transfusion. Such reported reductions have ranged between 35 and 90%. A synthetic serine protease inhibitor, nafamostat, has been shown to have similar good effect on plasmin in reducing transfusion requirements in patients having primary surgery in conjunction with heparin therapy as, for example, in cardiac bypass grafting. Several excellent inhibitors for thrombin, also a serine protease, have been developed to act as a specific inhibitor in the coagulation process. A recent one, novastan, is particularly useful as a replacement for heparin in surgery when patients have heparin-induced thrombocytopenia and other medical complications.

For many years, a search has been under way for the appropriate compound or "cocktail" of compounds, that could act during cardiopulmonary bypass as 1) an anticoagulant with the potency of heparin, 2) as inhibitor of the complement pathway, 3) an inhibitor of the kallikrein pathways, and 4) to inhibit plasmin and therefore prevent fibrinolysis of clots in microvessels. These processes would decrease organ injury due to blood activation on contact with the foreign surfaces of the pump oxygenator system.

Since these pathways are linked and interwined, it is clear that clinical conditions that are involved in their general activation, such as cardiopulmonary bypass systems, hemodialysis, hemofiltration, acute respiratory distress syndrome, septic shock, and disseminated intravascular coagulation will have many of the key serine proteases activated, which in turn perpetuates the further activation of the interlocking coagulation and inflammatory systems. In addition, diseases that are primarily mediated through the complement system potentially could be treated is acutely with an inhibitor of the classic and/or alternative pathways. These would include hereditary angio-edema and all immune complex diseases, such as lupus nephritis and many of the most difficult to treat vasculopathies and autoimmune diseases. Since serine proteases are active in several steps in the coagulation pathway, appropriate inhibitors should be highly-effective short-term anticoagulants. Because of an effect on the inflammatory pathways, prevention of reperfusion injury and perhaps acute tissue injury, such as in myocardial infarction, might be effectively treated in the acute stage by serine protease inhibitors.

SUMMARY OF THE INVENTION

The present invention provides novel compounds that possess the ability to inhibit the various pathways discussed above in the sub-micromolar range, some at an $IC_{50}$ level of one nanomolar. This broad spectrum of inhibition of plasma serine proteases by compounds of the present invention is shown in the Table of the biological results disclosed elsewhere in this application.

The concept of "blood anesthesia" has been introduced by cardiovascular surgeons working in the field of cardiopulmonary bypass. This term is applied to the use of combinations of compounds such as heparin, aprotinin, salicylates, persantin, etc. that could inhibit the coagulation components at several levels. The unexpected novelty of the compounds of the present invention, however, is that a single compound, highly specific for serine proteases, can act at multiple sites and singularly induce "blood anesthesia." Thus, in this invention, novel compounds and especially amidine compounds are disclosed, each of which have potency in all of these interrelated pathways, and therefore form an ideal basis for acute therapy.

The concept of a single compound able to affect so many sites in the coagulation, complement, fibronilytic and inflammatory response systems is unique. No one has previously published that a compound which inhibits a broad spectrum of serine proteases could be useful. All other previous work has attempted to find a specific inhibitor of one enzyme. Nevertheless, Gorman, III, J. H.; Edmunds, Jr., L. H. Blood anesthesia for cardiopulmonary bypass. *J. Card. Surg.* 1995, 10, 270–279; and Royston, D. Preventing the inflammatory response to open-heart surgery: The role of aprotinin and other protease inhibitors. *Int. J. Cardiol.* 1996, 53 (*suppl.*), S11–S37 point out that a compound which could prevent all these blood proteases from being released would be clinically useful.

| Clinical Situations Potentially Treatable by Serine Protease Inhibitors | | |
|---|---|---|
| Complement-Related | Anticoagulation | Anticoagulation and Inflammation |
| Acute Serum Sickness | Surgery in HIT patients | CPB |
| Hereditary angioedema | Hemodialysis | ARDS |
| Immune Complex Diseases | Hemofiltration | Septic Shock |
| SLE - nephritis | | DIC |
| Vasculitis | | Referfusion injury |
| Hemolytic Anemia | | Myocardial Infraction |
| ITP | | Cerebrovascular Hemorrhage |
| Related Inflammatory Diseases | | |
| Autoimmune Disease of All Organs | | |
| Xenotransplantation | | |

The compounds of the present invention contain four fragments, designated as L, E, R and Q, which are joined in a linear fashion as illustrated

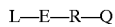

wherein:
Fragment L represents a hydrophobic group such as a 5-membered unsaturated ring, 6-membered unsaturated ring, alkene, saturated 3–7 membered ring;
Fragment E represents carbonyl derivative that in the presence of L, R and Q becomes an activated serine trap;
Fragment R represents a hydrophobic, aromatic ring system such as a 6-membered ring, fused 5–6 membered ring, or fused 6—6 membered ring; and
Fragment Q represents a basic group. The present invention is also concerned with pharmaceutically acceptable acid addition salts of the above amidine compound.

Another aspect of the present invention is concerned with preparing the above-disclosed compounds. The process includes reacting a carboxylic acid with a substituted carbodiimide to produce a mixed anhydride. The mixed anhydride is then reacted with a phenolic compound or acid salt thereof in a base to provide the desired compound.

The compounds of the present invention can also be prepared by reacting an acid halide with a phenolic compound or acid salt thereof which is suspended or dissolved in an organic solvent.

Other coupling methods can be employed to produce the amidine compounds of the present invention.

Still other objects and advantages of the present invention will become readily apparent by those skilled in the art from the following detailed description wherein it is shown and described only the preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BEST AND VARIOUS MODES FOR CARRYING OUT INVENTION

The novel compounds of the present invention contain four fragments, designated as L, E, R and Q, which are joined in a linear fashion as illustrated.

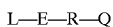

Fragment L represents a hydrophobic group such as a 5-membered unsaturated ring, 6-membered unsaturated ring, alkene, or saturated 3–7 membered rings. Examples of such are listed in Tables 1 and 1a and designated by numbers. These ring moieties can be hydrocarbon rings or heterocyclic rings containing one or more N, O and/or S atoms in the ring and more typically 1–3 heterocyclic atoms.

A represents H, straight or branched lower alkyl chain of 1–4 carbon atoms;

B represents H, $CF_3$, halogen such as Cl, I, Br, and F, $(CH_2)_mCO_2H$, $(CH_2)_mCH_2OH$, $(CH_2)_mNHA$, alkyl, alkoxy, aryl, or heterocyclic, and m=0–5.

Fragment E represents a carbonyl derivative that in the presence of L, R and Q becomes an activated serine trap. Tables 2 and 2a provide disclosure of exemplary E fragments, where each fragment is identified by a number.

Fragment R represents a hydrophobic, aromatic ring system such as a 6-membered ring, fused 5–6 membered ring, or fused 6—6 membered ring. Examples of such are disclosed in Table 3 and labeled with a number.

Fragment Q represents a basic group, examples of which are disclosed in Table 4 and designated by a number.

To facilitate a disclosure of and understanding of the present invention, a list of exemplary compounds can be constructed from the above named tables of fragments by exhaustive enumeration of all combinations of the fragments in accordance with the formula L—E—R—Q. A compound of such an enumeration is depicted by a number designating an L fragment from Table 1 or Table 1a. followed by a number for the E fragment from Table 2 or Table 2a, a number for the R fragment given in Table 3, and a number designating the Q fragment listed in Table 4 as in the following form:

For example 2-Amidino-6-benzofuranyl 2-furanylcarboxylate from Example 1 is represented by the depiction 46:1:14:2.

Specifically, the complete set of exemplary compounds consists of the union of the sets P and S wherein P is the exhaustive combinatorial enumeration of fragments from Tables 1, 2, 3, and 4 and S is the exhaustive combinatorial enumeration of fragments from Tables 1a, 2a, 3, and 4. Selected samples of the exhaustive combinatorial enumeration from sets P and S are given in Tables 5 and 5a, respectively.

Each fragment in the Tables 1, 1a, 2, 2a, 3, and 4 includes designation of the location of attachment to the adjacent fragment.
TABLE 1
Fragment L
1
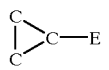
2
3
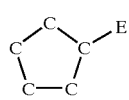
4
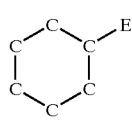
5
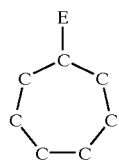
6
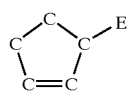
7
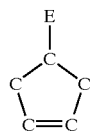
8
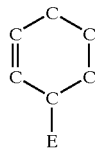
9
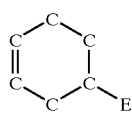
10
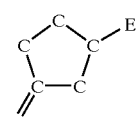
11
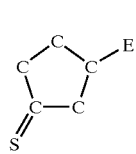
-continued
12
13
14
15
16
17
18
19
20
21

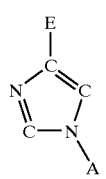
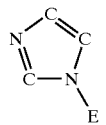
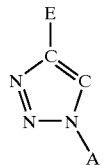
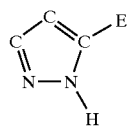
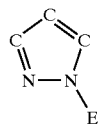
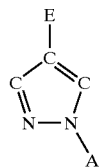
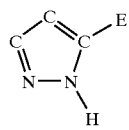
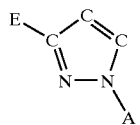
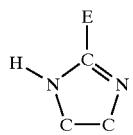
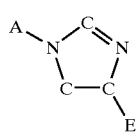
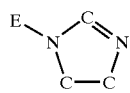
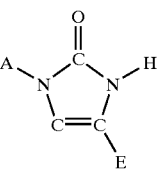
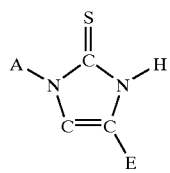
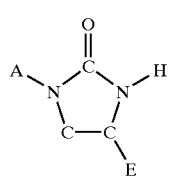
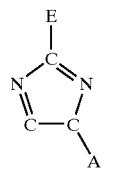
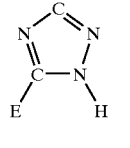
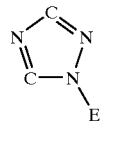
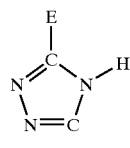
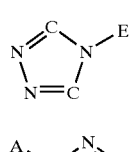
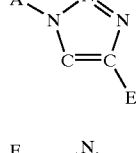
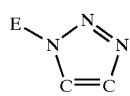

-continued
44
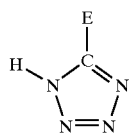
45
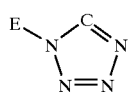
46
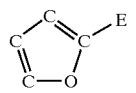
47
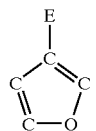
48
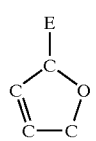
49
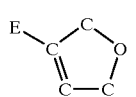
50
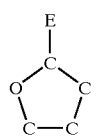
51
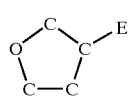
52
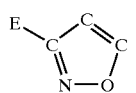
53
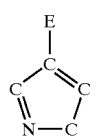
54
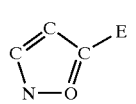
55
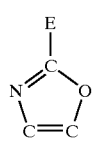
56
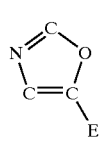
-continued
57
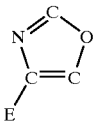
58
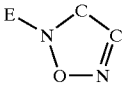
59
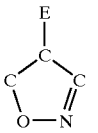
60
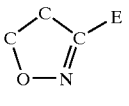
61
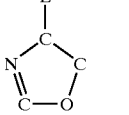
62
63
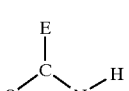
64
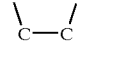
65
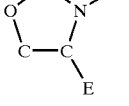
66
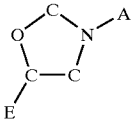
67
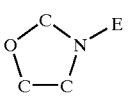
68
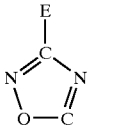
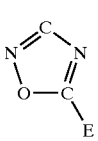

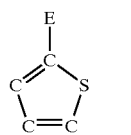
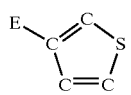
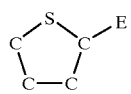
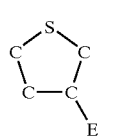
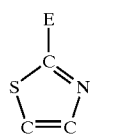
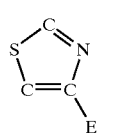
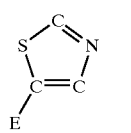
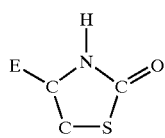
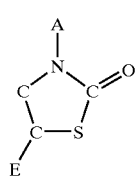
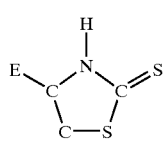
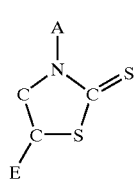
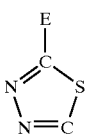
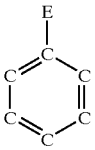
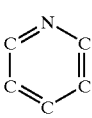
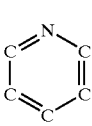
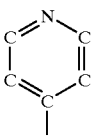
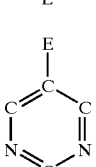
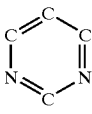
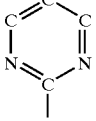

-continued
| | |
|---|---|
| 91 | 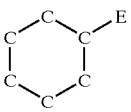 |
| 92 | 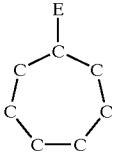 |
| 93 | 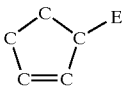 |
| 94 | 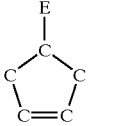 |
| 95 | 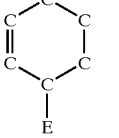 |
| 96 | 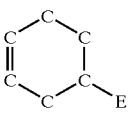 |
| 97 | 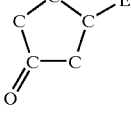 |
| 98 | 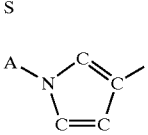 |
| 99 | 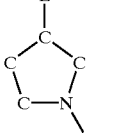 |
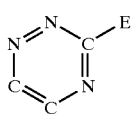
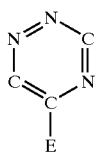
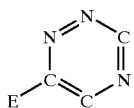
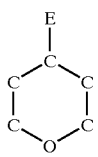
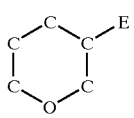
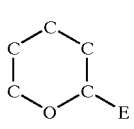
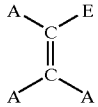
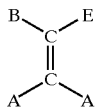
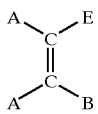
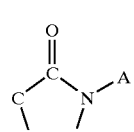
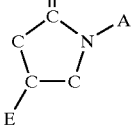
TABLE 1
Fragment L-restructured to use with Fragment E from Table 2a
| | |
|---|---|
| 1 |  |
| 2 | 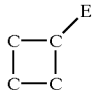 |
| 3 | 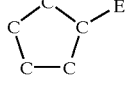 |

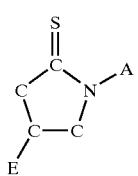
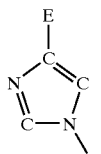
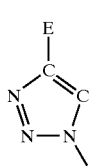
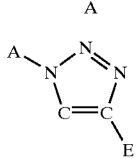
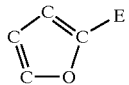
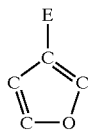
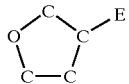
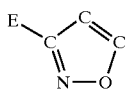
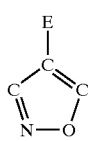
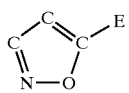
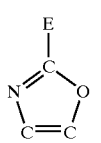
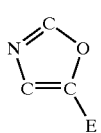
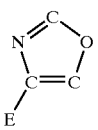
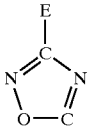
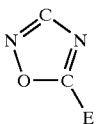
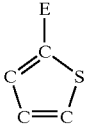
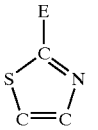
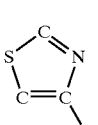
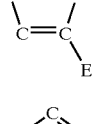
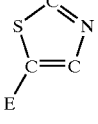
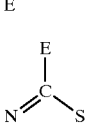
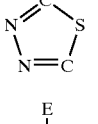
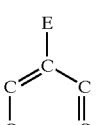
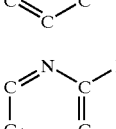
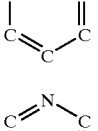
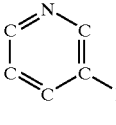
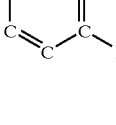

-continued
84 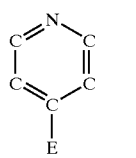
85 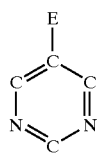
86 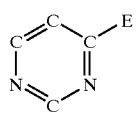
87 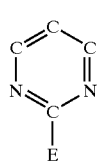
88 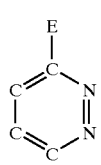
89 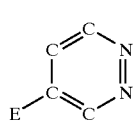
90 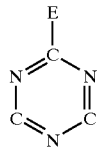
91 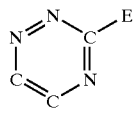
92 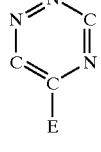
93 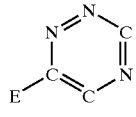
94 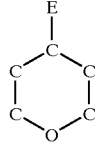
95 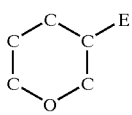
TABLE 2
Fragment E
1 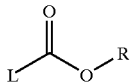
2 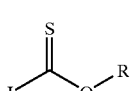
3 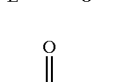
4 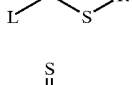
5 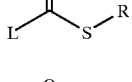
6 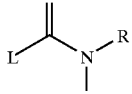
Fragment E-restructured to use with Fragment L from Table 1A
7 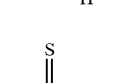
8 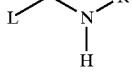
9 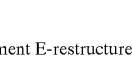
10 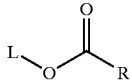
11 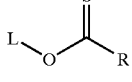

TABLE 3
Fragment R
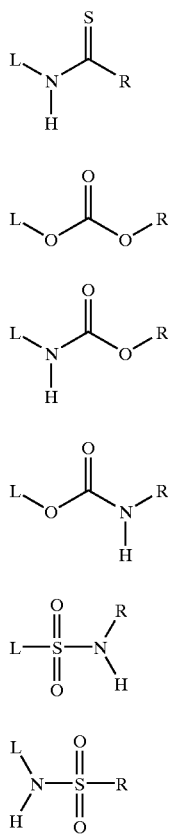
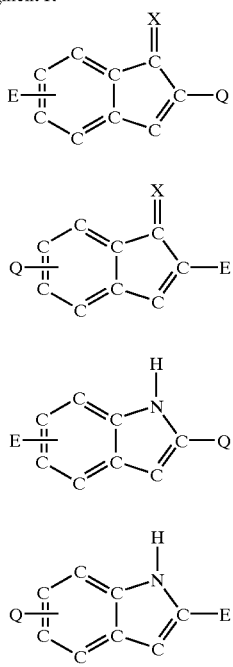
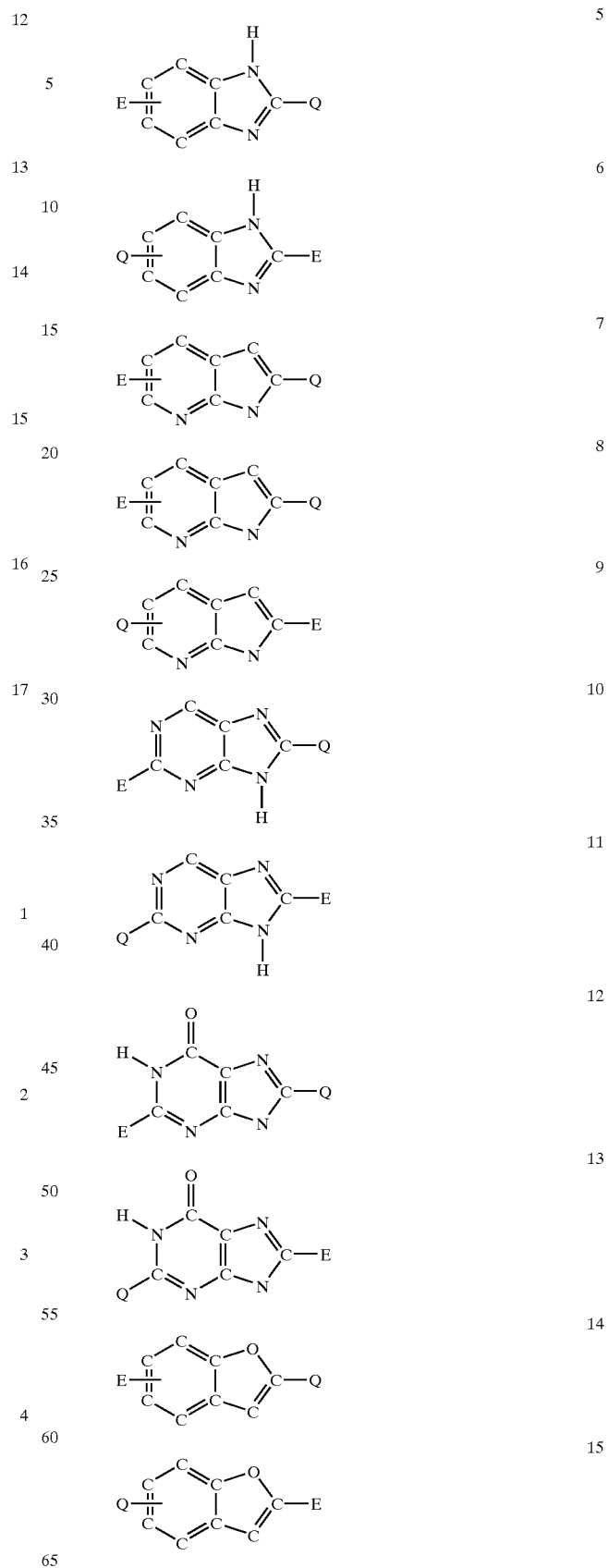

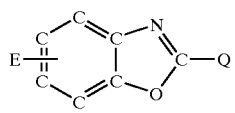
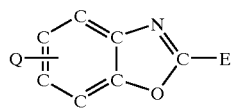
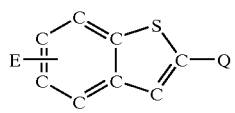
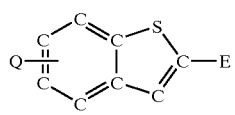
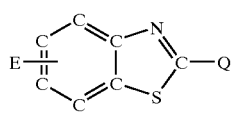
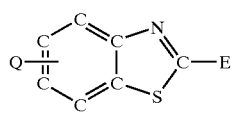
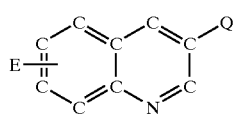
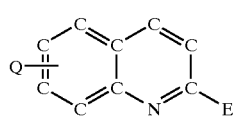
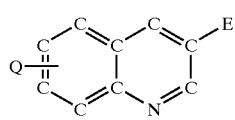
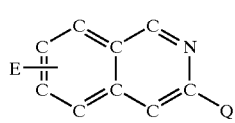
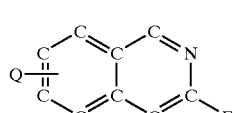
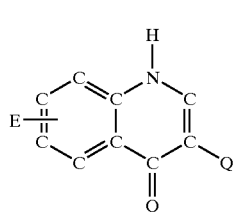
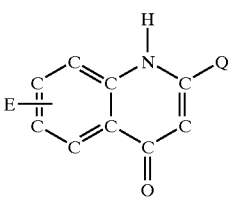
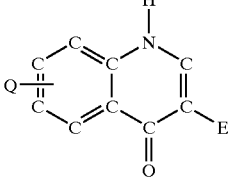
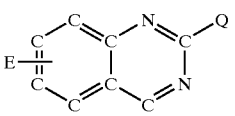
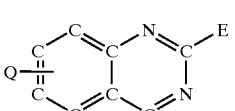
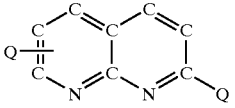
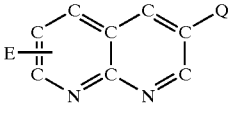
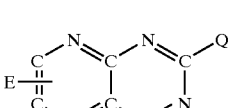
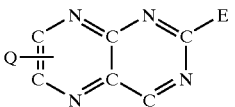
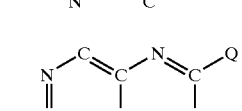
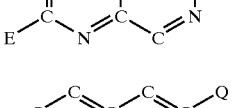
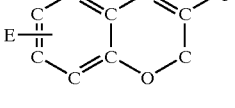
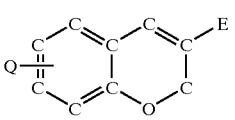

-continued
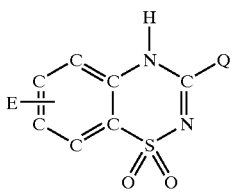
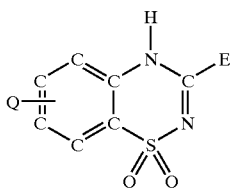
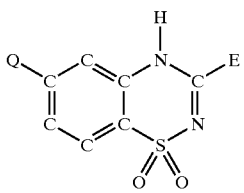
TABLE 4
Fragment Q
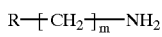
-continued
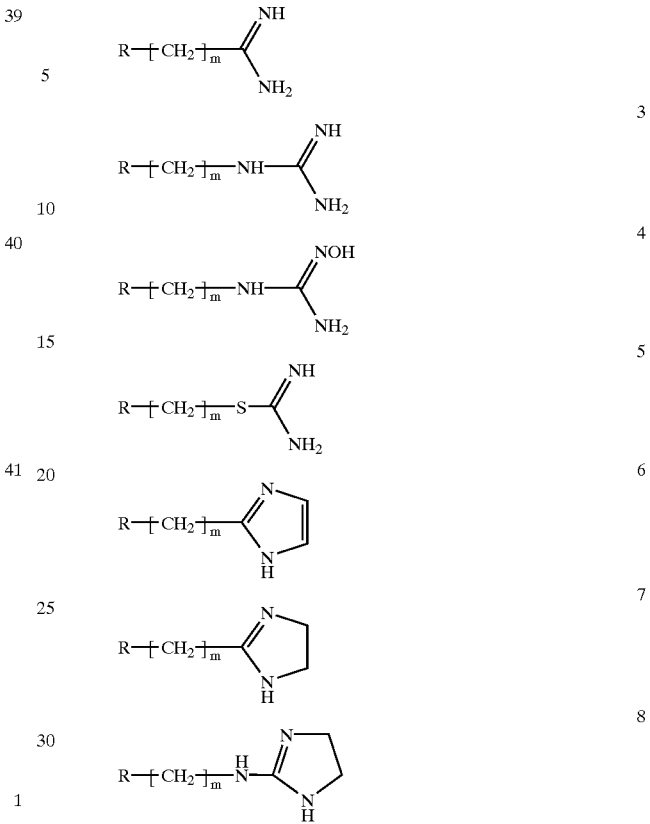
m = 0–5
TABLE 5
Exemplary Enumerated Compounds using Tables 1, 2, 3, and 4
| | | | | | | | |
|---|---|---|---|---|---|---|---|
| 1:2:1:3, | 1:2:1:6, | 1:2:3:3, | 1:2:3:5, | 1:2:3:6, | 1:2:3:7, | 1:2:6:7, | 1:2:6:8, |
| 1:2:7:2, | 1:2:7:3, | 1:2:7:5, | 1:2:7:8, | 1:2:9:3, | 1:2:9:4, | 1:2:9:6, | |
| 1:2:11:4, | 1:2:11:6, | 1:2:11:7, | 1:2:14:2, | 1:2:14:4, | 1:2:14:5, | 1:2:14:8, | |
| 1:2:16:6, | 1:2:16:7, | 1:2:16:8, | 1:2:17:2, | 1:2:17:5, | 1:2:17:8, | 1:2:21:4, | |
| 1:2:21:8, | 1:2:22:2, | 1:2:22:4, | 1:2:22:5, | 1:2:22:7, | 1:2:25:4, | 1:2:25:6, | |
| 1:2:25:7, | 1:2:26:2, | 1:2:26:8, | 1:2:29:3, | 1:2:29:7, | 1:2:30:3, | 1:2:30:4, | |
| 1:2:30:5, | 1:2:30:6, | 1:2:31:2, | 1:2:31:5, | 1:2:31:7, | 1:2:35:1, | 1:2:35:3, | |
| 1:2:35:4, | 1:2:35:5, | 1:2:39:2, | 1:2:39:8, | 1:2:41:1, | 1:2:41:4, | 1:2:41:6, | |
| 1:2:41:7, | 1:3:1:1, | 1:3:1:3, | 1:3:7:1, | 1:3:7:3, | 1:3:7:7, | 1:3:7:8, | |
| 1:3:10:2, | 1:3:10:6, | 1:3:19:2, | 1:3:19:5, | 1:3:19:6, | 1:3:19:8, | 1:3:27:1, | |
| 1:3:27:2, | 1:3:27:7, | 1:3:27:8, | 1:3:28:2, | 1:3:28:5, | 1:3:28:6, | 1:3:30:2, | |
| 1:3:30:4, | 1:3:30:8, | 1:3:32:2, | 1:3:32:5, | 1:3:32:7, | 1:3:33:5, | | |
| 1:3:33:6, | 1:3:33:8, | 1:3:37:3, | 1:3:37:4, | 1:3:39:3, | 1:3:39:7, | 1:3:39:8, | |
| 1:3:40:3, | 1:3:40:5, | 1:3:40:8, | 3:1:2:2, | 3:1:2:5, | 3:1:3:1, | 3:1:3:5, | |
| 3:1:3:8, | 3:1:8:2, | 3:1:8:6, | 3:1:8:8, | 3:1:11:1, | 3:1:11:6, | 3:1:11:8, | |
| 3:1:13:1, | 3:1:13:3, | 3:1:13:7, | 3:1:15:1, | 3:1:15:2, | 3:1:15:4, | 3:1:15:8, | |
| 3:1:25:1, | 3:1:25:3, | 3:1:25:5, | 3:1:28:1, | 3:1:28:2, | 3:1:28:3, | 3:1:28:5, | |
| 3:1:36:1, | 3:1:36:4, | 3:1:36:5, | 3:1:36:7, | 3:1:37:2, | 3:1:37:5, | 3:1:37:8, | |
| 3:2:6:1, | 3:2:6:2, | 3:2:6:3, | 3:2:6:8, | 3:2:7:1, | 3:2:7:6, | 3:2:7:7, | 3:2:9:2, |
| 3:2:9:4, | 3:2:11:2, | 3:2:11:3, | 3:2:11:8, | 3:2:16:2, | 3:2:16:3, | 3:2:16:5, | |
| 3:2:16:4, | 3:2:16:8, | 3:2:22:1, | 3:2:22:6, | 3:2:22:8, | 3:2:24:1, | 3:2:24:4, | |
| 3:2:24:5, | 3:2:25:4, | 3:2:25:5, | 3:2:25:6, | 3:2:25:7, | 3:2:32:1, | 3:2:32:2, | |
| 3:2:32:3, | 3:2:32:4, | 3:2:33:1, | 3:2:33:2, | 3:2:33:5, | 3:2:33:6, | 3:3:3:1, | |
| 3:3:3:3, | 3:3:3:5, | 3:3:3:6, | 3:3:14:1, | 3:3:14:4, | 3:3:14:5, | 3:3:14:8, | |
| 3:3:24:2, | 3:3:24:3, | 3:3:24:5, | 3:3:26:2, | 3:3:26:4, | 3:3:26:5, | 3:3:26:8, | |
| 3:3:29:1, | 3:3:29:5, | 3:3:29:6, | 3:3:31:1, | 3:3:31:2, | 3:3:31:4, | 3:3:31:7, | |
| 3:3:33:6, | 3:3:33:8, | 3:3:35:2, | 3:3:35:3, | 3:3:35:4, | 3:3:37:2, | 3:3:37:5, | |
| 3:4:1:1, | 3:4:1:7, | 3:4:1:8, | 3:4:3:2, | 3:4:3:3, | 3:4:3:4, | 3:4:3:7, | 3:4:4:1, |
| 3:4:4:7, | 3:4:5:4, | 3:4:5:5, | 3:4:5:6, | 3:4:15:1, | 3:4:15:5, | 3:4:17:1, | |
| 3:4:17:6, | 3:4:17:7, | 3:4:17:8, | 3:4:21:4, | 3:4:21:7, | 3:4:21:8, | 3:4:28:5, | |
| 3:4:28:7, | 3:4:28:8, | 3:4:29:1, | 3:4:29:4, | 3:4:31:3, | 3:4:31:4, | 3:4:31:6, | |

TABLE 5-continued

Exemplary Enumerated Compounds using Tables 1, 2, 3, and 4

| | | | | | | |
|---|---|---|---|---|---|---|
| 3:4:31:8, | 3:4:35:1, | 3:4:35:4, | 3:4:36:3, | 3:4:36:5, | 3:4:36:7, | 3:4:36:8, |
| 3:4:38:1, | 3:4:38:2, | 3:4:38:7, | 3:4:38:8, | 3:4:39:4, | 3:4:39:6, | 3:4:39:7, |
| 3:4:41:4, | 3:4:41:5, | 3:5:4:3, | 3:5:4:8, | 3:5:5:3, | 3:5:5:5, | 3:5:5:7, |
| 3:5:6:1, | 3:5:6:6, | 3:5:12:4, | 3:5:12:5, | 3:5:12:8, | 3:5:14:5, | 3:5:14:6, |
| 3:5:15:3, | 3:5:15:4, | 3:5:15:6, | 3:5:15:7, | 3:5:16:1, | 3:5:16:8, | 3:5:21:1, |
| 3:5:21:6, | 3:5:22:2, | 3:5:22:5, | 3:5:22:6, | 3:5:22:7, | 3:5:25:1, | 3:5:25:2, |
| 3:5:27:1, | 3:5:27:2, | 3:5:27:7, | 3:5:31:5, | 3:5:31:7, | 3:5:38:2, | 3:5:38:6, |
| 3:5:39:3, | 3:5:39:4, | 3:5:39:8, | 7:4:10:5, | 7:4:10:6, | 7:4:11:3, | 7:4:11:6, |
| 7:4:11:8, | 7:4:14:4, | 7:4:14:8, | 7:4:15:1, | 7:4:15:4, | 7:4:15:5, | 7:4:16:3, |
| 7:4:16:5, | 7:4:18:2, | 7:4:18:6, | 7:4:25:1, | 7:4:25:6, | 7:4:25:7, | 7:4:26:6, |
| 7:4:26:7, | 7:4:26:8, | 7:4:28:1, | 7:4:28:2, | 7:4:28:5, | 7:4:28:7, | 7:4:29:3, |
| 7:4:29:5, | 7:4:29:6, | 7:4:29:7, | 7:4:31:4, | 7:4:31:5, | 7:4:35:3, | 7:4:35:5, |
| 7:4:38:2, | 7:4:38:3, | 7:4:38:4, | 7:4:38:5, | 7:4:39:3, | 7:4:39:5, | 7:4:39:7, |
| 7:4:39:8, | 7:5:1:3, | 7:5:1:5, | 7:5:5:1, | 7:5:5:6, | 7:5:6:2, | 7:5:6:3, |
| 7:5:12:3, | 7:5:12:4, | 7:5:12:5, | 7:5:13:3, | 7:5:13:7, | 7:5:20:3, | 7:5:20:4, |
| 7:5:23:2, | 7:5:23:5, | 7:5:24:1, | 7:5:24:2, | 7:5:24:4, | 7:5:24:6, | 7:5:27:4, |
| 7:5:27:6, | 7:5:27:8, | 7:5:28:5, | 7:5:28:8, | 7:5:29:2, | 7:5:29:6, | 7:5:29:7, |
| 7:5:29:8, | 7:5:31:3, | 7:5:31:6, | 7:5:32:3, | 7:5:32:4, | 7:5:32:5, | 7:5:36:1, |
| 7:5:36:4, | 7:5:36:5, | 7:5:39:2, | 7:5:39:3, | 7:5:39:4, | 11:2:4:1, | 11:2:4:3, |
| 11:2:4:6, | 11:2:4:8, | 11:2:8:1, | 11:2:8:6, | 11:2:8:7, | 11:2:9:2, | 11:2:9:5, |
| 11:2:10:3, | 11:2:10:5, | 11:2:13:1, | 11:2:13:3, | 11:2:13:4, | 11:2:13:8, | |
| 11:2:17:1, | 11:2:17:4, | 11:2:17:8, | 11:2:21:1, | 11:2:21:4, | 11:2:21:6, | |
| 11:2:21:8, | 11:2:23:5, | 11:2:23:7, | 11:2:27:2, | 11:2:27:7, | 11:2:29:2, | |
| 11:2:29:7, | 11:2:30:2, | 11:2:30:4, | 11:2:30:5, | 11:2:34:2, | 11:2:34:4, | |
| 11:2:34:7, | 11:2:34:8, | 11:3:5:2, | 11:3:5:3, | 11:3:5:6, | 11:3:9:7, | 11:3:9:8, |
| 11:3:12:1, | 11:3:12:4, | 11:3:12:6, | 11:3:13:2, | 11:3:13:3, | 11:3:13:4, | |
| 11:3:13:8, | 11:3:14:1, | 11:3:14:2, | 11:3:14:4, | 11:3:14:7, | 11:3:19:1, | |
| 11:3:19:2, | 11:3:19:4, | 11:3:19:7, | 11:3:20:1, | 11:3:20:3, | 11:3:20:4, | |
| 11:3:20:7, | 11:3:21:3, | 11:3:21:6, | 11:3:22:1, | 11:3:22:4, | 11:3:22:6, | |
| 11:3:25:3, | 11:3:25:6, | 11:3:25:8, | 11:3:30:5, | 11:3:30:7, | 11:3:32:4, | |
| 11:3:32:6, | 11:3:32:7, | 11:3:32:8, | 11:3:33:2, | 11:3:33:3, | 11:3:33:6, | |
| 11:3:33:8, | 11:3:34:4, | 11:3:34:8, | 11:3:41:2, | 11:3:41:5, | 11:3:41:7, | |
| 11:4:1:1, | 11:4:1:7, | 11:4:2:2, | 11:4:2:6, | 11:4:2:8, | 11:4:3:5, | 11:4:3:7, |
| 11:4:4:5, | 11:4:4:6, | 11:4:4:7, | 11:4:6:5, | 11:4:6:7, | 11:4:13:2, | 11:4:13:5, |
| 11:4:13:6, | 11:4:15:2, | 11:4:15:4, | 11:4:15:7, | 11:4:15:8, | 11:4:16:1, | |
| 11:4:16:4, | 11:4:16:6, | 11:4:17:2, | 11:4:17:3, | 11:4:17:5, | 11:4:17:6, | |
| 11:4:18:1, | 11:4:18:5, | 11:4:18:6, | 11:4:18:8, | 11:4:19:1, | 11:4:19:3, | |
| 11:4:19:4, | 11:4:22:2, | 11:4:22:7, | 11:4:22:8, | 11:4:25:1, | 11:4:25:5, | |
| 11:4:27:1, | 11:4:27:5, | 11:4:27:6, | 11:4:27:7, | 11:4:29:4, | 11:4:29:7, | |
| 11:4:32:4, | 11:4:32:5, | 11:4:32:6, | 11:4:32:7, | 11:4:33:2, | 11:4:33:3, | |
| 11:4:33:5, | 11:4:33:7, | 11:4:34:1, | 11:4:34:6, | 11:4:34:8, | 11:4:38:3, | |
| 11:4:38:5, | 11:4:38:7, | 11:4:41:4, | 11:4:41:6, | 12:2:3:3, | 12:2:3:5, | |
| 12:2:5:1, | 12:2:5:2, | 12:2:5:6, | 12:2:5:7, | 12:2:7:2, | 12:2:7:4, | 12:2:8:1, |
| 12:2:8:2, | 12:2:8:5, | 12:2:8:8, | 12:2:11:5, | 12:2:11:7, | 12:2:11:8, | |
| 12:2:12:2, | 12:2:12:5, | 12:2:12:6, | 12:2:12:7, | 12:2:13:1, | 12:2:13:2, | |
| 12:2:13:4, | 12:2:13:6, | 12:2:15:2, | 12:2:15:4, | 12:2:15:6, | 12:2:16:1, | |
| 12:2:16:3, | 12:2:16:5, | 12:2:16:7, | 12:2:17:3, | 12:2:17:4, | 12:2:23:1, | |
| 12:2:23:2, | 12:2:23:4, | 12:2:23:6, | 12:2:25:1, | 12:2:25:3, | 12:2:25:6, | |
| 12:2:25:8, | 12:2:35:2, | 12:2:35:3, | 12:2:35:7, | 12:2:35:8, | 12:2:36:4, | |
| 12:2:36:5, | 12:2:36:6, | 12:2:38:2, | 12:2:38:6, | 12:2:39:1, | 12:2:39:2, | |
| 12:2:39:7, | 12:2:41:4, | 12:2:41:5, | 12:2:41:6, | 12:2:41:8, | 12:3:2:1, | |
| 12:3:2:3, | 12:3:2:6, | 12:3:2:8, | 12:3:9:1, | 12:3:9:6, | 12:3:9:7, | 12:3:9:8, |
| 12:3:16:3, | 12:3:16:4, | 12:3:16:6, | 12:3:16:7, | 12:3:17:2, | 12:3:17:3, | |
| 12:3:17:6, | 12:3:17:8, | 12:3:19:1, | 12:3:19:2, | 12:3:19:4, | 12:3:19:5, | |
| 12:3:21:3, | 12:3:21:4, | 12:3:21:7, | 12:3:23:3, | 12:3:23:4, | 12:3:23:7, | |
| 12:3:23:8, | 12:3:29:1, | 12:3:29:2, | 12:3:30:1, | 12:3:30:2, | 12:3:30:3, | |
| 12:3:30:8, | 12:3:31:1, | 12:3:31:2, | 12:3:31:4, | 12:3:33:3, | 12:3:33:6, | |
| 12:4:2:2, | 12:4:2:3, | 12:4:2:4, | 12:4:5:1, | 12:4:5:4, | 12:4:5:5, | 12:4:5:6, |
| 12:4:9:2, | 12:4:9:3, | 12:4:9:5, | 12:4:9:6, | 12:4:10:1, | 12:4:10:7, | |
| 12:4:11:1, | 12:4:11:5, | 12:4:11:7, | 12:4:13:2, | 12:4:13:5, | 12:4:14:4, | |
| 12:4:14:6, | 12:4:14:8, | 12:4:17:5, | 12:4:17:6, | 12:4:17:7, | 12:4:19:6, | |
| 12:4:19:7, | 12:4:22:2, | 12:4:22:5, | 12:4:24:1, | 12:4:24:7, | 12:4:25:2, | |
| 12:4:25:5, | 12:4:25:8, | 12:4:26:2, | 12:4:26:5, | 12:4:26:8, | 12:4:27:2, | |
| 12:4:27:4, | 12:4:27:6, | 12:4:27:7, | 12:4:31:3, | 12:4:31:7, | 12:4:34:2, | |
| 12:4:34:3, | 12:4:34:8, | 12:4:39:3, | 12:4:39:7, | 12:4:41:3, | 12:4:41:4, | |
| 12:4:41:5, | 12:4:41:7, | 12:5:2:2, | 12:5:2:3, | 12:5:2:7, | 12:5:3:1, | 12:5:3:4, |
| 12:5:3:6, | 12:5:4:1, | 12:5:4:2, | 12:5:4:5, | 12:5:7:1, | 12:5:7:2, | 12:5:7:3, |
| 12:5:7:5, | 12:5:8:1, | 12:5:8:5, | 12:5:8:8, | 12:5:9:1, | 12:5:9:2, | 12:5:9:5, |
| 12:5:15:3, | 12:5:15:6, | 12:5:17:1, | 12:5:17:7, | 12:5:19:3, | 12:5:19:6, | |
| 12:5:19:7, | 12:5:22:2, | 12:5:22:3, | 12:5:22:8, | 12:5:23:1, | 12:5:23:2, | |
| 12:5:23:3, | 12:5:23:8, | 12:5:27:2, | 12:5:27:5, | 12:5:28:1, | 12:5:28:3, | |
| 12:5:28:4, | 12:5:28:7, | 12:5:29:3, | 12:5:29:4, | 12:5:29:5, | 12:5:29:7, | |
| 12:5:31:3, | 12:5:31:5, | 12:5:31:7, | 12:5:31:8, | 12:5:32:1, | 12:5:32:2, | |
| 12:5:32:5, | 12:5:36:3, | 12:5:36:6, | 12:5:39:4, | 12:5:39:5, | 12:5:39:8, | |
| 12:5:41:1, | 12:5:41:5, | 12:5:41:7, | 12:6:2:1, | 12:6:2:4, | 12:6:2:6, | |
| 12:6:2:8, | 12:6:4:3, | 12:6:4:4, | 12:6:4:7, | 12:6:8:1, | 12:6:8:5, | 12:6:8:6, |
| 12:6:8:7, | 12:6:9:4, | 12:6:9:5, | 12:6:9:6, | 12:6:9:7, | 12:6:10:1, | 12:6:10:4, |

TABLE 5-continued

Exemplary Enumerated Compounds using Tables 1, 2, 3, and 4

12:6:10:6, 12:6:10:8, 12:6:11:2, 12:6:11:6, 12:6:13:1, 12:6:13:4,
12:6:13:6, 12:6:13:8, 12:6:14:2, 12:6:14:4, 12:6:14:7, 12:6:14:8,
12:6:18:2, 12:6:18:5, 12:6:18:6, 12:6:18:7, 12:6:22:2, 12:6:22:3,
12:6:22:4, 12:6:22:6, 12:6:23:4, 12:6:23:6, 12:6:23:8, 12:6:24:5,
12:6:24:8, 12:6:25:1, 12:6:25:3, 12:6:25:5, 12:6:25:8, 12:6:27:2,
12:6:27:4, 12:6:27:6, 12:6:27:7, 12:6:32:1, 12:6:32:8, 12:6:34:1,
12:6:34:2, 12:6:34:4, 12:6:37:1, 12:6:37:5, 12:6:37:8, 12:6:38:1,
12:6:38:3, 12:6:38:5, 12:6:38:7, 12:6:40:2, 12:6:40:4, 12:6:40:8,
25:1:1:1, 25:1:1:2, 25:1:1:4, 25:1:1:5, 25:1:8:1, 25:1:8:2, 25:1:8:3,
25:1:8:4, 25:1:9:1, 25:1:9:2, 25:1:9:5, 25:1:9:6, 25:1:11:4, 25:1:11:6,
25:1:12:2, 25:1:12:3, 25:1:12:8, 25:1:14:1, 25:1:14:2, 25:1:14:6,
25:1:14:8, 25:1:16:4, 25:1:16:5, 25:1:16:7, 25:1:19:1, 25:1:19:2,
25:1:19:3, 25:1:19:7, 25:1:22:1, 25:1:22:2, 25:1:22:6, 25:1:23:3,
25:1:23:6, 25:1:24:3, 25:1:24:4, 25:1:32:3, 25:1:32:5, 25:1:33:1,
25:1:33:6, 25:1:34:2, 25:1:34:3, 25:1:34:5, 25:1:34:8, 25:1:39:2,
25:1:39:3, 25:1:39:5, 25:1:39:8, 25:2:3:1, 25:2:3:3, 25:2:3:4,
25:2:3:5, 25:2:4:3, 25:2:4:5, 25:2:4:8, 25:2:5:2, 25:2:5:3, 25:2:5:6,
25:2:5:8, 25:2:19:1, 25:2:19:3, 25:2:19:6, 25:2:21:5, 25:2:21:6,
25:2:21:8, 25:2:27:1, 25:2:27:5, 25:2:27:7, 25:2:27:8, 25:2:29:2,
25:2:29:3, 25:2:29:4, 25:2:29:8, 25:2:34:2, 25:2:34:4, 25:2:39:3,
25:2:39:4, 25:2:39:6, 25:2:39:8, 25:2:41:2, 25:2:41:3, 25:2:41:4,
25:2:41:8, 25:4:6:3, 25:4:6:4, 25:4:6:5, 25:4:6:6, 25:4:12:1,
25:4:12:5, 25:4:18:2, 25:4:18:4, 25:4:20:1, 25:4:20:2, 25:4:20:4,
25:4:20:5, 25:4:26:2, 25:4:26:3, 25:4:26:6, 25:4:26:8, 25:4:31:1,
25:4:31:4, 25:4:31:8, 25:4:33:1, 25:4:33:3, 25:4:33:6, 25:4:33:8,
25:4:35:1, 25:4:35:6, 25:4:35:7, 25:4:35:8, 25:4:40:1, 25:4:40:5,
25:4:40:7, 25:6:5:3, 25:6:5:4, 25:6:5:8, 25:6:7:3, 25:6:7:6, 25:6:17:1,
25:6:17:3, 25:6:17:5, 25:6:17:7, 25:6:25:4, 25:6:25:5, 25:6:25:6,
25:6:25:7, 25:6:26:1, 25:6:26:3, 25:6:28:1, 25:6:28:5, 25:6:28:6,
25:6:28:8, 25:6:29:2, 25:6:29:4, 25:6:29:7, 25:6:31:1, 25:6:31:5,
25:6:31:6, 25:6:32:4, 25:6:32:5, 25:6:32:6, 25:6:32:8, 25:6:35:3,
25:6:35:5, 25:6:35:6, 25:6:35:8, 32:1:2:4, 32:1:2:5, 32:1:2:7,
32:1:5:1, 32:1:5:3, 32:1:5:4, 32:1:6:1, 32:1:6:4, 32:1:6:6, 32:1:8:1,
32:1:8:6, 32:1:8:7, 32:1:8:8, 32:1:9:3, 32:1:9:6, 32:1:9:7, 32:1:10:2,
32:1:10:3, 32:1:10:5, 32:1:10:7, 32:1:23:1, 32:1:23:4, 32:1:23:6,
32:1:24:3, 32:1:24:8, 32:1:26:1, 32:1:26:2, 32:1:26:5, 32:1:26:8,
32:1:30:1, 32:1:30:5, 32:1:30:8, 32:1:32:4, 32:1:32:5, 32:1:35:1,
32:1:35:3, 32:1:35:8, 32:3:3:4, 32:3:3:7, 32:3:3:8, 32:3:5:2, 32:3:5:6,
32:3:5:7, 32:3:5:8, 32:3:8:1, 32:3:8:5, 32:3:8:7, 32:3:9:2, 32:3:9:8,
32:3:11:2, 32:3:11:3, 32:3:11:7, 32:3:13:5, 32:3:13:6, 32:3:14:2,
32:3:14:7, 32:3:15:1, 32:3:15:3, 32:3:15:4, 32:3:16:5, 32:3:16:8,
32:3:19:5, 32:3:19:6, 32:3:19:8, 32:3:20:3, 32:3:20:4, 32:3:20:5,
32:3:20:6, 32:3:23:1, 32:3:23:2, 32:3:23:4, 32:3:29:5, 32:3:29:7,
32:3:32:1, 32:3:32:3, 32:3:32:7, 32:3:35:4, 32:3:35:6, 32:3:36:1,
32:3:36:2, 32:3:36:3, 32:3:36:6, 32:3:38:2, 32:3:38:4, 32:3:38:7,
32:3:38:8, 32:3:40:4, 32:3:40:5, 32:3:41:1, 32:3:41:2, 32:3:41:4,
32:3:41:7, 32:6:1:6, 32:6:1:8, 32:6:2:5, 32:6:2:7, 32:6:2:8, 32:6:4:1,
32:6:4:4, 32:6:6:1, 32:6:6:6, 32:6:10:1, 32:6:10:5, 32:6:10:7,
32:6:11:3, 32:6:11:6, 32:6:11:7, 32:6:11:8, 32:6:12:2, 32:6:12:4,
32:6:12:6, 32:6:12:8, 32:6:13:1, 32:6:13:3, 32:6:13:5, 32:6:14:1,
32:6:14:7, 32:6:14:8, 32:6:15:5, 32:6:15:7, 32:6:15:8, 32:6:18:1,
32:6:18:4, 32:6:18:7, 32:6:20:5, 32:6:20:7, 32:6:20:8, 32:6:22:2,
32:6:22:5, 32:6:22:6, 32:6:22:8, 32:6:23:1, 32:6:23:4, 32:6:23:8,
32:6:24:1, 32:6:24:2, 32:6:24:4, 32:6:24:5, 32:6:30:1, 32:6:30:2,
32:6:30:7, 32:6:30:7, 32:6:32:3, 32:6:32:8, 32:6:37:1, 32:6:37:2,
32:6:37:7, 36:1:9:2, 36:1:9:4, 36:1:9:5, 36:1:9:6, 36:1:10:1,
36:1:10:6, 36:1:15:3, 36:1:15:5, 36:1:15:6, 36:1:15:8, 36:1:16:1,
36:1:16:4, 36:1:22:3, 36:1:22:4, 36:1:33:7, 36:1:33:8, 36:1:38:3,
36:1:38:6, 36:1:40:1, 36:1:40:3, 36:1:40:4, 36:1:40:7, 36:1:41:1,
36:1:41:2, 36:1:41:5, 36:1:41:7, 36:2:5:3, 36:2:5:5, 36:2:5:7,
36:2:5:8, 36:2:14:3, 36:2:14:5, 36:2:14:7, 36:2:14:8, 36:2:17:1,
36:2:17:7, 36:2:18:1, 36:2:18:4, 36:2:18:5, 36:2:18:7, 36:2:22:4,
36:2:22:7, 36:2:23:2, 36:2:23:5, 36:2:23:7, 36:2:23:8, 36:2:28:2,
36:2:28:3, 36:2:28:5, 36:2:28:6, 36:2:29:1, 36:2:29:2, 36:2:29:3,
36:2:29:8, 36:2:33:5, 36:2:33:6, 36:2:35:5, 36:2:35:7, 36:2:35:8,
36:2:37:2, 36:2:37:4, 36:2:37:6, 36:2:40:1, 36:2:40:3, 36:2:40:5,
36:2:40:7, 36:3:8:2, 36:3:8:5, 36:3:16:3, 36:3:16:4, 36:3:16:6,
36:3:16:8, 36:3:22:1, 36:3:22:2, 36:3:22:3, 36:3:22:5, 36:3:23:1,
36:3:23:3, 36:3:23:6, 36:3:32:5, 36:3:32:8, 36:3:33:3, 36:3:33:4,
36:3:33:8, 36:3:34:2, 36:3:34:5, 36:3:34:7, 36:3:38:2, 36:3:38:3,
36:3:38:6, 36:4:3:3, 36:4:3:4, 36:4:3:6, 36:4:3:8, 36:4:5:3, 36:4:5:5,
36:4:5:6, 36:4:11:2, 36:4:11:6, 36:4:16:2, 36:4:16:4, 36:4:16:6,
36:4:21:4, 36:4:21:8, 36:4:25:2, 36:4:25:6, 36:4:27:1, 36:4:27:2,
36:4:27:5, 36:4:28:6, 36:4:28:7, 36:4:33:2, 36:4:33:4, 36:4:33:7,
36:4:34:5, 36:4:34:7, 36:4:35:6, 36:4:35:7, 36:4:35:8, 36:4:39:1,
36:4:39:2, 36:4:39:6, 36:4:39:8, 36:4:41:4, 36:4:41:7, 36:4:41:8,
36:5:1:2, 36:5:1:3, 36:5:2:4, 36:5:2:6, 36:5:2:8, 36:5:6:3, 36:5:6:5,

TABLE 5-continued

Exemplary Enumerated Compounds using Tables 1, 2, 3, and 4

36:5:7:1, 36:5:7:5, 36:5:7:6, 36:5:13:1, 36:5:13:3, 36:5:17:3,
36:5:17:5, 36:5:17:6, 36:5:17:8, 36:5:19:2, 36:5:19:6, 36:5:19:7,
36:5:19:8, 36:5:22:1, 36:5:22:2, 36:5:23:1, 36:5:23:5, 36:5:23:6,
36:5:25:3, 36:5:25:7, 36:5:26:3, 36:5:26:4, 36:5:26:6, 36:5:29:1,
36:5:29:6, 36:5:29:7, 36:5:29:8, 36:5:30:1, 36:5:30:3, 36:5:30:8,
36:5:31:1, 36:5:31:7, 36:5:37:1, 36:5:37:2, 36:5:40:2, 36:5:40:3,
36:5:40:7, 36:5:40:8, 40:1:1:2, 40:1:1:3, 40:1:1:7, 40:1:2:3, 40:1:2:4,
40:1:2:5, 40:1:3:1, 40:1:3:2, 40:1:3:7, 40:1:4:2, 40:1:4:4, 40:1:4:5,
40:1:5:3, 40:1:5:5, 40:1:5:8, 40:1:7:3, 40:1:7:4, 40:1:7:7, 40:1:7:8,
40:1:9:1, 40:1:9:4, 40:1:9:6, 40:1:10:3, 40:1:10:4, 40:1:11:2,
40:1:11:4, 40:1:11:6, 40:1:11:7, 40:1:12:5, 40:1:12:7, 40:1:12:8,
40:1:13:3, 40:1:13:6, 40:1:17:2, 40:1:17:6, 40:1:17:7, 40:1:20:1,
40:1:20:4, 40:1:20:6, 40:1:20:7, 40:1:22:2, 40:1:22:3, 40:1:22:6,
40:1:22:7, 40:1:23:4, 40:1:23:6, 40:1:28:2, 40:1:28:3, 40:1:28:6,
40:1:28:7, 40:1:32:6, 40:1:32:7, 40:1:33:1, 40:1:33:2, 40:1:33:3,
40:1:33:5, 40:1:35:3, 40:1:35:4, 40:1:35:6, 40:1:35:7, 40:1:41:2,
40:1:41:5, 40:1:41:6, 40:2:3:2, 40:2:3:3, 40:2:7:4, 40:2:7:5, 40:2:8:1,
40:2:8:4, 40:2:8:7, 40:2:8:8, 40:2:9:3, 40:2:9:4, 40:2:9:5, 40:2:9:6,
40:2:11:1, 40:2:11:3, 40:2:11:6, 40:2:11:8, 40:2:12:1, 40:2:12:5,
40:2:12:6, 40:2:12:7, 40:2:15:3, 40:2:15:4, 40:2:15:6, 40:2:17:3,
40:2:17:4, 40:2:17:6, 40:2:17:8, 40:2:18:3, 40:2:18:8, 40:2:22:5,
40:2:22:6, 40:2:22:7, 40:2:23:6, 40:2:23:7, 40:2:25:1, 40:2:25:2,
40:2:25:3, 40:2:25:7, 40:2:26:2, 40:2:26:6, 40:2:26:8, 40:2:29:3,
40:2:29:5, 40:2:33:2, 40:2:33:4, 40:2:33:6, 40:2:33:8, 40:2:34:1,
40:2:34:2, 40:2:34:4, 40:2:34:6, 40:2:35:2, 40:2:35:4, 40:2:35:6,
40:2:39:2, 40:2:39:3, 40:3:1:3, 40:3:1:5, 40:3:1:7, 40:3:4:3, 40:3:4:5,
40:3:4:6, 40:3:4:7, 40:3:5:1, 40:3:5:5, 40:3:7:2, 40:3:7:5, 40:3:7:7,
40:3:7:8, 40:3:8:1, 40:3:8:2, 40:3:8:5, 40:3:8:7, 40:3:9:1, 40:3:9:4,
40:3:9:6, 40:3:11:3, 40:3:11:7, 40:3:11:8, 40:3:13:4, 40:3:13:6,
40:3:14:1, 40:3:14:2, 40:3:14:3, 40:3:21:5, 40:3:21:7, 40:3:21:8,
40:3:23:1, 40:3:23:3, 40:3:23:6, 40:3:23:8, 40:3:28:2, 40:3:28:4,
40:3:28:7, 40:3:28:8, 40:3:30:1, 40:3:30:7, 40:3:32:1, 40:3:32:2,
40:3:32:4, 40:3:32:8, 40:3:34:2, 40:3:34:6, 40:3:36:1, 40:3:36:3,
40:3:40:1, 40:3:40:4, 40:3:40:6, 40:3:40:7, 40:4:1:1, 40:4:1:3,
40:4:1:4, 40:4:1:6, 40:4:6:3, 40:4:6:7, 40:4:10:7, 40:4:10:8,
40:4:11:1, 40:4:11:3, 40:4:11:7, 40:4:11:8, 40:4:14:3, 40:4:14:4,
40:4:14:5, 40:4:16:6, 40:4:16:7, 40:4:18:3, 40:4:18:6, 40:4:20:2,
40:4:20:3, 40:4:22:3, 40:4:22:8, 40:4:23:3, 40:4:23:8, 40:4:24:1,
40:4:24:6, 40:4:24:8, 40:4:25:1, 40:4:25:3, 40:4:25:4, 40:4:25:5,
40:4:26:3, 40:4:26:5, 40:4:26:7, 40:4:27:1, 40:4:27:2, 40:4:27:8,
40:4:32:4, 40:4:32:5, 40:4:32:6, 40:4:32:8, 40:4:34:1, 40:4:34:3,
40:4:34:4, 40:4:34:7, 40:4:37:1, 40:4:37:2, 40:4:37:4, 40:4:37:5,
40:4:39:1, 40:4:39:3, 40:4:39:6, 40:4:39:7, 40:6:3:3, 40:6:3:6,
40:6:3:7, 40:6:3:8, 40:6:8:6, 40:6:8:7, 40:6:18:1, 40:6:18:5,
40:6:18:8, 40:6:19:7, 40:6:19:8, 40:6:21:1, 40:6:21:2, 40:6:21:3,
40:6:21:4, 40:6:23:2, 40:6:23:3, 40:6:23:6, 40:6:26:1, 40:6:26:5,
40:6:26:8, 40:6:29:5, 40:6:29:6, 40:6:34:2, 40:6:34:4, 40:6:34:5,
40:6:34:7, 40:6:36:2, 40:6:36:6, 40:6:39:1, 40:6:39:2, 40:6:39:7,
40:6:41:3, 40:6:41:5, 40:6:41:6, 40:6:41:8, 41:4:2:1, 41:4:2:2,
41:4:2:6, 41:4:6:1, 41:4:6:3, 41:4:6:5, 41:4:8:2, 41:4:8:4, 41:4:8:5,
41:4:8:6, 41:4:9:2, 41:4:9:5, 41:4:9:7, 41:4:9:8, 41:4:10:5, 41:4:10:6,
41:4:13:4, 41:4:13:7, 41:4:19:3, 41:4:19:4, 41:4:19:8, 41:4:23:5,
41:4:23:6, 41:4:25:1, 41:4:25:2, 41:4:25:4, 41:4:25:8, 41:4:31:1,
41:4:31:2, 41:4:31:6, 41:4:35:3, 41:4:35:6, 41:4:35:8, 41:4:36:1,
41:4:36:6, 41:4:36:7, 41:4:38:6, 41:4:38:7, 41:4:41:3, 41:4:41:8,
41:5:4:1, 41:5:4:2, 41:5:4:6, 41:5:4:8, 41:5:6:1, 41:5:6:3, 41:5:6:6,
41:5:6:8, 41:5:7:4, 41:5:7:6, 41:5:7:8, 41:5:8:3, 41:5:8:5, 41:5:8:7,
41:5:13:2, 41:5:13:6, 41:5:13:7, 41:5:14:3, 41:5:14:4, 41:5:17:3,
41:5:17:5, 41:5:17:7, 41:5:17:8, 41:5:19:1, 41:5:19:4, 41:5:19:5,
41:5:19:7, 41:5:24:3, 41:5:24:5, 41:5:24:6, 41:5:24:7, 41:5:26:2,
41:5:26:4, 41:5:26:7, 41:5:27:4, 41:5:27:7, 41:5:32:4, 41:5:32:5,
41:5:32:6, 41:5:39:1, 41:5:39:5, 41:5:39:7, 41:5:40:1, 41:5:40:2,
41:5:40:7, 41:5:40:8, 48:1:1:2, 48:1:1:3, 48:1:2:1, 48:1:2:2, 48:1:2:3,
48:1:2:7, 48:1:6:3, 48:1:6:6, 48:1:8:3, 48:1:8:4, 48:1:8:7, 48:1:11:1,
48:1:11:2, 48:1:16:2, 48:1:16:3, 48:1:16:6, 48:1:16:7, 48:1:22:4,
48:1:22:7, 48:1:22:8, 48:1:39:3, 48:1:39:4, 48:1:39:6, 48:1:40:5,
48:1:40:8, 48:2:2:4, 48:2:2:6, 48:2:4:2, 48:2:4:6, 48:2:8:2, 48:2:8:3,
48:2:9:7, 48:2:9:8, 48:2:11:3, 48:2:11:5, 48:2:13:1, 48:2:13:2,
48:2:13:4, 48:2:13:8, 48:2:16:2, 48:2:16:6, 48:2:18:4, 48:2:18:5,
48:2:18:6, 48:2:18:8, 48:2:19:1, 48:2:19:4, 48:2:19:5, 48:2:19:8,
48:2:25:5, 48:2:25:6, 48:2:27:1, 48:2:27:3, 48:2:27:5, 48:2:27:8,
48:2:29:1, 48:2:29:4, 48:2:29:8, 48:2:30:4, 48:2:30:6, 48:2:30:8,
48:2:33:2, 48:2:33:6, 48:2:33:7, 48:2:34:1, 48:2:34:2, 48:2:34:8,
48:2:35:6, 48:2:35:7, 48:2:35:8, 48:2:41:4, 48:2:41:5, 48:2:41:6,
48:2:41:8, 48:3:1:2, 48:3:1:4, 48:3:1:6, 48:3:1:7, 48:3:2:1, 48:3:2:2,
48:3:2:6, 48:3:5:1, 48:3:5:5, 48:3:5:6, 48:3:5:7, 48:3:7:3, 48:3:7:4,
48:3:7:7, 48:3:7:8, 48:3:8:2, 48:3:8:3, 48:3:8:7, 48:3:8:8, 48:3:10:1,

TABLE 5-continued

Exemplary Enumerated Compounds using Tables 1, 2, 3, and 4

| | | | | | | |
|---|---|---|---|---|---|---|
| 48:3:10:4, | 48:3:10:5, | 48:3:10:7, | 48:3:12:1, | 48:3:12:5, | 48:3:12:6, | |
| 48:3:12:7, | 48:3:19:4, | 48:3:19:5, | 48:3:19:6, | 48:3:19:8, | 48:3:21:1, | |
| 48:3:21:3, | 48:3:21:5, | 48:3:21:8, | 48:3:22:1, | 48:3:22:2, | 48:3:22:3, | |
| 48:3:22:5, | 48:3:26:1, | 48:3:26:3, | 48:3:26:7, | 48:3:26:8, | 48:3:28:1, | |
| 48:3:28:3, | 48:3:28:5, | 48:3:28:7, | 48:3:33:3, | 48:3:33:5, | 48:3:33:7, | |
| 48:3:34:4, | 48:3:34:5, | 48:3:34:8, | 48:3:35:1, | 48:3:35:2, | 48:3:35:6, | |
| 48:3:35:8, | 48:3:37:1, | 48:3:37:4, | 48:3:37:6, | 48:3:40:3, | 48:3:40:8, | |
| 48:3:41:2, | 48:3:41:3, | 48:4:2:4, | 48:4:2:6, | 48:4:3:4, | 48:4:3:6, | 48:4:3:8, |
| 48:4:6:3, | 48:4:6:6, | 48:4:7:1, | 48:4:7:6, | 48:4:9:5, | 48:4:9:6, | 48:4:9:7, |
| 48:4:9:8, | 48:4:12:1, | 48:4:12:5, | 48:4:12:6, | 48:4:13:6, | 48:4:13:8, | |
| 48:4:14:1, | 48:4:14:2, | 48:4:14:3, | 48:4:14:4, | 48:4:17:2, | 48:4:17:8, | |
| 48:4:19:1, | 48:4:19:3, | 48:4:19:5, | 48:4:19:7, | 48:4:21:2, | 48:4:21:6, | |
| 48:4:21:7, | 48:4:23:1, | 48:4:23:8, | 48:4:24:2, | 48:4:24:3, | 48:4:24:5, | |
| 48:4:24:7, | 48:4:27:3, | 48:4:27:4, | 48:4:27:6, | 48:4:27:8, | 48:4:28:2, | |
| 48:4:28:4, | 48:4:28:6, | 48:4:28:7, | 48:4:29:1, | 48:4:29:3, | 48:4:29:4, | |
| 48:4:35:3, | 48:4:35:4, | 48:4:35:8, | 48:4:36:2, | 48:4:36:4, | 48:4:36:6, | |
| 48:4:36:8, | 48:4:39:3, | 48:4:39:5, | 48:4:39:6, | 48:4:39:8, | 48:5:2:4, | |
| 48:5:2:5, | 48:5:7:1, | 48:5:7:4, | 48:5:7:8, | 48:5:10:4, | 48:5:10:5, | |
| 48:5:10:7, | 48:5:10:8, | 48:5:12:1, | 48:5:12:5, | 48:5:15:2, | 48:5:15:3, | |
| 48:5:17:4, | 48:5:17:5, | 48:5:24:2, | 48:5:24:5, | 48:5:25:7, | 48:5:25:8, | |
| 48:5:26:1, | 48:5:26:6, | 48:5:26:7, | 48:5:26:8, | 48:5:27:2, | 48:5:27:8, | |
| 48:5:31:1, | 48:5:31:6, | 48:5:34:3, | 48:5:34:6, | 48:5:34:8, | 48:5:35:3, | |
| 48:5:35:4, | 48:5:35:6, | 48:5:35:8, | 48:5:38:2, | 48:5:38:3, | 48:5:38:6, | |
| 48:5:39:1, | 48:5:39:3, | 48:5:39:8, | 49:1:2:3, | 49:1:2:5, | 49:1:2:6, | |
| 49:1:2:8, | 49:1:4:2, | 49:1:4:4, | 49:1:4:5, | 49:1:4:7, | 49:1:5:2, | 49:1:5:3, |
| 49:1:5:5, | 49:1:8:1, | 49:1:8:3, | 49:1:8:8, | 49:1:11:2, | 49:1:11:4, | |
| 49:1:11:5, | 49:1:11:6, | 49:1:12:1, | 49:1:12:2, | 49:1:15:1, | 49:1:15:2, | |
| 49:1:15:7, | 49:1:17:1, | 49:1:17:4, | 49:1:17:5, | 49:1:17:7, | 49:1:19:1, | |
| 49:1:19:5, | 49:1:19:6, | 49:1:19:8, | 49:1:24:1, | 49:1:24:2, | 49:1:24:3, | |
| 49:1:24:7, | 49:1:25:2, | 49:1:25:5, | 49:1:25:7, | 49:1:25:8, | 49:1:30:2, | |
| 49:1:30:4, | 49:1:30:7, | 49:1:41:1, | 49:1:41:2, | 49:1:41:4, | 49:1:41:7, | |
| 49:4:2:1, | 49:4:2:4, | 49:4:2:7, | 49:4:4:3, | 49:4:4:4, | 49:4:4:5, | 49:4:4:6, |
| 49:4:7:3, | 49:4:7:5, | 49:4:7:8, | 49:4:8:1, | 49:4:8:5, | 49:4:9:2, | 49:4:9:7, |
| 49:4:9:8, | 49:4:12:1, | 49:4:12:5, | 49:4:13:4, | 49:4:13:6, | 49:4:16:3, | |
| 49:4:16:6, | 49:4:16:8, | 49:4:31:2, | 49:4:31:8, | 49:4:38:2, | 49:4:38:7, | |
| 49:4:39:2, | 49:4:39:6, | 49:4:39:7, | 49:4:39:8, | 51:1:3:2, | 51:1:3:8, | |
| 51:1:11:1, | 51:1:11:3, | 51:1:11:8, | 51:1:16:1, | 51:1:16:6, | 51:1:16:8, | |
| 51:1:21:2, | 51:1:21:5, | 51:1:21:8, | 51:1:23:1, | 51:1:23:2, | 51:1:23:3, | |
| 51:1:23:8, | 51:1:30:3, | 51:1:30:8, | 51:1:34:3, | 51:1:34:5, | 51:1:34:6, | |
| 51:1:36:2, | 51:1:36:5, | 51:1:36:6, | 51:1:36:7, | 51:1:38:2, | 51:1:38:4, | |
| 51:1:38:5, | 51:1:38:8, | 51:3:2:3, | 51:3:2:6, | 51:3:2:7, | 51:3:5:3, | 51:3:5:7, |
| 51:3:9:5, | 51:3:9:7, | 51:3:10:1, | 51:3:10:6, | 51:3:10:8, | 51:3:17:2, | |
| 51:3:17:8, | 51:3:18:3, | 51:3:18:4, | 51:3:18:6, | 51:3:19:1, | 51:3:19:6, | |
| 51:3:20:6, | 51:3:20:8, | 51:3:21:5, | 51:3:21:8, | 51:3:23:1, | 51:3:23:4, | |
| 51:3:23:8, | 51:3:24:1, | 51:3:24:2, | 51:3:24:7, | 51:3:24:8, | 51:3:28:6, | |
| 51:3:28:7, | 51:3:31:4, | 51:3:31:8, | 51:3:32:1, | 51:3:32:2, | 51:3:32:5, | |
| 51:3:32:8, | 51:3:33:4, | 51:3:33:5, | 51:3:33:6, | 51:3:34:2, | 51:3:34:4, | |
| 51:3:34:7, | 51:3:36:1, | 51:3:36:2, | 51:3:36:6, | 51:3:36:8, | 51:3:37:2, | |
| 51:3:37:5, | 51:3:37:7, | 51:3:40:1, | 51:3:40:4, | 51:3:40:5, | 51:3:40:7, | |
| 51:5:1:1, | 51:5:1:2, | 51:5:1:4, | 51:5:4:1, | 51:5:4:2, | 51:5:8:5, | 51:5:8:6, |
| 51:5:8:8, | 51:5:10:4, | 51:5:10:5, | 51:5:10:6, | 51:5:13:1, | 51:5:13:3, | |
| 51:5:13:8, | 51:5:16:1, | 51:5:16:2, | 51:5:16:4, | 51:5:16:6, | 51:5:18:4, | |
| 51:5:18:6, | 51:5:19:2, | 51:5:19:3, | 51:5:19:5, | 51:5:20:5, | 51:5:20:8, | |
| 51:5:21:1, | 51:5:21:5, | 51:5:21:6, | 51:5:22:1, | 51:5:22:3, | 51:5:24:2, | |
| 51:5:24:6, | 51:5:25:4, | 51:5:25:8, | 51:5:27:4, | 51:5:27:7, | 51:5:28:3, | |
| 51:5:28:6, | 51:5:28:8, | 51:5:30:2, | 51:5:30:5, | 51:5:30:7, | 51:5:30:8, | |
| 51:5:31:1, | 51:5:31:3, | 51:5:31:4, | 51:5:35:1, | 51:5:35:3, | 51:5:35:5, | |
| 51:5:35:8, | 51:5:40:4, | 51:5:40:5, | 58:2:4:1, | 58:2:4:6, | 58:2:11:1, | |
| 58:2:11:3, | 58:2:11:4, | 58:2:11:5, | 58:2:14:3, | 58:2:14:4, | 58:2:14:6, | |
| 58:2:14:8, | 58:2:17:6, | 58:2:17:7, | 58:2:17:8, | 58:2:19:1, | 58:2:19:4, | |
| 58:2:21:1, | 58:2:21:3, | 58:2:23:6, | 58:2:23:7, | 58:2:27:6, | 58:2:27:7, | |
| 58:2:30:1, | 58:2:30:6, | 58:2:33:4, | 58:2:33:7, | 58:2:35:2, | 58:2:35:5, | |
| 58:2:35:7, | 58:2:35:8, | 58:2:36:7, | 58:2:36:8, | 58:2:37:2, | 58:2:37:4, | |
| 58:2:38:3, | 58:2:38:4, | 58:2:38:5, | 58:2:39:2, | 58:2:39:5, | 58:2:39:8, | |
| 58:6:2:1, | 58:6:2:6, | 58:6:2:7, | 58:6:8:3, | 58:6:8:4, | 58:6:8:7, | 58:6:10:1, |
| 58:6:10:7, | 58:6:10:8, | 58:6:11:5, | 58:6:11:8, | 58:6:14:3, | 58:6:14:5, | |
| 58:6:18:4, | 58:6:18:5, | 58:6:21:1, | 58:6:21:7, | 58:6:22:3, | 58:6:22:4, | |
| 58:6:22:7, | 58:6:23:2, | 58:6:23:3, | 58:6:27:2, | 58:6:27:4, | 58:6:27:5, | |
| 58:6:28:5, | 58:6:28:6, | 58:6:28:7, | 58:6:28:8, | 58:6:29:1, | 58:6:29:6, | |
| 58:6:31:4, | 58:6:31:6, | 58:6:31:7, | 58:6:32:2, | 58:6:32:8, | 58:6:35:3, | |
| 58:6:35:7, | 58:6:37:2, | 58:6:37:8, | 58:6:38:2, | 58:6:38:8, | 58:6:41:3, | |
| 58:6:41:5, | 58:6:41:7, | 58:6:41:8, | 62:1:1:2, | 62:1:1:3, | 62:1:1:5, | |
| 62:1:1:8, | 62:1:5:1, | 62:1:5:5, | 62:1:7:2, | 62:1:7:6, | 62:1:13:2, | 62:1:13:3, |
| 62:1:13:7, | 62:1:14:1, | 62:1:14:2, | 62:1:14:6, | 62:1:14:7, | 62:1:16:1, | |
| 62:1:16:4, | 62:1:16:7, | 62:1:16:8, | 62:1:17:1, | 62:1:17:4, | 62:1:17:7, | |
| 62:1:18:3, | 62:1:18:6, | 62:1:18:7, | 62:1:18:8, | 62:1:20:2, | 62:1:20:4, | |
| 62:1:20:6, | 62:1:20:7, | 62:1:22:3, | 62:1:22:7, | 62:1:23:1, | 62:1:23:2, | |

TABLE 5-continued

Exemplary Enumerated Compounds using Tables 1, 2, 3, and 4

62:1:23:7, 62:1:30:3, 62:1:30:8, 62:1:38:4, 62:1:38:7, 62:1:40:2,
62:1:40:3, 62:1:40:6, 62:1:40:7, 62:1:41:1, 62:1:41:2, 62:1:41:3,
62:1:41:4, 62:2:1:3, 62:2:1:6, 62:2:4:2, 62:2:4:3, 62:2:4:4, 62:2:4:5,
62:2:12:2, 62:2:12:3, 62:2:13:4, 62:2:13:5, 62:2:13:6, 62:2:17:1,
62:2:17:4, 62:2:17:6, 62:2:17:7, 62:2:24:1, 62:2:24:3, 62:2:24:4,
62:2:24:8, 62:2:34:3, 62:2:34:4, 62:2:34:5, 62:2:34:7, 62:2:39:1,
62:2:39:3, 62:2:39:5, 62:2:39:7, 62:2:40:1, 62:2:40:2, 62:2:40:3,
62:2:40:4, 62:3:4:1, 62:3:4:6, 62:3:4:7, 62:3:4:8, 62:3:6:2, 62:3:6:4,
62:3:6:6, 62:3:10:2, 62:3:10:3, 62:3:10:5, 62:3:10:8, 62:3:11:4,
62:3:11:8, 62:3:12:3, 62:3:12:6, 62:3:15:5, 62:3:15:6, 62:3:15:7,
62:3:17:1, 62:3:17:7, 62:3:17:8, 62:3:26:1, 62:3:26:2, 62:3:26:4,
62:3:27:2, 62:3:27:8, 62:3:28:1, 62:3:28:2, 62:3:29:2, 62:3:29:6,
62:3:29:7, 62:3:29:8, 62:3:31:3, 62:3:31:7, 62:3:32:2, 62:3:32:5,
62:6:3:3, 62:6:3:5, 62:6:3:8, 62:6:6:4, 62:6:6:5, 62:6:6:8, 62:6:10:4,
62:6:10:5, 62:6:10:6, 62:6:10:8, 62:6:12:1, 62:6:12:5, 62:6:15:2,
62:6:15:6, 62:6:17:1, 62:6:17:4, 62:6:17:5, 62:6:18:5, 62:6:18:7,
62:6:18:8, 62:6:20:3, 62:6:20:5, 62:6:21:2, 62:6:21:3, 62:6:21:4,
62:6:21:5, 62:6:23:2, 62:6:23:5, 62:6:23:6, 62:6:24:2, 62:6:24:3,
62:6:24:6, 62:6:24:8, 62:6:26:3, 62:6:26:4, 62:6:26:6, 62:6:26:8,
62:6:30:1, 62:6:30:2, 62:6:30:3, 62:6:30:8, 62:6:34:3, 62:6:34:5,
62:6:40:3, 62:6:40:6, 70:1:9:1, 70:1:9:2, 70:1:9:5, 70:1:9:8,
70:1:10:2, 70:1:10:8, 70:1:11:1, 70:1:11:3, 70:1:11:4, 70:1:15:3,
70:1:15:6, 70:1:15:7, 70:1:17:4, 70:1:17:5, 70:1:17:6, 70:1:17:8,
70:1:35:1, 70:1:35:2, 70:1:35:3, 70:1:35:7, 70:1:38:3, 70:1:38:4,
70:1:38:7, 70:1:40:1, 70:1:40:2, 70:1:40:3, 70:1:40:8, 70:2:6:2,
70:2:6:5, 70:2:6:8, 70:2:7:1, 70:2:7:3, 70:2:7:4, 70:2:15:2, 70:2:15:3,
70:2:15:5, 70:2:18:1, 70:2:18:4, 70:2:18:6, 70:2:18:7, 70:2:25:4,
70:2:25:6, 70:2:27:1, 70:2:27:2, 70:2:27:4, 70:2:27:5, 70:2:29:2,
70:2:29:8, 70:2:36:1, 70:2:36:2, 70:2:37:2, 70:2:37:4, 70:2:37:5,
70:2:37:7, 70:2:38:2, 70:2:38:4, 70:3:9:3, 70:3:9:7, 70:3:10:1,
70:3:10:2, 70:3:10:6, 70:3:10:8, 70:3:12:5, 70:3:12:8, 70:3:14:3,
70:3:14:4, 70:3:14:5, 70:3:14:8, 70:3:16:2, 70:3:16:7, 70:3:17:2,
70:3:17:4, 70:3:17:6, 70:3:17:8, 70:3:19:6, 70:3:19:7, 70:3:19:8,
70:3:23:2, 70:3:23:5, 70:3:23:6, 70:3:24:1, 70:3:24:4, 70:3:24:5,
70:3:24:6, 70:3:32:4, 70:3:32:5, 70:3:35:4, 70:3:35:5, 70:3:36:4,
70:3:36:6, 70:3:37:2, 70:3:37:5, 70:3:39:4, 70:3:39:7, 70:3:40:3,
70:3:40:4, 70:3:40:8, 70:4:4:3, 70:4:4:5, 70:4:4:6, 70:4:8:2, 70:4:8:6,
70:4:8:7, 70:4:8:8, 70:4:11:6, 70:4:11:8, 70:4:14:1, 70:4:14:4,
70:4:14:6, 70:4:14:8, 70:4:18:1, 70:4:18:4, 70:4:21:3, 70:4:21:6,
70:4:21:8, 70:4:26:2, 70:4:26:4, 70:4:37:1, 70:4:37:4, 70:4:37:5,
70:4:37:8, 70:4:39:3, 70:4:39:4, 70:4:39:7, 70:5:15:3, 70:5:15:4,
70:5:15:6, 70:5:15:7, 70:5:16:5, 70:5:16:7, 70:5:18:2, 70:5:18:3,
70:5:18:6, 70:5:18:8, 70:5:25:1, 70:5:25:5, 70:5:25:8, 70:5:29:2,
70:5:29:4, 70:5:29:7, 70:5:29:8, 70:5:36:1, 70:5:36:3, 70:5:36:4,
70:5:36:8, 70:5:38:6, 70:5:38:7, 70:5:41:1, 70:5:41:8, 80:1:4:1,
80:1:4:3, 80:1:7:2, 80:1:7:5, 80:1:7:6, 80:1:18:3, 80:1:18:8,
80:1:21:2, 80:1:21:4, 80:1:21:7, 80:1:22:1, 80:1:22:2, 80:1:22:3,
80:1:26:2, 80:1:26:4, 80:1:26:5, 80:1:26:6, 80:1:28:1, 80:1:28:4,
80:1:32:2, 80:1:32:6, 80:1:33:1, 80:1:33:2, 80:1:33:3, 80:1:33:4,
80:1:34:1, 80:1:34:2, 80:1:34:6, 80:1:36:2, 80:1:36:8, 80:2:2:1,
80:2:2:5, 80:2:5:5, 80:2:5:7, 80:2:5:8, 80:2:6:1, 80:2:6:4, 80:2:6:5,
80:2:7:3, 80:2:7:7, 80:2:9:3, 80:2:9:5, 80:2:9:6, 80:2:9:7, 80:2:14:1,
80:2:14:4, 80:2:14:5, 80:2:14:8, 80:2:17:2, 80:2:17:5, 80:2:17:6,
80:2:17:7, 80:2:19:2, 80:2:19:4, 80:2:19:6, 80:2:22:2, 80:2:22:4,
80:2:25:1, 80:2:25:2, 80:2:28:2, 80:2:28:6, 80:2:28:8, 80:2:30:1,
80:2:30:2, 80:2:30:4, 80:2:30:5, 80:2:36:4, 80:2:36:6, 80:6:3:1,
80:6:3:4, 80:6:3:5, 80:6:7:1, 80:6:7:8, 80:6:13:1, 80:6:13:2,
80:6:13:7, 80:6:16:6, 80:6:16:8, 80:6:25:2, 80:6:25:3, 80:6:25:6,
80:6:25:8, 80:6:26:4, 80:6:26:5, 80:6:26:7, 80:6:27:3, 80:6:27:4,
80:6:27:6, 80:6:27:7, 80:6:30:1, 80:6:30:2, 80:6:30:4, 80:6:30:8,
80:6:31:4, 80:6:31:6, 80:6:39:2, 80:6:39:4, 80:6:39:7, 85:1:3:2,
85:1:3:6, 85:1:3:7, 85:1:3:8, 85:1:4:2, 85:1:4:3, 85:1:4:4, 85:1:4:8,
85:1:5:4, 85:1:5:7, 85:1:5:8, 85:1:11:1, 85:1:11:3, 85:1:11:5,
85:1:11:7, 85:1:13:2, 85:1:13:8, 85:1:16:1, 85:1:16:3, 85:1:16:4,
85:1:16:8, 85:1:21:1, 85:1:21:2, 85:1:21:4, 85:1:21:5, 85:1:24:5,
85:1:24:7, 85:1:29:4, 85:1:29:6, 85:1:29:7, 85:1:34:2, 85:1:34:6,
85:1:34:8, 85:1:36:2, 85:1:36:3, 85:1:36:4, 85:1:36:5, 85:3:4:4,
85:3:4:6, 85:3:4:8, 85:3:8:1, 85:3:8:3, 85:3:8:6, 85:3:18:1, 85:3:18:2,
85:3:18:5, 85:3:18:8, 85:3:21:1, 85:3:21:2, 85:3:21:5, 85:3:21:8,
85:3:22:1, 85:3:22:2, 85:3:22:5, 85:3:22:7, 85:3:25:1, 85:3:25:4,
85:3:25:6, 85:3:25:8, 85:3:30:3, 85:3:30:4, 85:3:30:6, 85:3:32:2,
85:3:32:6, 85:3:32:7, 85:3:34:3, 85:3:34:4, 85:3:34:7, 85:3:34:8,
85:3:35:1, 85:3:35:4, 85:3:35:6, 85:3:35:8, 85:3:38:1, 85:3:38:5,
85:3:38:7, 85:3:38:8, 85:3:39:2, 85:3:39:5, 85:3:39:7, 85:3:39:8,
85:3:40:3, 85:3:40:5, 85:3:40:7, 85:5:1:3, 85:5:1:8, 85:5:3:2,
85:5:3:3, 85:5:3:4, 85:5:3:6, 85:5:7:2, 85:5:7:3, 85:5:7:6, 85:5:10:2,
85:5:10:7, 85:5:10:8, 85:5:15:2, 85:5:15:4, 85:5:18:1, 85:5:18:6,

TABLE 5-continued

Exemplary Enumerated Compounds using Tables 1, 2, 3, and 4

85:5:19:1, 85:5:19:2, 85:5:19:4, 85:5:19:8, 85:5:20:3, 85:5:20:4,
85:5:20:7, 85:5:30:3, 85:5:30:5, 85:5:30:7, 85:5:31:4, 85:5:31:6,
85:5:31:7, 85:5:34:1, 85:5:34:5, 85:5:36:1, 85:5:36:2, 85:5:36:3,
85:5:36:8, 85:5:37:7, 85:5:37:8, 85:5:41:2, 85:5:41:3, 85:5:41:8,
85:6:2:3, 85:6:2:4, 85:6:2:6, 85:6:2:8, 85:6:5:1, 85:6:5:3, 85:6:5:4,
85:6:6:3, 85:6:6:4, 85:6:6:7, 85:6:7:2, 85:6:7:3, 85:6:11:1, 85:6:11:3,
85:6:12:1, 85:6:12:2, 85:6:12:7, 85:6:12:8, 85:6:14:2, 85:6:14:3,
85:6:14:7, 85:6:14:8, 85:6:16:3, 85:6:16:5, 85:6:17:3, 85:6:17:6,
85:6:19:5, 85:6:19:7, 85:6:20:1, 85:6:20:4, 85:6:20:5, 85:6:20:7,
85:6:30:3, 85:6:30:4, 85:6:30:7, 85:6:36:5, 85:6:36:7, 85:6:36:8,
85:6:37:3, 85:6:37:4, 85:6:37:8, 85:6:39:1, 85:6:39:2, 85:6:39:4,
85:6:39:8, 88:1:2:1, 88:1:2:4, 88:1:2:6, 88:1:2:7, 88:1:8:3, 88:1:8:8,
88:1:9:5, 88:1:9:6, 88:1:9:7, 88:1:9:8, 88:1:10:1, 88:1:10:6,
88:1:10:7, 88:1:10:8, 88:1:11:1, 88:1:11:6, 88:1:11:8, 88:1:19:1,
88:1:19:3, 88:1:19:5, 88:1:19:6, 88:1:28:4, 88:1:28:5, 88:1:32:1,
88:1:32:2, 88:1:32:7, 88:1:32:8, 88:1:38:3, 88:1:38:5, 88:1:40:4,
88:1:40:6, 88:1:40:8, 88:2:3:6, 88:2:3:7, 88:2:10:3, 88:2:10:4,
88:2:10:8, 88:2:16:3, 88:2:16:8, 88:2:23:3, 88:2:23:4, 88:2:23:5,
88:2:23:7, 88:2:34:4, 88:2:34:7, 88:2:35:2, 88:2:35:3, 88:2:35:6,
88:2:35:7, 88:2:37:2, 88:2:37:4, 88:2:37:6, 88:2:37:8, 88:2:40:1,
88:2:40:2, 88:2:40:5, 88:2:41:1, 88:2:41:4, 88:2:41:5, 88:2:41:8,
88:3:2:4, 88:3:2:5, 88:3:2:8, 88:3:6:4, 88:3:6:6, 88:3:6:7, 88:3:7:3,
88:3:7:8, 88:3:8:1, 88:3:8:7, 88:3:11:3, 88:3:11:6, 88:3:11:7,
88:3:13:1, 88:3:13:2, 88:3:13:4, 88:3:13:7, 88:3:15:4, 88:3:15:6,
88:3:15:7, 88:3:15:8, 88:3:17:2, 88:3:17:7, 88:3:19:3, 88:3:19:4,
88:3:19:5, 88:3:19:8, 88:3:25:1, 88:3:25:3, 88:3:25:4, 88:3:25:5,
88:3:26:3, 88:3:26:5, 88:3:26:7, 88:3:26:8, 88:3:27:1, 88:3:27:3,
88:3:27:7, 88:3:28:2, 88:3:28:3, 88:3:30:1, 88:3:30:5, 88:3:30:6,
88:3:30:7, 88:3:31:1, 88:3:31:2, 88:3:31:4, 88:3:31:6, 88:3:34:2,
88:3:34:6, 88:3:34:7, 88:3:34:8, 88:3:35:6, 88:3:35:7, 88:3:36:2,
88:3:36:3, 88:3:36:4, 88:3:40:2, 88:3:40:5, 88:3:40:6, 88:3:40:8,
88:5:1:3, 88:5:1:4, 88:5:1:5, 88:5:2:2, 88:5:2:5, 88:5:2:6, 88:5:2:7,
88:5:5:1, 88:5:5:2, 88:5:5:3, 88:5:5:4, 88:5:9:2, 88:5:9:4, 88:5:9:5,
88:5:9:7, 88:5:12:1, 88:5:12:3, 88:5:12:8, 88:5:14:2, 88:5:14:3,
88:5:14:4, 88:5:16:3, 88:5:16:6, 88:5:16:8, 88:5:19:2, 88:5:19:3,
88:5:19:4, 88:5:19:5, 88:5:20:2, 88:5:20:3, 88:5:20:5, 88:5:25:1,
88:5:25:5, 88:5:27:7, 88:5:27:8, 88:5:29:1, 88:5:29:3, 88:5:29:6,
88:5:29:8, 88:5:30:1, 88:5:30:2, 88:5:30:3, 88:5:30:5, 88:5:31:1,
88:5:31:2, 88:5:31:6, 88:5:31:8, 88:5:37:2, 88:5:37:3, 88:5:37:5,
88:5:37:7, 88:5:38:3, 88:5:38:5, 88:5:38:6, 88:5:38:7, 88:5:39:4,
88:5:39:6, 88:5:40:6, 88:5:40:7, 88:5:41:4, 88:5:41:5, 88:5:41:7,
88:6:2:1, 88:6:2:2, 88:6:2:6, 88:6:4:2, 88:6:4:5, 88:6:4:6, 88:6:5:1,
88:6:5:2, 88:6:5:7, 88:6:5:8, 88:6:12:1, 88:6:12:2, 88:6:12:6,
88:6:14:4, 88:6:14:5, 88:6:14:7, 88:6:14:8, 88:6:17:2, 88:6:17:5,
88:6:20:3, 88:6:20:4, 88:6:20:5, 88:6:21:1, 88:6:21:2, 88:6:21:4,
88:6:25:4, 88:6:25:5, 88:6:25:6, 88:6:25:8, 88:6:32:3, 88:6:32:8,
88:6:34:2, 88:6:34:6, 88:6:39:1, 88:6:39:3, 88:6:39:4, 88:6:41:1,
88:6:41:3, 88:6:41:6, 88:6:41:7, 94:1:1:2, 94:1:1:3, 94:1:1:6,
94:1:1:8, 94:1:8:3, 94:1:8:7, 94:1:9:1, 94:1:9:2, 94:1:9:5, 94:1:9:8,
94:1:12:1, 94:1:12:6, 94:1:19:1, 94:1:19:6, 94:1:19:8, 94:1:22:2,
94:1:22:6, 94:1:22:7, 94:1:23:2, 94:1:23:3, 94:1:23:4, 94:1:23:5,
94:1:26:1, 94:1:26:5, 94:1:31:1, 94:1:31:3, 94:1:31:4, 94:1:31:5,
94:1:33:3, 94:1:33:4, 94:1:33:7, 94:1:36:1, 94:1:36:2, 94:1:36:5,
94:3:4:3, 94:3:4:6, 94:3:4:7, 94:3:6:3, 94:3:6:4, 94:3:6:6, 94:3:8:2,
94:3:8:5, 94:3:8:6, 94:3:8:8, 94:3:9:1, 94:3:9:2, 94:3:9:5, 94:3:9:7,
94:3:11:4, 94:3:11:6, 94:3:14:1, 94:3:14:5, 94:3:21:3, 94:3:21:6,
94:3:25:1, 94:3:25:2, 94:3:25:8, 94:3:29:2, 94:3:29:3, 94:3:29:4,
94:3:35:3, 94:3:35:5, 94:4:1:3, 94:4:1:4, 94:4:1:6, 94:4:1:8, 94:4:6:3,
94:4:6:4, 94:4:6:6, 94:4:6:7, 94:4:7:1, 94:4:7:3, 94:4:7:4, 94:4:8:2,
94:4:8:3, 94:4:8:6, 94:4:11:1, 94:4:11:7, 94:4:12:2, 94:4:12:6,
94:4:14:5, 94:4:14:7, 94:4:14:8, 94:4:15:1, 94:4:15:2, 94:4:15:4,
94:4:15:6, 94:4:17:1, 94:4:17:6, 94:4:18:1, 94:4:18:2, 94:4:18:3,
94:4:18:4, 94:4:23:4, 94:4:23:7, 94:4:26:1, 94:4:26:2, 94:4:26:7,
94:4:27:3, 94:4:27:6, 94:4:28:1, 94:4:28:4, 94:4:28:6, 94:4:28:8,
94:4:34:6, 94:4:34:8, 94:4:37:3, 94:4:37:5, 94:4:37:7, 94:4:37:8,
94:4:40:1, 94:4:40:2, 94:4:40:8, 94:4:41:1, 94:4:41:2, 94:4:41:6,
94:4:41:8, 98:1:3:4, 98:1:3:6, 98:1:4:1, 98:1:4:2, 98:1:4:3, 98:1:5:2,
98:1:5:4, 98:1:5:7, 98:1:6:2, 98:1:6:3, 98:1:6:7, 98:1:6:8, 98:1:10:1,
98:1:10:2, 98:1:10:3, 98:1:10:8, 98:1:13:4, 98:1:13:6, 98:1:13:7,
98:1:18:1, 98:1:18:4, 98:1:18:5, 98:1:18:7, 98:1:22:1, 98:1:22:3,
98:1:22:7, 98:1:22:8, 98:1:26:1, 98:1:26:2, 98:1:31:2, 98:1:31:3,
98:1:31:5, 98:1:33:2, 98:1:33:6, 98:1:34:6, 98:1:34:8, 98:1:35:2,
98:1:35:6, 98:1:38:2, 98:1:38:8, 98:1:39:3, 98:1:39:6, 98:1:39:7,
98:1:41:1, 98:1:41:3, 98:1:41:7, 98:1:41:8, 98:2:1:1, 98:2:1:3,
98:2:1:5, 98:2:1:7, 98:2:3:1, 98:2:3:5, 98:2:3:6, 98:2:3:8, 98:2:4:4,
98:2:4:5, 98:2:4:7, 98:2:7:5, 98:2:7:6, 98:2:7:8, 98:2:9:3, 98:2:9:4,
98:2:9:5, 98:2:13:4, 98:2:13:5, 98:2:13:7, 98:2:14:1, 98:2:14:4,

TABLE 5-continued

Exemplary Enumerated Compounds using Tables 1, 2, 3, and 4

98:2:14:6, 98:2:14:8, 98:2:18:1, 98:2:18:2, 98:2:18:5, 98:2:18:8,
98:2:19:3, 98:2:19:4, 98:2:19:7, 98:2:20:5, 98:2:20:7, 98:2:21:1,
98:2:21:3, 98:2:21:4, 98:2:21:5, 98:2:22:1, 98:2:22:4, 98:2:22:5,
98:2:22:8, 98:2:28:5, 98:2:28:6, 98:2:28:8, 98:2:31:2, 98:2:31:3,
98:2:31:4, 98:2:32:1, 98:2:32:2, 98:2:32:5, 98:2:32:7, 98:2:33:1,
98:2:33:3, 98:2:33:7, 98:2:33:8, 98:2:34:4, 98:2:34:7, 98:2:34:8,
98:2:36:1, 98:2:36:8, 98:3:4:1, 98:3:4:3, 98:3:4:4, 98:3:4:7, 98:3:5:1,
98:3:5:3, 98:3:5:8, 98:3:6:1, 98:3:6:3, 98:3:6:7, 98:3:7:3, 98:3:7:5,
98:3:12:1, 98:3:12:4, 98:3:12:5, 98:3:14:1, 98:3:14:3, 98:3:14:8,
98:3:19:2, 98:3:19:5, 98:3:19:8, 98:3:21:1, 98:3:21:5, 98:3:21:6,
98:3:23:6, 98:3:23:8, 98:3:24:5, 98:3:24:8, 98:3:25:1, 98:3:25:3,
98:3:26:1, 98:3:26:3, 98:3:26:5, 98:3:26:8, 98:3:28:2, 98:3:28:3,
98:3:28:4, 98:3:29:3, 98:3:29:4, 98:3:29:7, 98:3:29:8, 98:3:30:4,
98:3:30:8, 98:3:31:3, 98:3:31:4, 98:3:31:6, 98:3:33:3, 98:3:33:4,
98:3:33:5, 98:3:37:2, 98:3:37:3, 98:3:37:5, 98:3:37:8, 98:3:38:4,
98:3:38:5, 98:3:38:6, 98:3:38:8, 98:4:1:2, 98:4:1:3, 98:4:2:3,
98:4:2:4, 98:4:2:6, 98:4:2:8, 98:4:4:6, 98:4:4:8, 98:4:6:1, 98:4:6:2,
98:4:6:5, 98:4:6:6, 98:4:7:1, 98:4:7:3, 98:4:7:4, 98:4:7:6, 98:4:14:1,
98:4:14:2, 98:4:14:4, 98:4:14:7, 98:4:17:2, 98:4:17:5, 98:4:17:6,
98:4:17:7, 98:4:19:1, 98:4:19:6, 98:4:27:1, 98:4:27:3, 98:4:27:5,
98:4:27:6, 98:4:30:1, 98:4:30:2, 98:4:30:4, 98:4:30:8, 98:4:33:5,
98:4:33:8, 98:4:34:1, 98:4:34:4, 98:4:34:8, 98:4:37:2, 98:4:37:3,
98:4:37:4, 98:5:2:5, 98:5:2:6, 98:5:2:8, 98:5:3:2, 98:5:3:6, 98:5:3:8,
98:5:6:5, 98:5:6:6, 98:5:9:1, 98:5:9:6, 98:5:9:7, 98:5:11:6, 98:5:11:8,
98:5:12:2, 98:5:12:8, 98:5:19:2, 98:5:19:3, 98:5:19:7, 98:5:20:2,
98:5:20:6, 98:5:20:8, 98:5:27:2, 98:5:27:5, 98:5:27:7, 98:5:31:1,
98:5:31:4, 98:5:31:5, 98:5:38:1, 98:5:38:5, 98:5:38:8, 98:5:40:5,
98:5:40:6, 98:5:40:8

TABLE 5a

Exemplary Enumerated Compounds using Tables 1a, 2a, 3, and 4

1:9:2:4, 1:9:2:6, 1:9:2:8, 1:9:8:2, 1:9:8:3, 1:9:8:5, 1:9:8:8, 1:9:9:4,
1:9:9:6, 1:9:9:8, 1:9:11:3, 1:9:11:7, 1:9:11:8, 1:9:13:1, 1:9:13:3,
1:9:13:8, 1:9:16:1, 1:9:16:5, 1:9:16:8, 1:9:21:3, 1:9:21:4, 1:9:21:6,
1:9:21:8, 1:9:24:2, 1:9:24:4, 1:9:28:1, 1:9:28:2, 1:9:28:5, 1:9:28:8,
1:9:29:2, 1:9:29:6, 1:9:29:8, 1:9:37:1, 1:9:37:6, 1:9:40:1, 1:9:40:6,
1:9:40:7, 1:9:40:8, 1:12:3:4, 1:12:3:5, 1:12:3:7, 1:12:4:1, 1:12:4:5,
1:12:9:2, 1:12:9:3, 1:12:9:6, 1:12:10:3, 1:12:10:8, 1:12:11:2,
1:12:11:3, 1:12:11:6, 1:12:11:7, 1:12:15:1, 1:12:15:5, 1:12:15:6,
1:12:16:1, 1:12:16:2, 1:12:16:3, 1:12:16:5, 1:12:17:1, 1:12:17:5,
1:12:17:6, 1:12:18:2, 1:12:18:3, 1:12:18:7, 1:12:18:8, 1:12:19:1,
1:12:19:2, 1:12:19:3, 1:12:19:7, 1:12:21:2, 1:12:21:6, 1:12:21:8,
1:12:24:1, 1:12:24:3, 1:12:24:6, 1:12:28:1, 1:12:28:3, 1:12:28:6,
1:12:30:1, 1:12:30:2, 1:12:30:5, 1:12:30:8, 1:12:32:2, 1:12:32:4,
1:12:32:5, 1:12:32:8, 1:12:41:1, 1:12:41:4, 1:12:41:6, 1:12:41:8,
2:8:3:4, 2:8:3:5, 2:8:3:6, 2:8:3:7, 2:8:6:2, 2:8:6:3, 2:8:6:7, 2:8:8:2,
2:8:8:4, 2:8:8:6, 2:8:8:8, 2:8:9:4, 2:8:9:5, 2:8:9:7, 2:8:17:2,
2:8:17:5, 2:8:17:6, 2:8:17:7, 2:8:20:3, 2:8:20:5, 2:8:20:8, 2:8:23:2,
2:8:23:3, 2:8:23:5, 2:8:23:7, 2:8:25:2, 2:8:25:6, 2:8:25:7, 2:8:28:1,
2:8:28:3, 2:8:28:5, 2:8:28:8, 2:8:35:1, 2:8:35:4, 2:8:35:8, 2:8:36:2,
2:8:36:4, 2:8:38:1, 2:8:38:2, 2:8:39:1, 2:8:39:2, 2:8:39:5, 2:8:39:6,
2:10:1:4, 2:10:1:6, 2:10:1:8, 2:10:7:1, 2:10:7:2, 2:10:7:6, 2:10:7:7,
2:10:10:1, 2:10:10:3, 2:10:10:5, 2:10:11:1, 2:10:11:4, 2:10:11:8,
2:10:14:1, 2:10:14:3, 2:10:14:4, 2:10:14:6, 2:10:16:1, 2:10:16:2,
2:10:16:5, 2:10:16:6, 2:10:17:1, 2:10:17:4, 2:10:17:6, 2:10:26:1,
2:10:26:3, 2:10:26:5, 2:10:26:7, 2:10:28:4, 2:10:28:5, 2:10:29:5,
2:10:29:7, 2:10:30:3, 2:10:30:5, 2:10:31:2, 2:10:31:3, 2:10:31:6,
2:10:33:1, 2:10:33:2, 2:10:33:4, 2:10:33:5, 2:10:41:4, 2:10:41:7,
2:13:2:2, 2:13:2:4, 2:13:2:5, 2:13:4:3, 2:13:4:8, 2:13:6:1, 2:13:6:2,
2:13:6:4, 2:13:6:8, 2:13:8:3, 2:13:8:5, 2:13:8:7, 2:13:8:8, 2:13:10:5,
2:13:10:6, 2:13:13:3, 2:13:13:4, 2:13:16:3, 2:13:16:4, 2:13:16:7,
2:13:17:1, 2:13:17:2, 2:13:18:6, 2:13:18:8, 2:13:27:1, 2:13:27:2,
2:13:27:3, 2:13:27:5, 2:13:30:2, 2:13:30:7, 2:13:30:8, 2:13:31:3,
2:13:31:6, 2:13:31:8, 2:13:35:1, 2:13:35:4, 2:13:37:1, 2:13:37:6,
2:13:37:7, 2:13:37:8, 2:13:38:2, 2:13:38:5, 2:13:38:6, 2:13:39:5,
2:13:39:6, 2:17:1:2, 2:17:1:5, 2:17:7:2, 2:17:7:3, 2:17:7:6, 2:17:7:8,
2:17:9:1, 2:17:9:3, 2:17:9:8, 2:17:11:1, 2:17:11:2, 2:17:11:8,
2:17:13:3, 2:17:13:6, 2:17:13:7, 2:17:15:1, 2:17:15:2, 2:17:15:5,
2:17:15:7, 2:17:16:1, 2:17:16:2, 2:17:16:8, 2:17:17:1, 2:17:17:3,
2:17:17:8, 2:17:20:5, 2:17:20:6, 2:17:22:3, 2:17:22:8, 2:17:24:3,
2:17:24:6, 2:17:25:3, 2:17:25:6, 2:17:25:7, 2:17:27:1, 2:17:27:5,
2:17:27:8, 2:17:29:2, 2:17:29:3, 2:17:29:8, 2:17:30:3, 2:17:30:5,

TABLE 5a-continued

Exemplary Enumerated Compounds using Tables 1a, 2a, 3, and 4

| | | | | | | |
|---|---|---|---|---|---|---|
| 2:17:30:8, | 2:17:33:1, | 2:17:33:3, | 2:17:33:6, | 2:17:33:8, | 2:17:34:1, | |
| 2:17:34:3, | 2:17:34:4, | 2:17:34:7, | 2:17:35:1, | 2:17:35:4, | 2:17:35:7, | |
| 2:17:37:2, | 2:17:37:5, | 2:17:37:7, | 2:17:37:8, | 4:8:3:3, | 4:8:3:4, | 4:8:9:4, |
| 4:8:9:6, | 4:8:10:1, | 4:8:10:3, | 4:8:14:1, | 4:8:14:4, | 4:8:14:7, | 4:8:14:8, |
| 4:8:17:3, | 4:8:17:5, | 4:8:17:6, | 4:8:18:1, | 4:8:18:6, | 4:8:19:2, | 4:8:19:3, |
| 4:8:19:7, | 4:8:19:8, | 4:8:20:1, | 4:8:20:2, | 4:8:20:3, | 4:8:20:8, | 4:8:24:3, |
| 4:8:24:6, | 4:8:30:4, | 4:8:30:7, | 4:8:30:8, | 4:8:32:4, | 4:8:32:7, | 4:8:34:2, |
| 4:8:34:4, | 4:8:34:5, | 4:8:34:6, | 4:8:37:4, | 4:8:37:5, | 4:12:1:3, | 4:12:1:5, |
| 4:12:3:1, | 4:12:3:4, | 4:12:3:8, | 4:12:4:1, | 4:12:4:2, | 4:12:4:4, | 4:12:9:2, |
| 4:12:9:3, | 4:12:10:2, | 4:12:10:4, | 4:12:10:7, | 4:12:10:8, | 4:12:13:1, | |
| 4:12:13:3, | 4:12:13:4, | 4:12:13:8, | 4:12:26:1, | 4:12:26:2, | 4:12:26:5, | |
| 4:12:26:7, | 4:12:32:1, | 4:12:32:2, | 4:12:32:7, | 4:12:32:8, | 4:12:33:2, | |
| 4:12:33:5, | 4:12:40:3, | 4:12:40:5, | 5:7:1:6, | 5:7:1:8, | 5:7:2:1, | 5:7:2:4, |
| 5:7:6:3, | 5:7:6:5, | 5:7:6:6, | 5:7:6:8, | 5:7:7:1, | 5:7:7:7, | 5:7:7:8, |
| 5:7:10:1, | 5:7:10:3, | 5:7:10:6, | 5:7:12:3, | 5:7:12:7, | 5:7:13:1, | 5:7:13:2, |
| 5:7:13:4, | 5:7:14:3, | 5:7:14:7, | 5:7:15:1, | 5:7:15:6, | 5:7:15:8, | 5:7:16:1, |
| 5:7:16:4, | 5:7:16:5, | 5:7:20:1, | 5:7:20:2, | 5:7:20:5, | 5:7:20:6, | 5:7:21:3, |
| 5:7:21:6, | 5:7:21:8, | 5:7:23:1, | 5:7:23:6, | 5:7:23:8, | 5:7:24:1, | 5:7:24:2, |
| 5:7:24:5, | 5:7:24:7, | 5:7:25:2, | 5:7:25:5, | 5:7:25:7, | 5:7:27:1, | 5:7:27:3, |
| 5:7:27:4, | 5:7:27:6, | 5:7:28:3, | 5:7:28:4, | 5:7:28:5, | 5:7:28:6, | 5:7:34:2, |
| 5:7:34:4, | 5:7:34:7, | 5:7:34:8, | 5:7:35:1, | 5:7:35:4, | 5:7:35:5, | 5:7:35:7, |
| 5:7:36:1, | 5:7:36:2, | 5:7:36:6, | 5:7:36:8, | 5:10:1:5, | 5:10:1:6, | 5:10:1:7, |
| 5:10:3:3, | 5:10:3:8, | 5:10:7:1, | 5:10:7:3, | 5:10:7:7, | 5:10:8:2, | 5:10:8:8, |
| 5:10:21:3, | 5:10:21:6, | 5:10:21:7, | 5:10:24:2, | 5:10:24:7, | 5:10:24:8, | |
| 5:10:28:1, | 5:10:28:2, | 5:10:28:4, | 5:10:28:6, | 5:10:29:1, | 5:10:29:3, | |
| 5:10:29:4, | 5:10:29:6, | 5:10:33:4, | 5:10:33:5, | 5:10:40:2, | 5:10:40:5, | |
| 5:10:40:6, | 5:10:40:7, | 5:12:5:2, | 5:12:5:3, | 5:12:5:4, | 5:12:5:7, | |
| 5:12:16:4, | 5:12:16:6, | 5:12:16:7, | 5:12:23:1, | 5:12:23:2, | 5:12:23:3, | |
| 5:12:23:7, | 5:12:30:2, | 5:12:30:5, | 5:12:30:6, | 5:12:31:1, | 5:12:31:4, | |
| 5:12:31:5, | 5:12:31:7, | 5:12:32:3, | 5:12:32:5, | 5:12:32:8, | 5:12:33:5, | |
| 5:12:33:6, | 5:12:34:1, | 5:12:34:2, | 5:12:34:3, | 5:12:34:5, | 5:12:35:2, | |
| 5:12:35:3, | 5:12:35:5, | 5:12:35:6, | 5:12:38:2, | 5:12:38:5, | 5:12:38:6, | |
| 5:12:38:8, | 5:13:2:2, | 5:13:2:5, | 5:13:2:7, | 5:13:3:1, | 5:13:3:2, | 5:13:3:7, |
| 5:13:3:8, | 5:13:8:1, | 5:13:8:5, | 5:13:8:7, | 5:13:9:1, | 5:13:9:2, | 5:13:9:6, |
| 5:13:9:7, | 5:13:10:5, | 5:13:10:7, | 5:13:20:1, | 5:13:20:6, | 5:13:21:3, | |
| 5:13:21:8, | 5:13:23:4, | 5:13:23:6, | 5:13:23:8, | 5:13:25:3, | 5:13:25:4, | |
| 5:13:30:3, | 5:13:30:8, | 5:13:32:2, | 5:13:32:4, | 5:13:32:5, | 5:13:32:7, | |
| 5:13:33:3, | 5:13:33:4, | 5:13:33:5, | 5:13:33:8, | 5:13:34:1, | 5:13:34:6, | |
| 5:13:35:3, | 5:13:35:6, | 5:13:37:2, | 5:13:37:6, | 5:13:40:3, | 5:13:40:4, | |
| 5:13:40:8, | 5:16:4:3, | 5:16:4:6, | 5:16:5:3, | 5:16:5:5, | 5:16:5:7, | 5:16:5:8, |
| 5:16:8:3, | 5:16:8:7, | 5:16:14:3, | 5:16:14:7, | 5:16:16:3, | 5:16:16:5, | |
| 5:16:23:1, | 5:16:23:2, | 5:16:23:5, | 5:16:23:6, | 5:16:27:4, | 5:16:27:5, | |
| 5:16:27:7, | 5:16:29:1, | 5:16:29:2, | 5:16:29:3, | 5:16:29:5, | 5:16:30:5, | |
| 5:16:30:7, | 5:16:31:1, | 5:16:31:2, | 5:16:31:4, | 5:16:31:5, | 5:16:32:3, | |
| 5:16:32:5, | 5:16:33:4, | 5:16:33:5, | 5:16:33:6, | 5:16:33:8, | 5:16:36:1, | |
| 5:16:36:3, | 5:16:36:6, | 5:16:38:2, | 5:16:38:3, | 5:16:38:8, | 6:11:3:7, | |
| 6:11:3:8, | 6:11:4:2, | 6:11:4:5, | 6:11:4:7, | 6:11:6:2, | 6:11:6:5, | 6:11:10:3, |
| 6:11:10:6, | 6:11:10:7, | 6:11:13:1, | 6:11:13:4, | 6:11:13:6, | 6:11:14:1, | |
| 6:11:14:4, | 6:11:14:6, | 6:11:15:2, | 6:11:15:4, | 6:11:15:6, | 6:11:19:1, | |
| 6:11:19:4, | 6:11:19:5, | 6:11:19:8, | 6:11:21:1, | 6:11:21:6, | 6:11:21:7, | |
| 6:11:23:1, | 6:11:23:2, | 6:11:23:5, | 6:11:30:2, | 6:11:30:3, | 6:11:30:8, | |
| 6:11:32:3, | 6:11:32:4, | 6:11:35:2, | 6:11:35:3, | 6:11:35:4, | 6:11:35:7, | |
| 6:11:36:2, | 6:11:36:4, | 6:11:36:5, | 6:11:36:8, | 6:11:40:1, | 6:11:40:2, | |
| 6:11:40:4, | 6:11:40:8, | 6:11:41:2, | 6:11:41:8, | 6:14:2:4, | 6:14:2:8, | |
| 6:14:4:1, | 6:14:4:4, | 6:14:4:6, | 6:14:7:1, | 6:14:7:3, | 6:14:7:5, | 6:14:7:8, |
| 6:14:11:4, | 6:14:11:8, | 6:14:13:3, | 6:14:13:6, | 6:14:13:7, | 6:14:15:4, | |
| 6:14:15:5, | 6:14:15:6, | 6:14:15:7, | 6:14:16:4, | 6:14:16:6, | 6:14:16:7, | |
| 6:14:16:8, | 6:14:19:1, | 6:14:19:2, | 6:14:19:3, | 6:14:19:7, | 6:14:20:2, | |
| 6:14:20:4, | 6:14:20:6, | 6:14:20:7, | 6:14:22:1, | 6:14:22:7, | 6:14:22:8, | |
| 6:14:24:4, | 6:14:24:5, | 6:14:24:7, | 6:14:24:8, | 6:14:26:3, | 6:14:26:4, | |
| 6:14:29:4, | 6:14:29:7, | 6:14:30:2, | 6:14:30:5, | 6:14:30:8, | 6:14:34:2, | |
| 6:14:34:3, | 6:14:34:5, | 6:14:34:6, | 6:17:1:3, | 6:17:1:4, | 6:17:1:6, | |
| 6:17:1:8, | 6:17:2:6, | 6:17:2:7, | 6:17:2:8, | 6:17:8:2, | 6:17:8:3, | 6:17:8:7, |
| 6:17:8:8, | 6:17:12:2, | 6:17:12:5, | 6:17:12:6, | 6:17:12:7, | 6:17:13:1, | |
| 6:17:13:5, | 6:17:13:7, | 6:17:13:8, | 6:17:15:5, | 6:17:15:7, | 6:17:15:8, | |
| 6:17:18:6, | 6:17:18:7, | 6:17:19:2, | 6:17:19:8, | 6:17:20:4, | 6:17:20:7, | |
| 6:17:20:8, | 6:17:22:1, | 6:17:22:2, | 6:17:22:5, | 6:17:23:3, | 6:17:23:7, | |
| 6:17:23:8, | 6:17:24:3, | 6:17:24:4, | 6:17:24:5, | 6:17:24:6, | 6:17:27:5, | |
| 6:17:27:7, | 6:17:30:1, | 6:17:30:2, | 6:17:31:1, | 6:17:31:5, | 6:17:31:7, | |
| 6:17:33:4, | 6:17:33:7, | 6:17:36:1, | 6:17:36:3, | 6:17:36:4, | 6:17:36:7, | |
| 6:17:37:2, | 6:17:37:3, | 6:17:37:5, | 6:17:39:1, | 6:17:39:4, | 6:17:39:6, | |
| 6:17:41:5, | 6:17:41:6, | 6:17:41:7, | 9:7:2:1, | 9:7:2:4, | 9:7:2:7, | 9:7:7:1, |
| 9:7:7:5, | 9:7:8:1, | 9:7:8:8, | 9:7:11:2, | 9:7:11:5, | 9:7:11:7, | 9:7:13:1, |
| 9:7:13:3, | 9:7:13:4, | 9:7:13:7, | 9:7:14:1, | 9:7:14:2, | 9:7:14:3, | 9:7:14:5, |
| 9:7:18:2, | 9:7:18:3, | 9:7:18:5, | 9:7:18:7, | 9:7:19:1, | 9:7:19:6, | 9:7:19:7, |
| 9:7:24:2, | 9:7:24:3, | 9:7:24:5, | 9:7:24:6, | 9:7:25:1, | 9:7:25:8, | 9:7:27:5, |
| 9:7:27:6, | 9:7:27:7, | 9:7:28:3, | 9:7:28:5, | 9:7:28:7, | 9:7:31:3, | 9:7:31:5, |

TABLE 5a-continued

Exemplary Enumerated Compounds using Tables 1a, 2a, 3, and 4

| | | | | | | |
|---|---|---|---|---|---|---|
| 9:7:31:6, | 9:7:31:8, | 9:7:34:2, | 9:7:34:4, | 9:7:34:5, | 9:7:35:3, | 9:7:35:4, |
| 9:7:35:5, | 9:7:35:7, | 9:7:36:3, | 9:7:36:6, | 9:7:36:7, | 9:7:36:8, | 9:7:38:1, |
| 9:7:38:5, | 9:7:38:6, | 9:7:40:3, | 9:7:40:4, | 9:7:40:6, | 9:7:41:5, | 9:7:41:8, |
| 9:16:1:5, | 9:16:1:7, | 9:16:2:2, | 9:16:2:5, | 9:16:2:6, | 9:16:2:7, | 9:16:9:4, |
| 9:16:9:8, | 9:16:11:2, | 9:16:11:5, | 9:16:11:7, | 9:16:12:1, | 9:16:12:5, | |
| 9:16:12:8, | 9:16:16:1, | 9:16:16:4, | 9:16:16:5, | 9:16:21:1, | 9:16:21:3, | |
| 9:16:22:5, | 9:16:22:6, | 9:16:22:7, | 9:16:25:1, | 9:16:25:6, | 9:16:30:1, | |
| 9:16:30:5, | 9:16:30:7, | 9:16:30:8, | 9:16:33:1, | 9:16:33:3, | 9:16:33:5, | |
| 9:16:34:6, | 9:16:34:8, | 9:16:35:5, | 9:16:35:7, | 9:16:37:1, | 9:16:37:2, | |
| 9:16:40:3, | 9:16:40:5, | 9:16:40:7, | 11:7:5:4, | 11:7:5:5, | 11:7:5:6, | |
| 11:7:7:2, | 11:7:7:4, | 11:7:7:6, | 11:7:10:7, | 11:7:10:8, | 11:7:15:4, | |
| 11:7:15:7, | 11:7:16:1, | 11:7:16:2, | 11:7:16:5, | 11:7:16:7, | 11:7:18:1, | |
| 11:7:18:2, | 11:7:18:6, | 11:7:18:7, | 11:7:21:3, | 11:7:21:7, | 11:7:27:2, | |
| 11:7:27:4, | 11:7:28:1, | 11:7:28:7, | 11:7:30:1, | 11:7:30:3, | 11:7:36:1, | |
| 11:7:36:3, | 11:7:36:4, | 11:7:36:7, | 11:7:37:1, | 11:7:37:7, | 11:9:4:2, | |
| 11:9:4:3, | 11:9:8:3, | 11:9:8:7, | 11:9:8:8, | 11:9:9:1, | 11:9:9:4, | 11:9:9:7, |
| 11:9:11:3, | 11:9:11:4, | 11:9:11:5, | 11:9:11:8, | 11:9:15:4, | 11:9:15:5, | |
| 11:9:17:1, | 11:9:17:3, | 11:9:21:1, | 11:9:21:4, | 11:9:21:6, | 11:9:21:8, | |
| 11:9:32:2, | 11:9:32:3, | 11:9:32:4, | 11:9:32:8, | 11:9:33:3, | 11:9:33:4, | |
| 11:9:33:7, | 11:9:33:8, | 11:9:35:4, | 11:9:35:5, | 11:9:36:3, | 11:9:36:7, | |
| 11:9:40:3, | 11:9:40:6, | 11:9:40:7, | 11:9:41:1, | 11:9:41:2, | 11:9:41:5, | |
| 11:9:41:8, | 11:14:2:1, | 11:14:2:2, | 11:14:6:2, | 11:14:6:5, | 11:14:8:5, | |
| 11:14:8:7, | 11:14:12:2, | 11:14:12:7, | 11:14:13:3, | 11:14:13:6, | 11:14:13:8, | |
| 11:14:16:3, | 11:14:16:6, | 11:14:16:7, | 11:14:18:7, | 11:14:18:8, | 11:14:29:3, | |
| 11:14:29:4, | 11:14:29:5, | 11:14:29:8, | 11:14:32:3, | 11:14:32:5, | 11:14:32:7, | |
| 11:14:32:8, | 11:14:36:1, | 11:14:36:5, | 11:14:36:6, | 11:14:36:8, | 11:16:3:1, | |
| 11:16:3:5, | 11:16:5:3, | 11:16:5:5, | 11:16:11:1, | 11:16:11:4, | 11:16:16:2, | |
| 11:16:16:3, | 11:16:16:6, | 11:16:16:7, | 11:16:19:1, | 11:16:19:3, | 11:16:19:6, | |
| 11:16:19:7, | 11:16:25:1, | 11:16:25:4, | 11:16:27:4, | 11:16:27:7, | 11:16:27:8, | |
| 11:16:36:3, | 11:16:36:4, | 11:16:36:7, | 15:10:5:3, | 15:10:5:5, | 15:10:21:2, | |
| 15:10:21:8, | 15:10:23:1, | 15:10:23:4, | 15:10:23:8, | 15:10:24:1, | 15:10:24:2, | |
| 15:10:24:6, | 15:10:25:2, | 15:10:25:5, | 15:10:26:1, | 15:10:26:3, | 15:10:26:6, | |
| 15:10:26:8, | 15:10:29:1, | 15:10:29:2, | 15:10:29:5, | 15:10:32:1, | 15:10:32:5, | |
| 15:10:32:8, | 15:10:38:1, | 15:10:38:3, | 15:10:38:5, | 15:10:38:8, | 15:10:40:1, | |
| 15:10:40:4, | 15:10:40:5, | 15:13:1:2, | 15:13:1:5, | 15:13:2:1, | 15:13:2:4, | |
| 15:13:2:6, | 15:13:5:4, | 15:13:5:6, | 15:13:9:2, | 15:13:9:5, | 15:13:9:7, | |
| 15:13:9:8, | 15:13:16:3, | 15:13:16:7, | 15:13:27:3, | 15:13:27:5, | 15:13:27:7, | |
| 15:13:36:2, | 15:13:36:3, | 15:13:36:6, | 15:13:39:1, | 15:13:39:4, | 15:13:41:1, | |
| 15:13:41:6, | 15:15:4:1, | 15:15:4:2, | 15:15:4:7, | 15:15:5:2, | 15:15:5:5, | |
| 15:15:5:7, | 15:15:5:8, | 15:15:9:4, | 15:15:9:5, | 15:15:9:6, | 15:15:11:5, | |
| 15:15:11:6, | 15:15:11:8, | 15:15:13:2, | 15:15:13:3, | 15:15:13:6, | 15:15:13:7, | |
| 15:15:14:2, | 15:15:14:3, | 15:15:14:4, | 15:15:14:8, | 15:15:16:2, | 15:15:16:6, | |
| 15:15:16:7, | 15:15:16:8, | 15:15:17:4, | 15:15:17:6, | 15:15:17:7, | 15:15:17:8, | |
| 15:15:18:2, | 15:15:18:5, | 15:15:18:8, | 15:15:20:1, | 15:15:20:2, | 15:15:20:4, | |
| 15:15:25:3, | 15:15:25:7, | 15:15:40:2, | 15:15:40:8, | 19:7:3:2, | 19:7:3:4, | |
| 19:7:3:5, | 19:7:3:7, | 19:7:8:5, | 19:7:8:7, | 19:7:9:2, | 19:7:9:3, | 19:7:9:7, |
| 19:7:10:1, | 19:7:10:4, | 19:7:10:6, | 19:7:10:8, | 19:7:11:3, | 19:7:11:7, | |
| 19:7:11:8, | 19:7:13:2, | 19:7:13:4, | 19:7:19:4, | 19:7:19:5, | 19:7:19:6, | |
| 19:7:19:8, | 19:7:22:1, | 19:7:22:4, | 19:7:22:5, | 19:7:22:6, | 19:7:24:6, | |
| 19:7:24:7, | 19:7:24:8, | 19:7:25:3, | 19:7:25:4, | 19:7:32:2, | 19:7:32:4, | |
| 19:7:32:6, | 19:7:32:7, | 19:7:34:4, | 19:7:34:8, | 19:7:35:7, | 19:7:35:8, | |
| 19:8:1:3, | 19:8:1:6, | 19:8:3:4, | 19:8:3:6, | 19:8:3:7, | 19:8:9:2, | 19:8:9:5, |
| 19:8:9:7, | 19:8:9:8, | 19:8:11:3, | 19:8:11:4, | 19:8:11:6, | 19:8:11:8, | |
| 19:8:12:2, | 19:8:12:3, | 19:8:12:7, | 19:8:14:5, | 19:8:14:8, | 19:8:16:1, | |
| 19:8:16:2, | 19:8:16:4, | 19:8:16:8, | 19:8:19:2, | 19:8:19:3, | 19:8:22:1, | |
| 19:8:22:3, | 19:8:23:1, | 19:8:23:3, | 19:8:23:4, | 19:8:23:7, | 19:8:24:4, | |
| 19:8:24:5, | 19:8:24:7, | 19:8:25:1, | 19:8:25:3, | 19:8:27:1, | 19:8:27:3, | |
| 19:8:27:7, | 19:8:28:2, | 19:8:28:4, | 19:8:28:6, | 19:8:28:8, | 19:8:33:1, | |
| 19:8:33:3, | 19:8:33:7, | 19:8:34:2, | 19:8:34:5, | 19:8:34:7, | 19:8:34:8, | |
| 19:8:35:1, | 19:8:35:5, | 19:8:37:2, | 19:8:37:5, | 19:8:37:8, | 19:8:40:1, | |
| 19:8:40:3, | 19:14:1:1, | 19:14:1:5, | 19:14:3:2, | 19:14:3:3, | 19:14:3:5, | |
| 19:14:3:6, | 19:14:6:7, | 19:14:6:8, | 19:14:13:6, | 19:14:13:7, | 19:14:13:8, | |
| 19:14:14:1, | 19:14:14:3, | 19:14:14:5, | 19:14:15:3, | 19:14:15:4, | 19:14:15:6, | |
| 19:14:15:8, | 19:14:16:4, | 19:14:16:8, | 19:14:17:4, | 19:14:17:6, | 19:14:37:2, | |
| 19:14:37:4, | 19:14:37:5, | 19:14:37:7, | 19:14:40:1, | 19:14:40:3, | 19:14:40:6, | |
| 19:14:40:8, | 21:8:4:3, | 21:8:4:8, | 21:8:7:1, | 21:8:7:3, | 21:8:7:5, | 21:8:7:6, |
| 21:8:10:3, | 21:8:10:8, | 21:8:11:4, | 21:8:11:5, | 21:8:11:7, | 21:8:11:8, | |
| 21:8:12:2, | 21:8:12:3, | 21:8:12:4, | 21:8:12:8, | 21:8:13:5, | 21:8:13:6, | |
| 21:8:13:7, | 21:8:17:2, | 21:8:17:6, | 21:8:17:7, | 21:8:19:1, | 21:8:19:3, | |
| 21:8:21:1, | 21:8:21:4, | 21:8:23:3, | 21:8:23:4, | 21:8:23:7, | 21:8:24:1, | |
| 21:8:24:6, | 21:8:27:3, | 21:8:27:4, | 21:8:27:5, | 21:8:27:6, | 21:8:28:1, | |
| 21:8:28:5, | 21:8:28:7, | 21:8:28:8, | 21:8:33:3, | 21:8:33:6, | 21:8:33:8, | |
| 21:8:36:2, | 21:8:36:8, | 21:8:38:2, | 21:8:38:4, | 21:8:38:8, | 21:8:40:1, | |
| 21:8:40:6, | 21:13:2:1, | 21:13:2:3, | 21:13:2:7, | 21:13:9:3, | 21:13:9:8, | |
| 21:13:12:2, | 21:13:12:5, | 21:13:12:6, | 21:13:14:7, | 21:13:14:8, | 21:13:20:3, | |
| 21:13:20:4, | 21:13:20:6, | 21:13:29:1, | 21:13:29:4, | 21:13:29:7, | 21:13:32:1, | |
| 21:13:32:3, | 21:13:32:4, | 21:13:32:7, | 21:13:40:3, | 21:13:40:6, | 21:7:2:1, | |

TABLE 5a-continued

Exemplary Enumerated Compounds using Tables 1a, 2a, 3, and 4

21:7:2:4, 21:7:7:2, 21:7:7:4, 21:7:7:5, 21:7:7:8, 21:7:8:1, 21:7:8:4,
21:7:16:1, 21:7:16:3, 21:7:16:4, 21:7:16:7, 21:7:28:1, 21:7:28:8,
21:7:30:3, 21:7:30:4, 21:7:32:2, 21:7:32:3, 21:7:32:6, 21:7:32:8,
21:7:41:3, 21:7:41:4, 22:10:7:2, 22:10:7:4, 22:10:7:6, 22:10:7:8,
22:10:20:1, 22:10:20:2, 22:10:20:6, 22:10:20:8, 22:10:22:3, 22:10:22:5,
22:10:24:1, 22:10:24:4, 22:10:24:8, 22:10:34:2, 22:10:34:5, 22:10:34:7,
22:10:37:4, 22:10:37:7, 22:10:38:1, 22:10:38:4, 22:10:38:7, 22:10:41:5,
22:10:41:6, 22:11:6:4, 22:11:6:6, 22:11:11:4, 22:11:11:8, 22:11:12:4,
22:11:12:7, 22:11:12:8, 22:11:21:2, 22:11:21:3, 22:11:21:4, 22:11:21:8,
22:11:26:1, 22:11:26:2, 22:11:26:8, 22:11:28:4, 22:11:28:5, 22:11:28:7,
22:11:30:1, 22:11:30:3, 22:11:30:4, 22:11:30:5, 22:11:34:1, 22:11:34:2,
22:12:1:1, 22:12:1:4, 22:12:1:5, 22:12:3:2, 22:12:3:4, 22:12:3:5,
22:12:4:1, 22:12:4:8, 22:12:5:1, 22:12:5:3, 22:12:5:7, 22:12:6:2,
22:12:6:3, 22:12:6:4, 22:12:6:8, 22:12:8:1, 22:12:8:2, 22:12:12:2,
22:12:12:5, 22:12:12:8, 22:12:15:4, 22:12:15:6, 22:12:15:8, 22:12:16:4,
22:12:16:7, 22:12:16:8, 22:12:17:6, 22:12:17:7, 22:12:26:2, 22:12:26:3,
22:12:32:5, 22:12:32:6, 22:12:34:2, 22:12:34:4, 22:12:34:6, 22:12:35:1,
22:12:35:2, 22:12:35:6, 22:12:35:7, 22:12:36:2, 22:12:36:3, 22:12:36:5,
22:12:37:7, 22:12:37:8, 22:12:39:3, 22:12:39:5, 22:14:4:4, 22:14:4:6,
22:14:4:7, 22:14:9:1, 22:14:9:2, 22:14:9:4, 22:14:11:2, 22:14:11:4,
22:14:11:5, 22:14:11:6, 22:14:14:2, 22:14:14:3, 22:14:14:5, 22:14:19:1,
22:14:19:3, 22:14:19:4, 22:14:19:8, 22:14:24:1, 22:14:24:4, 22:14:24:6,
22:14:27:3, 22:14:27:4, 22:14:27:6, 22:14:28:2, 22:14:28:3, 22:14:28:5,
22:14:33:1, 22:14:33:3, 22:14:33:4, 22:14:33:6, 22:14:34:1, 22:14:34:4,
22:14:35:1, 22:14:35:2, 22:14:35:7, 22:14:35:8, 22:14:36:1, 22:14:36:5,
22:14:36:8, 22:14:38:1, 22:14:38:2, 22:14:38:6, 22:14:38:7, 46:10:2:1,
46:10:2:6, 46:10:18:2, 46:10:18:6, 46:10:18:7, 46:10:19:1, 46:10:19:7,
46:10:19:8, 46:10:22:2, 46:10:22:3, 46:10:25:1, 46:10:25:2, 46:10:25:6,
46:10:25:7, 46:10:26:4, 46:10:26:5, 46:10:26:6, 46:10:26:8, 46:10:33:2,
46:10:33:8, 46:10:34:1, 46:10:34:2, 46:10:34:5, 46:10:34:6, 46:10:36:3,
46:10:36:4, 46:10:36:6, 46:10:36:7, 46:13:2:2, 46:13:2:3, 46:13:2:6,
46:13:2:7, 46:13:3:1, 46:13:3:2, 46:13:3:4, 46:13:6:2, 46:13:6:3,
46:13:6:5, 46:13:6:8, 46:13:7:1, 46:13:7:2, 46:13:7:3, 46:13:7:8,
46:13:10:1, 46:13:10:2, 46:13:10:3, 46:13:10:4, 46:13:11:1, 46:13:11:2,
46:13:11:5, 46:13:12:1, 46:13:12:3, 46:13:13:4, 46:13:13:8, 46:13:14:3,
46:13:14:7, 46:13:15:1, 46:13:15:3, 46:13:16:3, 46:13:16:5, 46:13:16:7,
46:13:16:8, 46:13:17:3, 46:13:17:5, 46:13:19:5, 46:13:19:7, 46:13:23:2,
46:13:23:4, 46:13:23:6, 46:13:23:8, 46:13:24:2, 46:13:24:5, 46:13:24:6,
46:13:29:1, 46:13:29:2, 46:13:29:4, 46:13:30:1, 46:13:30:4, 46:13:30:7,
46:13:30:8, 46:13:31:4, 46:13:31:7, 46:13:38:2, 46:13:38:5, 46:13:38:7,
46:13:38:8, 46:13:39:1, 46:13:39:4, 46:13:39:5, 46:14:5:4, 46:14:5:5,
46:14:10:2, 46:14:10:3, 46:14:11:6, 46:14:11:8, 46:14:12:1, 46:14:12:2,
46:14:12:4, 46:14:14:3, 46:14:14:4, 46:14:18:1, 46:14:18:3, 46:14:18:5,
46:14:18:8, 46:14:19:2, 46:14:19:4, 46:14:19:8, 46:14:22:4, 46:14:22:8,
46:14:24:2, 46:14:24:6, 46:14:24:8, 46:14:37:6, 46:14:37:7, 46:14:37:8,
51:8:3:2, 51:8:3:4, 51:8:3:5, 51:8:3:8, 51:8:9:4, 51:8:9:5, 51:8:9:6,
51:8:9:8, 51:8:12:5, 51:8:12:6, 51:8:12:8, 51:8:18:2, 51:8:18:3,
51:8:27:7, 51:8:27:8, 51:8:31:2, 51:8:31:7, 51:8:35:2, 51:8:35:6,
51:8:35:7, 51:8:41:3, 51:8:41:5, 51:12:1:3, 51:12:1:7, 51:12:1:8,
51:12:7:1, 51:12:7:6, 51:12:10:4, 51:12:10:7, 51:12:10:8, 51:12:13:3,
51:12:13:5, 51:12:22:3, 51:12:22:4, 51:12:22:5, 51:12:22:6, 51:12:23:1,
51:12:23:2, 51:12:23:4, 51:12:23:5, 51:12:26:1, 51:12:26:2, 51:12:26:7,
51:12:27:5, 51:12:27:8, 51:12:30:2, 51:12:30:6, 51:12:30:7, 51:12:30:8,
51:12:34:1, 51:12:34:5, 51:12:34:6, 51:12:41:5, 51:12:41:7, 51:14:1:2,
51:14:1:5, 51:14:1:7, 51:14:3:3, 51:14:3:4, 51:14:3:5, 51:14:3:8,
51:14:6:1, 51:14:6:2, 51:14:6:7, 51:14:9:4, 51:14:9:7, 51:14:18:5,
51:14:18:6, 51:14:18:8, 51:14:22:3, 51:14:22:4, 51:14:22:5, 51:14:22:6,
51:14:24:6, 51:14:24:7, 51:14:24:8, 51:14:40:3, 51:14:40:4, 51:14:40:5,
51:15:2:1, 51:15:2:2, 51:15:2:3, 51:15:2:8, 51:15:6:7, 51:15:6:8,
51:15:11:5, 51:15:11:7, 51:15:13:6, 51:15:13:7, 51:15:17:2, 51:15:17:5,
51:15:17:8, 51:15:25:1, 51:15:25:2, 51:15:31:1, 51:15:31:2, 51:15:31:4,
51:15:31:6, 51:15:32:5, 51:15:32:6, 51:15:32:7, 51:15:32:8, 51:15:34:3,
51:15:34:4, 51:15:34:5, 51:15:35:1, 51:15:35:7, 51:15:35:8, 51:15:37:5,
51:15:37:6, 51:17:1:4, 51:17:1:6, 51:17:1:7, 51:17:1:8, 51:17:2:1,
51:17:2:3, 51:17:2:8, 51:17:3:4, 51:17:3:7, 51:17:4:1, 51:17:4:2,
51:17:6:2, 51:17:6:4, 51:17:6:7, 51:17:8:6, 51:17:8:8, 51:17:9:1,
51:17:9:2, 51:17:9:6, 51:17:9:7, 51:17:13:5, 51:17:13:6, 51:17:14:1,
51:17:14:5, 51:17:15:2, 51:17:15:4, 51:17:15:7, 51:17:17:1, 51:17:17:5,
51:17:18:1, 51:17:18:4, 51:17:18:6, 51:17:19:1, 51:17:19:4, 51:17:19:6,
51:17:19:8, 51:17:22:1, 51:17:22:2, 51:17:22:5, 51:17:22:6, 51:17:27:1,
51:17:27:3, 51:17:27:6, 51:17:28:1, 51:17:28:4, 51:17:28:7, 51:17:29:4,
51:17:29:6, 51:17:31:1, 51:17:31:4, 51:17:31:5, 51:17:31:6, 51:17:35:2,
51:17:35:3, 52:9:7:2, 52:9:7:3, 52:9:7:5, 52:9:9:3, 52:9:9:7,
52:9:11:1, 52:9:11:7, 52:9:16:5, 52:9:16:6, 52:9:18:3, 52:9:18:5,
52:9:18:6, 52:9:18:8, 52:9:19:3, 52:9:19:6, 52:9:19:7, 52:9:20:2,
52:9:20:5, 52:9:20:7, 52:9:23:4, 52:9:23:6, 52:9:24:5, 52:9:24:6,
52:9:27:1, 52:9:27:3, 52:9:27:4, 52:9:27:7, 52:9:31:2, 52:9:31:7,

TABLE 5a-continued

Exemplary Enumerated Compounds using Tables 1a, 2a, 3, and 4

52:9:32:2, 52:9:32:5, 52:9:32:7, 52:9:33:4, 52:9:33:7, 52:9:35:1,
52:9:35:2, 52:9:35:6, 52:9:35:7, 52:10:1:1, 52:10:1:4, 52:10:1:6,
52:10:1:7, 52:10:5:4, 52:10:5:6, 52:10:7:2, 52:10:7:6, 52:10:7:8,
52:10:8:2, 52:10:8:5, 52:10:8:7, 52:10:8:8, 52:10:11:5, 52:10:11:7,
52:10:13:3, 52:10:13:4, 52:10:13:6, 52:10:13:7, 52:10:16:1, 52:10:16:4,
52:10:16:5, 52:10:17:1, 52:10:17:4, 52:10:18:1, 52:10:18:3, 52:10:18:4,
52:10:28:3, 52:10:28:4, 52:10:30:3, 52:10:30:6, 52:10:30:7, 52:10:30:8,
52:10:33:3, 52:10:33:4, 52:10:33:6, 52:10:35:2, 52:10:35:3, 52:10:35:8,
52:13:1:1, 52:13:1:3, 52:13:1:4, 52:13:1:7, 52:13:2:2, 52:13:2:8,
52:13:3:2, 52:13:3:6, 52:13:3:7, 52:13:3:8, 52:13:5:2, 52:13:5:3,
52:13:5:4, 52:13:5:7, 52:13:6:1, 52:13:6:6, 52:13:7:4, 52:13:7:6,
52:13:12:3, 52:13:12:6, 52:13:12:7, 52:13:14:1, 52:13:14:5, 52:13:16:4,
52:13:16:5, 52:13:16:8, 52:13:18:1, 52:13:18:4, 52:13:18:8, 52:13:20:2,
52:13:20:3, 52:13:20:8, 52:13:23:3, 52:13:23:4, 52:13:23:5, 52:13:25:3,
52:13:25:4, 52:13:25:5, 52:13:26:3, 52:13:26:6, 52:13:26:8, 52:13:32:1,
52:13:32:2, 52:13:32:3, 52:13:32:6, 52:13:33:2, 52:13:33:4, 52:13:34:1,
52:13:34:4, 52:13:34:6, 52:13:36:2, 52:13:36:6, 52:13:40:2, 52:13:40:3,
52:13:40:5, 52:13:40:7, 52:15:1:2, 52:15:1:3, 52:15:3:3, 52:15:3:7,
52:15:4:3, 52:15:4:6, 52:15:4:7, 52:15:4:8, 52:15:6:4, 52:15:6:5,
52:15:6:6, 52:15:6:7, 52:15:8:4, 52:15:8:5, 52:15:9:1, 52:15:9:5,
52:15:9:7, 52:15:9:8, 52:15:10:1, 52:15:10:7, 52:15:12:1, 52:15:12:7,
52:15:16:1, 52:15:16:4, 52:15:16:8, 52:15:17:2, 52:15:17:3, 52:15:17:4,
52:15:17:5, 52:15:18:4, 52:15:18:6, 52:15:22:3, 52:15:22:5, 52:15:22:7,
52:15:25:4, 52:15:25:5, 52:15:25:8, 52:15:26:1, 52:15:26:4, 52:15:26:5,
52:15:27:1, 52:15:27:3, 52:15:27:4, 52:15:27:6, 52:15:32:1, 52:15:32:3,
52:15:32:8, 52:15:41:1, 52:15:41:2, 52:15:41:3, 69:9:1:2, 69:9:1:3,
69:9:1:7, 69:9:5:1, 69:9:5:3, 69:9:5:7, 69:9:8:2, 69:9:8:6, 69:9:11:3,
69:9:11:4, 69:9:11:5, 69:9:15:2, 69:9:15:4, 69:9:16:1, 69:9:16:5,
69:9:16:6, 69:9:22:2, 69:9:22:5, 69:9:22:6, 69:9:22:8, 69:9:24:3,
69:9:24:5, 69:9:24:7, 69:9:24:8, 69:9:27:2, 69:9:27:3, 69:9:27:8,
69:9:28:2, 69:9:28:3, 69:9:28:5, 69:9:28:8, 69:9:30:1, 69:9:30:4,
69:9:31:1, 69:9:31:4, 69:9:33:5, 69:9:33:6, 69:9:33:8, 69:9:34:2,
69:9:34:3, 69:9:38:1, 69:9:38:5, 69:9:38:6, 69:9:38:8, 69:14:2:3,
69:14:2:7, 69:14:3:2, 69:14:3:6, 69:14:10:2, 69:14:10:8, 69:14:13:2,
69:14:13:3, 69:14:13:7, 69:14:22:1, 69:14:22:6, 69:14:25:2, 69:14:25:8,
69:14:26:1, 69:14:26:3, 69:14:26:6, 69:14:26:7, 69:14:29:3, 69:14:29:5,
69:14:29:7, 69:14:32:1, 69:14:32:2, 69:14:32:4, 69:14:32:7, 69:14:39:1,
69:14:39:5, 69:14:39:6, 69:15:6:4, 69:15:6:6, 69:14:6:7, 69:14:6:8,
69:15:8:2, 69:14:8:6, 69:15:8:8, 69:15:11:2, 69:15:11:6, 69:15:12:2,
69:15:12:4, 69:14:12:5, 69:15:20:2, 69:15:20:4, 69:15:21:1, 69:15:21:4,
69:15:21:8, 69:14:30:1, 69:15:30:5, 69:15:30:7, 69:15:32:3, 69:15:32:4,
69:15:32:6, 69:14:34:1, 69:15:34:3, 69:15:34:8, 69:15:39:3, 69:15:39:6,
69:15:40:1, 69:14:40:4, 69:15:40:6, 69:15:40:8, 69:16:1:1, 69:16:1:2,
69:16:1:6, 69:16:1:7, 69:16:2:1, 69:16:2:5, 69:16:6:3, 69:16:6:7,
69:16:8:1, 69:16:8:5, 69:16:8:6, 69:16:10:1, 69:16:10:3, 69:16:10:5,
69:16:10:8, 69:16:11:1, 69:16:11:2, 69:16:13:2, 69:16:13:4, 69:16:13:6,
69:16:15:6, 69:16:15:7, 69:16:15:8, 69:16:21:2, 69:16:21:6, 69:16:21:8,
69:16:24:5, 69:16:24:7, 69:16:25:1, 69:16:25:4, 69:16:25:6, 69:16:25:8,
69:16:26:2, 69:16:26:3, 69:16:26:4, 69:16:26:5, 69:16:27:4, 69:16:27:7,
69:16:28:1, 69:16:28:3, 69:16:29:6, 69:16:29:7, 69:16:29:8, 69:16:35:1,
69:16:35:2, 69:16:35:5, 69:16:35:7, 69:16:36:2, 69:16:36:3, 69:16:36:5,
69:16:39:1, 69:16:39:2, 69:16:39:5, 69:16:39:6, 69:16:40:2, 69:16:40:6,
69:16:40:8, 82:7:2:6, 82:7:2:8, 82:7:4:1, 82:7:4:3, 82:7:4:7, 82:7:4:8,
82:7:5:2, 82:7:5:4, 82:7:5:7, 82:7:8:3, 82:7:8:6, 82:7:11:1, 82:7:11:7,
82:7:12:1, 82:7:12:2, 82:7:12:6, 82:7:12:8, 82:7:15:1, 82:7:15:5,
82:7:15:6, 82:7:15:8, 82:7:16:3, 82:7:16:6, 82:7:18:3, 82:7:18:8,
82:7:20:1, 82:7:20:4, 82:7:20:6, 82:7:20:8, 82:7:21:3, 82:7:21:5,
82:7:24:5, 82:7:24:7, 82:7:25:1, 82:7:25:4, 82:7:25:7, 82:7:25:8,
82:7:26:2, 82:7:26:4, 82:7:26:7, 82:7:27:1, 82:7:27:2, 82:7:27:3,
82:7:33:2, 82:7:33:6, 82:7:33:8, 82:7:34:6, 82:7:34:7, 82:7:35:1,
82:7:35:2, 82:7:36:2, 82:7:36:7, 82:7:39:1, 82:7:39:2, 82:7:39:3,
82:7:39:6, 82:14:1:2, 82:14:1:3, 82:14:1:8, 82:14:2:2, 82:14:2:4,
82:14:2:7, 82:14:3:3, 82:14:3:4, 82:14:3:8, 82:14:5:5, 82:14:5:7,
82:14:5:8, 82:14:6:1, 82:14:6:6, 82:14:7:3, 82:14:7:8, 82:14:8:4,
82:14:8:5, 82:14:10:5, 82:14:10:8, 82:14:12:7, 82:14:12:8, 82:14:13:4,
82:14:13:7, 82:14:14:1, 82:14:14:4, 82:14:14:7, 82:14:14:8, 82:14:17:1,
82:14:17:2, 82:14:17:4, 82:14:17:7, 82:14:18:1, 82:14:18:2, 82:14:18:6,
82:14:18:7, 82:14:20:3, 82:14:20:7, 82:14:24:3, 82:14:24:4, 82:14:24:6,
82:14:29:4, 82:14:29:5, 82:14:29:6, 82:14:32:2, 82:14:32:4, 82:14:32:6,
82:14:38:7, 82:14:38:8, 82:14:39:5, 82:14:39:7, 82:14:41:2, 82:14:41:5,
82:14:41:6, 82:14:41:8, 82:15:2:2, 82:15:2:4, 82:15:2:5, 82:15:2:6,
82:15:4:3, 82:15:4:8, 82:15:6:2, 82:15:6:6, 82:15:6:7, 82:15:6:8,
82:15:9:1, 82:15:9:2, 82:15:9:5, 82:15:9:8, 82:15:10:3, 82:15:10:5,
82:15:10:7, 82:15:10:8, 82:15:12:2, 82:15:12:4, 82:15:12:6, 82:15:12:7,
82:15:13:3, 82:15:13:7, 82:15:15:1, 82:15:15:3, 82:15:15:6, 82:15:15:8,
82:15:20:2, 82:15:20:7, 82:15:26:3, 82:15:26:4, 82:15:29:2, 82:15:29:3,
82:15:30:3, 82:15:30:5, 82:15:30:7, 82:15:31:3, 82:15:31:4, 82:15:32:1,

TABLE 5a-continued

Exemplary Enumerated Compounds using Tables 1a, 2a, 3, and 4

82:15:32:4, 82:15:34:1, 82:15:34:6, 82:15:34:7, 82:15:35:3, 82:15:35:4,
82:15:35:5, 82:15:35:7, 82:15:37:1, 82:15:37:3, 82:15:37:4, 82:15:37:6,
82:15:39:1, 82:15:39:4, 82:15:39:6, 82:15:40:1, 82:15:40:4, 82:15:40:6,
82:15:40:7, 82:15:41:4, 82:15:41:5, 82:15:41:8, 82:17:3:2, 82:17:3:3,
82:17:3:6, 82:17:7:1, 82:17:7:5, 82:17:7:7, 82:17:7:8, 82:17:8:1,
82:17:8:3, 82:17:8:5, 82:17:11:1, 82:17:11:8, 82:17:12:2, 82:17:12:3,
82:17:14:5, 82:17:14:6, 82:17:14:7, 82:17:14:8, 82:17:17:1, 82:17:17:3,
82:17:17:6, 82:17:17:8, 82:17:18:1, 82:17:18:6, 82:17:18:7, 82:17:20:6,
82:17:20:7, 82:17:25:2, 82:17:25:3, 82:17:26:2, 82:17:26:3, 82:17:26:5,
82:17:26:8, 82:17:32:4, 82:17:32:6, 82:17:33:3, 82:17:33:7, 82:17:34:1,
82:17:34:2, 82:17:34:7, 82:17:34:8, 82:17:36:3, 82:17:36:7, 82:17:36:8,
82:17:37:2, 82:17:37:4, 82:17:37:6, 82:17:37:8, 82:17:38:1, 82:17:38:3,
82:17:38:6, 82:17:40:1, 82:17:40:2, 82:17:41:4, 82:17:41:5, 83:12:1:1,
83:12:1:4, 83:12:1:5, 83:12:1:6, 83:12:3:4, 83:12:3:5, 83:12:3:7,
83:12:3:8, 83:12:4:1, 83:12:4:3, 83:12:4:4, 83:12:5:3, 83:12:5:5,
83:12:9:1, 83:12:9:2, 83:12:9:7, 83:12:11:5, 83:12:11:6, 83:12:11:7,
83:12:13:3, 83:12:13:6, 83:12:13:7, 83:12:14:1, 83:12:14:2, 83:12:14:3,
83:12:14:5, 83:12:15:2, 83:12:15:4, 83:12:15:6, 83:12:19:1, 83:12:19:4,
83:12:19:6, 83:12:20:2, 83:12:20:3, 83:12:20:4, 83:12:24:2, 83:12:24:4,
83:12:24:7, 83:12:24:8, 83:12:25:2, 83:12:25:3, 83:12:25:4, 83:12:28:1,
83:12:28:6, 83:12:28:8, 83:12:32:2, 83:12:32:8, 83:12:33:2, 83:12:33:3,
83:12:33:4, 83:12:38:2, 83:12:38:6, 83:12:38:7, 83:12:38:8, 83:12:39:2,
83:12:39:4, 83:12:39:8, 83:12:40:1, 83:12:40:4, 83:15:4:1, 83:15:4:3,
83:15:4:5, 83:15:5:1, 83:15:5:6, 83:15:7:1, 83:15:7:4, 83:15:7:5,
83:15:7:6, 83:15:8:1, 83:15:8:7, 83:15:12:2, 83:15:12:5, 83:15:13:2,
83:15:13:4, 83:15:13:5, 83:15:13:8, 83:15:15:1, 83:15:15:3, 83:15:15:4,
83:15:17:2, 83:15:17:6, 83:15:20:1, 83:15:20:6, 83:15:20:7, 83:15:21:7,
83:15:21:8, 83:15:22:1, 83:15:22:2, 83:15:22:3, 83:15:22:8, 83:15:24:1,
83:15:24:4, 83:15:24:8, 83:15:27:1, 83:15:27:2, 83:15:28:3, 83:15:28:6,
83:15:28:8, 83:15:30:6, 83:15:30:7, 83:15:30:8, 83:15:33:2, 83:15:33:4,
83:15:33:5, 83:15:33:8, 83:15:35:1, 83:15:35:3, 83:15:35:7, 83:15:35:8,
83:15:36:2, 83:15:36:4, 83:15:36:6, 83:15:38:2, 83:15:38:3, 83:15:38:4,
83:15:38:7, 83:15:41:1, 83:15:41:5, 83:15:41:8, 86:11:1:2, 86:11:1:5,
86:11:1:7, 86:11:1:8, 86:11:3:3, 86:11:3:4, 86:11:3:7, 86:11:3:8,
86:11:9:3, 86:11:9:4, 86:11:10:3, 86:11:10:4, 86:11:10:5, 86:11:10:6,
86:11:11:2, 86:11:11:5, 86:11:11:7, 86:11:11:8, 86:11:12:4, 86:11:12:6,
86:11:12:8, 86:11:13:2, 86:11:13:5, 86:11:13:6, 86:11:13:7, 86:11:15:4,
86:11:15:6, 86:11:15:8, 86:11:21:2, 86:11:21:3, 86:11:21:5, 86:11:21:8,
86:11:25:4, 86:11:25:6, 86:11:25:8, 86:11:27:2, 86:11:27:4, 86:11:27:6,
86:11:27:8, 86:11:29:7, 86:11:29:8, 86:11:31:6, 86:11:31:8, 86:11:32:1,
86:11:32:4, 86:11:33:1, 86:11:33:3, 86:11:33:7, 86:11:33:8, 86:11:35:1,
86:11:35:4, 86:11:35:5, 86:11:35:8, 86:11:37:1, 86:11:37:7, 86:11:39:5,
86:11:39:6, 86:11:39:7, 86:11:40:2, 86:11:40:3, 86:11:40:7, 86:16:1:1,
86:16:1:3, 86:16:7:1, 86:16:7:7, 86:16:8:4, 86:16:8:6, 86:16:8:7,
86:16:8:8, 86:16:13:1, 86:16:13:5, 86:16:13:6, 86:16:18:1, 86:16:18:2,
86:16:18:4, 86:16:18:8, 86:16:20:4, 86:16:20:5, 86:16:20:7, 86:16:21:1,
86:16:21:3, 86:16:21:5, 86:16:21:6, 86:16:28:2, 86:16:28:3, 86:16:37:1,
86:16:37:2, 86:16:37:4, 86:16:37:8, 88:11:4:2, 88:11:4:7, 88:11:7:1,
88:11:7:7, 88:11:10:4, 88:11:10:5, 88:11:10:6, 88:11:15:1, 88:11:15:4,
88:11:15:5, 88:11:21:1, 88:11:21:2, 88:11:21:3, 88:11:21:5, 88:11:24:4,
88:11:24:7, 88:11:25:2, 88:11:25:4, 88:11:25:5, 88:11:26:3, 88:11:26:7,
88:11:28:1, 88:11:28:5, 88:11:30:3, 88:11:30:4, 88:11:30:5, 88:11:33:1,
88:11:33:2, 88:11:33:3, 88:11:33:5, 88:11:34:5, 88:11:34:6, 88:11:37:3,
88:11:37:5, 88:11:37:6, 88:11:39:2, 88:11:39:8, 88:11:40:2, 88:11:40:3,
88:11:40:7, 88:11:40:8, 88:11:41:1, 88:11:41:3, 88:11:41:5, 88:16:4:1,
88:16:4:2, 88:16:5:1, 88:16:5:3, 88:16:5:8, 88:16:9:5, 88:16:9:6,
88:16:9:7, 88:16:11:3, 88:16:11:6, 88:16:13:1, 88:16:13:4, 88:16:13:6,
88:16:16:2, 88:16:16:3, 88:16:16:4, 88:16:16:6, 88:16:17:3, 88:16:17:5,
88:16:17:6, 88:16:17:8, 88:16:18:2, 88:16:18:4, 88:16:18:5, 88:16:21:1,
88:16:21:3, 88:16:21:5, 88:16:21:6, 88:16:24:7, 88:16:24:8, 88:16:25:4,
88:16:25:5, 88:16:25:6, 88:16:26:1, 88:16:26:7, 88:16:29:3, 88:16:29:4,
88:16:29:6, 89:7:3:1, 89:7:3:5, 89:7:4:2, 89:7:4:7, 89:7:4:8, 89:7:9:3,
89:7:9:5, 89:7:9:7, 89:7:9:8, 89:7:13:2, 89:7:13:3, 89:7:13:4,
89:7:13:5, 89:7:16:2, 89:7:16:3, 89:7:16:4, 89:7:16:7, 89:7:22:1,
89:7:22:2, 89:7:22:3, 89:7:22:5, 89:7:28:3, 89:7:28:5, 89:7:28:7,
89:7:30:3, 89:7:30:5, 89:7:30:7, 89:7:33:1, 89:7:33:5, 89:7:37:3,
89:7:37:8, 89:7:38:1, 89:7:38:3, 89:7:38:5, 89:7:38:7, 89:7:41:2,
89:7:41:7, 89:8:5:2, 89:8:5:3, 89:8:5:8, 89:8:7:5, 89:8:7:8, 89:8:8:1,
89:8:8:6, 89:8:8:8, 89:8:12:1, 89:8:12:4, 89:8:12:7, 89:8:12:8,
89:8:13:2, 89:8:13:3, 89:8:13:7, 89:8:16:3, 89:8:16:6, 89:8:16:8,
89:8:18:1, 89:8:18:2, 89:8:18:3, 89:8:18:6, 89:8:19:3, 89:8:19:5,
89:8:19:6, 89:8:19:7, 89:8:21:1, 89:8:21:4, 89:8:21:6, 89:8:21:7,
89:8:23:3, 89:8:23:4, 89:8:23:7, 89:8:24:3, 89:8:24:4, 89:8:24:5,
89:8:24:8, 89:8:30:2, 89:8:30:5, 89:8:30:7, 89:8:32:1, 89:8:32:2,
89:8:32:4, 89:8:32:8, 89:8:33:3, 89:8:33:7, 89:9:2:2, 89:9:2:5,
89:9:2:6, 89:9:2:7, 89:9:7:6, 89:9:7:8, 89:9:11:2, 89:9:11:6,
89:9:13:3, 89:9:13:4, 89:9:13:5, 89:9:13:6, 89:9:15:1, 89:9:15:3,

TABLE 5a-continued

Exemplary Enumerated Compounds using Tables 1a, 2a, 3, and 4

89:9:15:4, 89:9:15:5, 89:9:22:1, 89:9:22:6, 89:9:22:7, 89:9:23:2,
89:9:23:5, 89:9:23:8, 89:9:24:2, 89:9:24:3, 89:9:24:6, 89:9:24:7,
89:9:26:3, 89:9:26:5, 89:9:28:3, 89:9:28:8, 89:9:29:2, 89:9:29:4,
89:9:29:5, 89:9:32:4, 89:9:32:5, 89:9:32:7, 89:9:32:8, 89:9:36:2,
89:9:36:8, 89:14:1:7, 89:14:1:8, 89:14:9:5, 89:14:9:6, 89:14:9:8,
89:14:10:1, 89:14:10:2, 89:14:10:3, 89:14:10:7, 89:14:11:2, 89:14:11:6,
89:14:14:2, 89:14:14:3, 89:14:14:8, 89:14:15:7, 89:14:15:8, 89:14:18:2,
89:14:18:3, 89:14:23:1, 89:14:23:2, 89:14:23:4, 89:14:25:1, 89:14:25:4,
89:14:28:2, 89:14:28:4, 89:14:28:8, 89:14:35:2, 89:14:35:5, 89:14:35:6,
89:14:35:8, 92:8:6:1, 92:8:6:3, 92:8:6:5, 92:8:6:8, 92:8:10:1,
92:8:10:2, 92:8:10:4, 92:8:10:6, 92:8:11:1, 92:8:11:3, 92:8:16:1,
92:8:16:4, 92:8:16:6, 92:8:16:7, 92:8:19:3, 92:8:19:5, 92:8:19:6,
92:8:19:8, 92:8:20:4, 92:8:20:5, 92:8:20:8, 92:8:21:1, 92:8:21:2,
92:8:21:5, 92:8:21:7, 92:8:23:1, 92:8:23:2, 92:8:23:3, 92:8:23:7,
92:8:31:5, 92:8:31:7, 92:8:38:1, 92:8:38:4, 92:8:40:1, 92:8:40:3,
92:8:40:5, 92:8:40:6, 92:9:1:2, 92:9:1:4, 92:9:1:7, 92:9:5:2, 92:9:5:3,
92:9:5:6, 92:9:7:2, 92:9:7:5, 92:9:7:7, 92:9:7:8, 92:9:8:1, 92:9:8:5,
92:9:8:7, 92:9:8:8, 92:9:14:6, 92:9:14:7, 92:9:16:3, 92:9:16:4,
92:9:16:5, 92:9:16:8, 92:9:18:1, 92:9:18:2, 92:9:18:6, 92:9:18:8,
92:9:19:3, 92:9:19:5, 92:9:19:7, 92:9:19:8, 92:9:20:1, 92:9:20:2,
92:9:20:5, 92:9:26:4, 92:9:26:5, 92:9:26:7, 92:9:27:2, 92:9:27:3,
92:9:27:6, 92:9:30:2, 92:9:30:4, 92:9:34:1, 92:9:34:4, 92:9:34:8,
92:9:35:1, 92:9:35:4, 92:9:35:8, 92:9:36:1, 92:9:36:4, 92:9:36:6,
92:9:36:7, 92:9:40:1, 92:9:40:3, 92:9:40:5, 92:9:40:6, 92:15:1:6,
92:15:1:7, 92:15:1:8, 92:15:9:1, 92:15:9:4, 92:15:9:7, 92:15:11:1,
92:15:11:6, 92:15:12:4, 92:15:12:5, 92:15:12:6, 92:15:15:1, 92:15:15:6,
92:15:15:7, 92:15:16:1, 92:15:16:2, 92:15:16:7, 92:15:16:8, 92:15:18:1,
92:15:18:3, 92:15:18:4, 92:15:20:2, 92:15:20:5, 92:15:20:6, 92:15:24:1,
92:15:24:5, 92:15:24:6, 92:15:24:8, 92:15:25:6, 92:15:25:8, 92:15:26:2,
92:15:26:6, 92:15:29:3, 92:15:29:7, 92:15:31:2, 92:15:31:3, 92:15:31:6,
92:15:32:2, 92:15:32:4, 92:15:32:6, 92:15:32:7, 92:15:34:1, 92:15:34:3,
92:15:34:6, 92:15:34:8, 92:15:39:1, 92:15:39:3, 92:15:39:4, 92:15:39:8,
92:15:41:1, 92:15:41:5, 92:15:41:8, 93:11:4:1, 93:11:4:3, 93:11:4:5,
93:11:4:7, 93:11:7:3, 93:11:7:6, 93:11:7:8, 93:11:8:2, 93:11:8:6,
93:11:10:1, 93:11:10:2, 93:11:14:5, 93:11:14:6, 93:11:18:2, 93:11:18:4,
93:11:18:7, 93:11:22:2, 93:11:22:5, 93:11:22:7, 93:11:26:1, 93:11:26:3,
93:11:26:6, 93:11:26:8, 93:11:27:4, 93:11:27:6, 93:11:29:1, 93:11:29:3,
93:11:31:7, 93:11:31:8, 93:11:32:2, 93:11:32:3, 93:11:32:4, 93:11:32:5,
93:11:33:3, 93:11:33:4, 93:11:33:6, 93:11:33:8, 93:11:37:3, 93:11:37:4,
93:11:37:6, 93:11:37:8, 93:11:38:5, 93:11:38:6, 93:11:39:1, 93:11:39:6,
93:11:41:2, 93:11:41:6, 93:11:41:8, 93:13:1:3, 93:11:1:6, 93:13:1:8,
93:13:2:4, 93:13:2:5, 93:13:3:1, 93:13:3:3, 93:13:4:1, 93:13:4:2,
93:13:4:3, 93:13:4:4, 93:13:5:1, 93:13:5:4, 93:13:5:6, 93:13:5:8,
93:13:8:3, 93:13:8:6, 93:13:8:8, 93:13:9:2, 93:13:9:4, 93:13:9:5,
93:13:16:2, 93:13:16:8, 93:13:17:1, 93:13:17:6, 93:13:18:3, 93:13:18:4,
93:13:18:6, 93:13:18:8, 93:13:19:4, 93:13:19:6, 93:13:20:4, 93:13:20:6,
93:13:21:1, 93:13:21:6, 93:13:24:1, 93:13:24:3, 93:13:24:7, 93:13:24:8,
93:13:28:1, 93:13:28:2, 93:13:28:5, 93:13:28:6, 93:13:30:1, 93:13:30:2,
93:13:30:4, 93:13:30:6, 93:13:31:2, 93:13:31:3, 93:13:31:5, 93:13:31:7,
93:13:32:2, 93:13:32:6, 93:13:36:1, 93:13:36:7, 93:13:37:1, 93:13:37:4,
93:13:37:6, 93:13:37:8, 95:8:1:2, 95:8:1:4, 95:8:1:6, 95:8:3:2,
95:8:3:4, 95:8:3:6, 95:8:5:1, 95:8:5:2, 95:8:5:8, 95:8:6:2, 95:8:6:6,
95:8:6:7, 95:8:6:8, 95:8:8:3, 95:8:8:5, 95:8:10:4, 95:8:10:5,
95:8:10:6, 95:8:12:4, 95:8:12:5, 95:8:12:7, 95:8:12:8, 95:8:15:3,
95:8:15:4, 95:8:15:5, 95:8:15:7, 95:8:17:1, 95:8:17:2, 95:8:17:8,
95:8:19:2, 95:8:19:5, 95:8:19:7, 95:8:19:8, 95:8:20:3, 95:8:20:6,
95:8:22:2, 95:8:22:4, 95:8:23:6, 95:8:23:7, 95:8:25:1, 95:8:25:2,
95:8:25:5, 95:8:27:4, 95:8:27:5, 95:8:30:5, 95:8:30:7, 95:8:32:1,
95:8:32:2, 95:8:32:7, 95:8:32:8, 95:8:37:3, 95:8:37:4, 95:8:41:2,
95:8:41:6, 95:11:6:1, 95:11:6:2, 95:11:6:7, 95:11:7:1, 95:11:7:2,
95:11:7:7, 95:11:8:6, 95:11:8:7, 95:11:10:1, 95:11:10:3, 95:11:10:8,
95:11:12:3, 95:11:12:6, 95:11:13:1, 95:11:13:5, 95:11:13:6, 95:11:17:2,
95:11:17:3, 95:11:17:7, 95:11:24:2, 95:11:24:4, 95:11:25:1, 95:11:25:4,
95:11:26:3, 95:11:26:4, 95:11:26:5, 95:11:27:1, 95:11:27:5, 95:11:27:6,
95:11:30:6, 95:11:30:8, 95:11:32:3, 95:11:32:5, 95:11:32:8, 95:11:34:1,
95:11:34:6, 95:11:34:8, 95:11:35:1, 95:11:35:2, 95:11:35:7, 95:11:36:1,
95:11:36:2, 95:11:36:6, 95:11:37:4, 95:11:37:7, 95:11:37:8, 95:11:41:1,
95:11:41:2, 95:11:41:5, 95:11:41:8, 95:17:1:1, 95:17:1:2, 95:17:1:3,
95:17:1:6, 95:17:3:1, 95:17:3:5, 95:17:3:6, 95:17:3:8, 95:17:8:2,
95:17:8:4, 95:17:8:8, 95:17:10:1, 95:17:10:5, 95:17:10:7, 95:17:12:1,
95:17:12:4, 95:17:12:7, 95:17:12:8, 95:17:13:3, 95:17:13:7, 95:17:14:3,
95:17:14:4, 95:17:14:6, 95:17:14:8, 95:17:15:1, 95:17:15:3, 95:17:20:2,
95:17:20:3, 95:17:20:4, 95:17:20:8, 95:17:21:1, 95:17:21:3, 95:17:21:5,
95:17:21:8, 95:17:23:2, 95:17:23:3, 95:17:23:6, 95:17:23:8, 95:17:24:2,
95:17:24:3, 95:17:24:5, 95:17:24:7

More typical compounds are of the form where E is either C(=O)O or C(=O)S and Q is C(=NH)NH$_2$ which are represented by the following formula I:

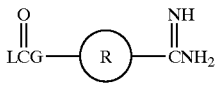

I wherein G is O or S and pharmaceutically acceptable acid addition salts.

In the above formula I, (R) is a fused bicyclic ring. The ring preferably includes a six-membered unsaturated ring fused to a 5- or 6-membered hydrocarbon ring or heterocyclic ring. The heterocyclic rings can contain 1–4 heteroatoms selected from the group of O, N, S and mixtures.

In addition, the hydrocarbon ring variety of the fused bicyclic ring can contain one or more pendant groups such as H, lower alkyl of 1–5 carbon atoms, CF$_3$, or halogen such as Cl, F, I, or Br.

The 6-membered unsaturated ring can be benzene or can include one or two nitrogen atoms in the ring. Examples of more typical (R) bicyclic ring varieties identified as group R$_1$ are as follows:

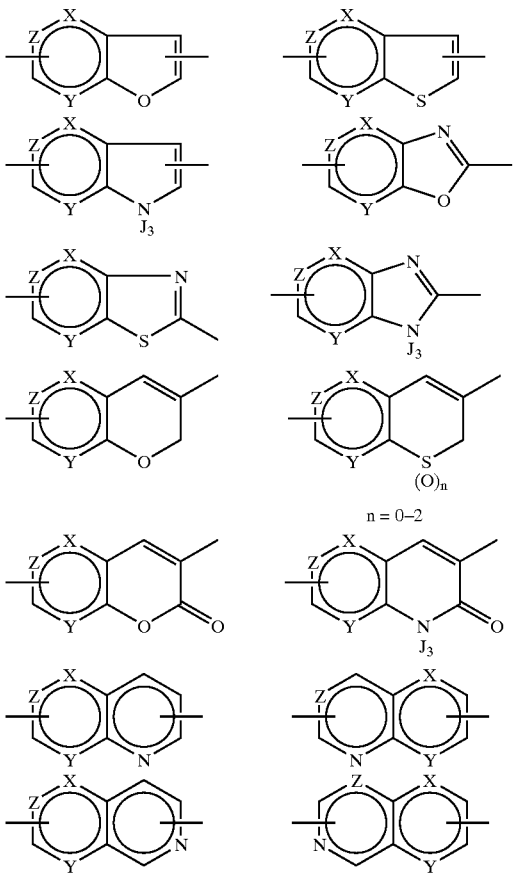

wherein each X, Y and Z individually is N or C(J$_2$), and J$_2$ is individually H, F, Cl, Br, I, CF$_3$ or lower alkyl of 1–5 carbons.

J$_3$ is H or a lower alkyl having 1–5 carbon atoms.

In the above formula I, L is an unsaturated aliphatic chain, a 2-, 3- or 4-substituted benzene ring, a cycloalkyl ring of 3–7 carbons, or a five or six-membered heterocyclic ring containing 1–4 heteroatoms, preferably O, N or S. Mixtures of heteratoms can be employed when desired. Examples of more typical L groups, identified as group L1, are as follows:

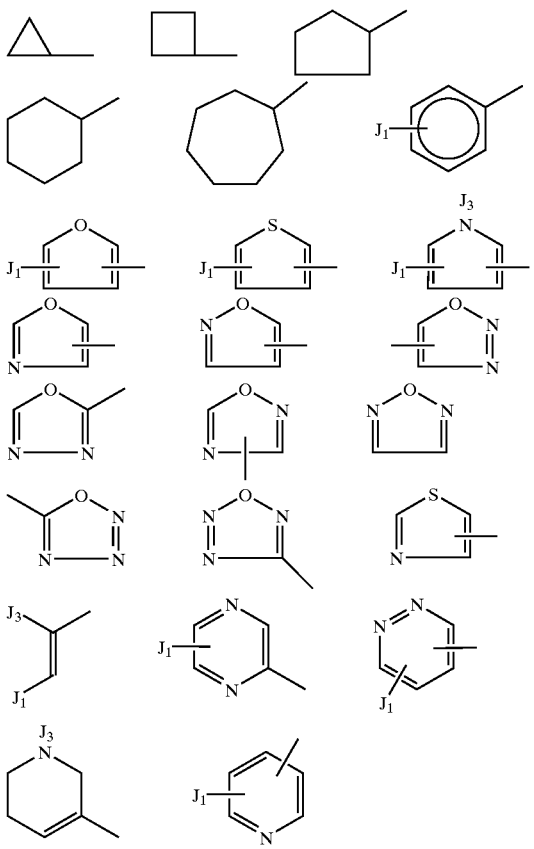

wherein each J$_1$ is H, (CH$_2$)$_m$CO$_2$H, (CH$_2$)$_m$CH$_2$OH, (CH$_2$)$_m$CONH$_2$, (CH$_2$)$_m$NHJ$_3$, CF$_3$, halogen such as Cl, Br, I, and F, alkyl, alkoxy, aryl or heterocyclic. J$_3$ in the above formula is H, straight or branched lower alkyl of 1–4 carbon atoms, and m is an integer from 0 to 5. The alkyl group preferably contains 1–10 carbon atoms and more preferably 1–4 carbon atoms, examples of which are methyl, ethyl and propyl The alkoxy groups preferably contain 1–10 carbon atoms and more preferably 1–3 carbon atoms, examples of which are methoxy and ethoxy.

The aryl groups preferably contain 6–14 carbon atoms, examples of which are phenyl, naphthyl and anthracyl, with phenyl being most preferred The heterocyclic groups preferably contain 5 or 6 atoms in the ring, 1–4 being a heteroatom, such as N, S or O. Mixtures of heteroatoms can be used when desired. Examples of more typical five-membered rings are those disclosed above. Examples of some suitable six-membered heteroaromatic rings are 2-, 3- or 4-pyrazinyl, 2-, 3- or 4-pyrimidinyl, 2-, 3- or 4-pyridazinyl, 2-, 3- or 4-pyridinyl, 2- or 3-furanyl, and 2- or 3-thienyl.

L is preferably phenyl, 2- or 3-furanyl or 2- or 3-thienyl.

Examples of some compounds according to the present invention are represented by one of the following formulae II, III, IV, V, VI, VII, VIII, IX, X, XI, XII, or XIII.

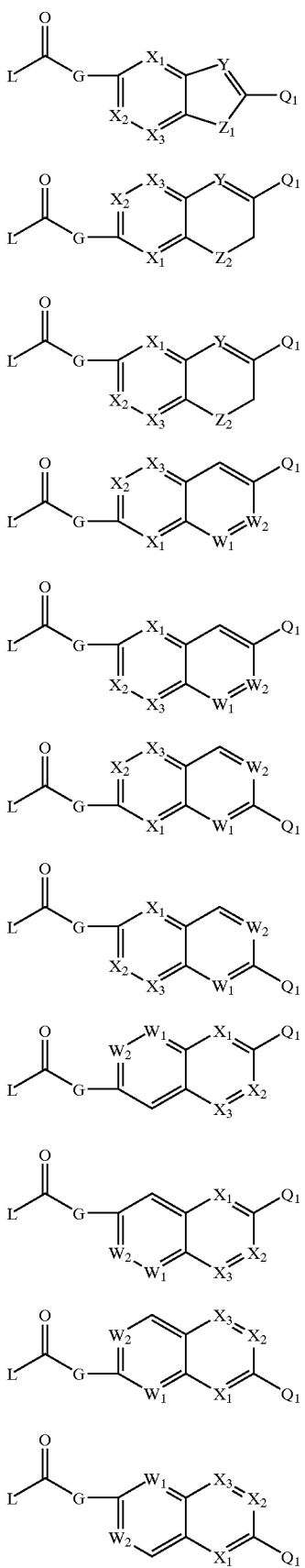

-continued

XIII wherein
G is O or S;
L is selected from the group consisting of a
  cycloalkyl ring of 3–7 carbon atoms,
  alkene of 2–6 carbon atoms,
  benzene ring,
  5 membered unsubstituted or substituted aromatic heterocyclic ring, having one, two or three heteroatoms which are the same or different and which are selected from sulfur, oxygen and nitrogen, or
  6 membered unsubstituted or substituted aromatic heterocyclic ring, having one, two, or three heteroatoms which are the same or different and which are selected from sulfur, oxygen and nitrogen
wherein each member of said group can have 0, 1, 2, or 3 pendant groups selected from the group $J_1$;
wherein each $J_1$ is individually selected from the group consisting of
  H, halogen,
  $CF_3$,
  alkyl group, straight or branched, of 1–5 carbon atoms,
  alkoxy group having 1–5 carbon atoms,
  aryl, and
  heterocyclic.
$Q_1$ is selected from $NH_2$, $C(=NH)NH_2$, $NHC(=NH)NH_2$, or $CH_2NH_2$;
$X_1$, $X_2$ and $X_3$ are independently $C(J_2)$ or N;
Y is $C(J_2)$ or $N(J_3)$;
$Z_1$ is O, N or S;
$Z_2$ is O, N, S, SO, $SO_2$ or CO;
each $J_2$ is individually selected from
  H, halogen,
  $CF_3$ or,
  lower alkyl, straight or branched, of 1–5 carbon atoms;
each $J_3$ is individually selected from
  H or,
  lower alkyl, straight or branched, of 1–5 carbon atoms; and
  pharmaceutically acceptable salts thereof.

Acids which can be used to prepare salts are pharmaceutically acceptable ones including inorganic acids such as hydrochloric acid, sulfuric acid and phosphoric acid and organic acids such as acetic acid, lactic acid, citric acid, methanesulfonic acid, succinic acid, fumaric acid and maleic acid.

The compounds of the present invention and their pharmaceutically acceptable acid addition salts are useful as anti-complement agents. They exhibit potent inhibiting action against Factor D of the alternate complement pathway and C1s of the classical complement pathway. In fact, they are more potent inhibitors of Factor D and C1s than prior art compounds, including those mentioned in U.S. Pat. No. 4,490,388 to Fujii et al.

The compounds also exhibit inhibitory activities against proteases, such as thrombin, Factor Xa, Factor XIIa, plasmin and kallikrein and thus would be useful for anticoagulation and antiplatelet activity. In addition, these compounds would be useful in reducing blood loss secondary to anticoagulation. Compounds of the present invention would be useful for inducing blood anesthesia.

The compounds of the present invention can be prepared by reacting a carboxylic acid with a substituted carbodiimide in the presence of a base such as pyridine, triethylamine or 4-dimethylaminopyridine to produce a mixed anhydride.

The mixed anhydride is then reacted with a phenolic compound or acid salt thereof in a base such as pyridine, triethylamine or 4-dimethylaminopyridine to provide the desired amidine compound. The reaction is preferably carried out at temperatures of from about 0° C. to about 80° C., preferably 0° C.–10° C., using stoichiometrical amounts of the reactants or up to about a 10% excess of one of the reactants.

The compounds of the present invention can also be prepared by reacting an acid halide with a phenolic compound or acid salt thereof which is suspended or dissolved in an organic solvent such as pyridine, dimethyl formamide or dimethyl sulfoxide. When the solvent such as dimethyl formamide or dimethyl sulfoxide is used, it is desirable to use a base such as pyridine, triethylamine or 4-dimethylaminopyridine to produce the desired amidine compound.

DOSAGE AND FORMULATION

The compounds of the present invention can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient for mammals (including man) can be expected to be about 0.001 to 1000 milligram (mg) per kilogram (kg) of body weight, with the preferred dose being 0.1 to about 30 mg/kg.

Dosage forms (compositions suitable for administration) contain from about 1 mg to about 100 mg of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets and powders, or in liquid dosage forms, such as elixirs, syrups and suspensions. It can be formulated in a sterile liquid or as a sterile powder for parenteral use, to be administered parenterally, as a sterile liquid dosage form or controlled-release depot injection. The active ingredient can also be administered intranasally (nose drops) or by inhalation. Other dosage forms are potentially possible such as administration transdermally, via a patch mechanism, ointment or iontophoretic device. It can be administered into a body cavity, such as into the rectum, vagina, or urethea as a solution, semi-solid or solid.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose) and related sugar solutions and glycols, such as propylene glycol or polyethylene glycols are suitable carriers for parenteral solutions. Solutions for parenteral administration preferably contain a water-soluble salt of the active ingredient, suitable stabilizing agents, complexing agents, chelating agents, sufactants, and if necessary, buffer substances. Antioxidizing agents such as sodium bisulfite, sodium sulfite or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company, a standard reference text in this field.

Examples of useful pharmaceutical dosage forms for administration of the compounds of this invention can be illustrated as follows:

Capsules

A large number of unit capsules are prepared by filling standard two-piece hard gelatin capsules each with 100 mg of powdered active ingredient, 150 mg of lactose, 50 mg of powdered cellulose, and 6 mg of magnesium stearate or colloidal silica.

Soft Gelatin Capsules

A mixture of active ingredient in a digestible oil such as soybean oil, cottonseed oil, or olive oil or a cosolvent mix containing one or more of PEG400, sorbitol, glycerol, propylene glycol is prepared and injected into thermo formed gelatin to form seam or seamless soft gelatin capsules or beads containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate coatings may be applied to increase palatability or delay absorption.

Moreover, the compounds of the present invention can be administered in the form of nose drops or a nasal inhaler.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

The following non-limiting examples are presented to further facilitate an understanding of the present invention:

EXAMPLE 1

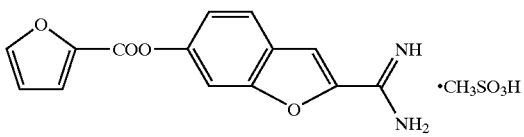

2-Amidino-6-benzofuranyl 2-furanylcarboxylate methanesulfonate

2Cyano-6-hydroxybenzofuran (Rene, L.; Buisson, J.-P.; Royer. R. Reaction induites par le chlorhydrate de pyridine. XVI. -Sur la desalcoylation des derives Bz-methoxyles de nitriles et amides coumariliques. *Bull. Soc. Chim.* 1974, 475–476; 1.45 g, 9.11 mmol) was added to a cooled, saturated methanol-HCl solution (10 mL) and the mixture was stirred for 20 h at ambient temperature. The reaction mixture was concentrated in vacuo to give a solid. The solid was suspended in anhydrous methanol (40 mL) and gaseous $NH_3$ was introduced into the mixture at 50° C. for 3 h to give a homogenous solution. The solvent was evaporated in vacuo, and the resulting solid was suspended in methanol (10 mL) and then treated with a saturated solution of $NaHCO_3$ (30 mL). The precipitate was collected by filtration, washed with water (15 mL) and then dried in vacuo over $P_2O_5$ for 3 h. The solid (1.48 g) was suspended in 5 mL of methanol and then treated with methanesulfonic acid (1.1 g, 11.5 mmol). The precipitated material was recrystallized from methanol to give 1.62 g (65%) of 2-amidino-6-hydroxybenzofuran methanesulfonate as a brown solid, mp 253–254° C.

| Analysis: | Calc for $C_9H_8N_2O_2$. $CH_3SO_3H$ | C, 44.11; H, 4.44; N, 10.29 |
|---|---|---|
| | Found: | C, 44.23; H, 4.47; N, 10.23 |

1-(3-Dimethylaminopropyl)-3-ethylcarbodiimide methiodide (1.46 g, 4.91 mmol) was added to a cooled solution of 2-furoic acid (Aldrich, 0.5 g, 4.46 mol) in anhydrous pyridine (15 mL) and the reaction mixture was stirred for 30 min. To this cooled (~4° C.) reaction mixture was added 2-amidino-6-hydroxybenzofuran methanesulfonate, (1.21 g, 4.46 mmol) in one portion and the reaction mixture allowed to warm to room temperature with stirring for 16 h. The reaction mixture was triturated with $Et_2O$ (25 mL) and the $Et_2O$ layer was removed by decantation. This process was repeated once and the residue was dissolved in methanol (10 mL). Saturated $NaHCO_3$ solution (50 mL) was added and the precipitated material was collected by filtration, washed with water (2×20 mL) and then dried in vacuo over $P_2O_5$ for 1 h to give 0.6 g of the desired material as a carbonate. The carbonate (0.6 g) was suspended in 3 mL of methanol and then treated with methanesulfonic acid (0.34 g, 3.53 mmol). The reaction mixture was warmed gently for 2 min, sonicated for 2 min, and the precipitated solid was collected to give 0.86 g (53%) of the title compound. Recrystallization from methanol afforded an analytical sample as an off-white solid, mp 226–228° C.

| Analysis: | Calc for $C_{14}H_{10}N_2O_4$. $CH_3SO_3H$: | C, 49.20; H, 3.85; N, 7.65 |
|---|---|---|
| | Found | C, 48.92; H, 3.90; N, 7.58 |

EXAMPLE 2

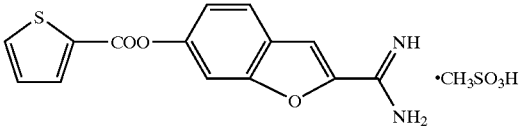

2-Amidino-6-benzofuranyl 2-thiophenecarboxylate methanesulfonate 1-(3-Dimethylaminopropyl)-3-ethylcarbodiimide methiodide (Aldrich, 1.37 g, 4.61 mmol) was added to a cooled solution of 2-thiophenecarboxylic acid (Aldrich, 0.591 g, 4.61 mmol) in anhydrous pyridine (10 mL) and the reaction mixture was stirred for 30 min To this cooled (~4° C.) reaction mixture was added 2-amidino-6-hydroxybenzofuran methanesulfonate (from Example 1, 1.25 g, 4.59 mmol) in one portion and the reaction mixture allowed to warm to room temperature with stirring for 16 h. The reaction mixture was triturated with $Et_2O$ (25 mL) and the $Et_2O$ layer was removed by decantation. This process was repeated once and the residue was dissolved in methanol (10 mL). Saturated $NaHCO_3$ solution (50 mL) was added and the precipitated material was collected by filtration, washed with water (2×20 mL) and then dried in vacuo over $P_2O_5$ for 3 h to give 0.7 g of the desired material as a carbonate. The carbonate (0.7 g) was suspended in 4 mL of methanol and then treated with methanesolfonic acid (0.41 g, 4.27 mmol). The reaction mixture was warmed gently for 2 min, sonicated for 2 min, and the precipitated solid recrystallized from methanol to give 0.35 g (20%) of an analytical sample of the title compound as a pale-yellow solid, mp 248–250° C.

| Analysis: | Calc for $C_{14}H_{10}N_2O_3S$. $CH_3SO_3H$: | C, 47.11; H, 3.69; N, 7.33 |
|---|---|---|
| | Found: | C, 46.96; H, 3.72; N, 7.21 |

EXAMPLE 3

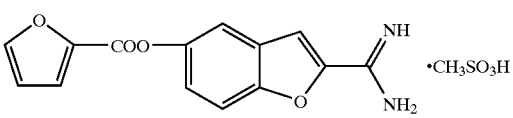

2-Amidino-5-benzofuranyl 2-furanylcarboxylate methanesulfonate

Hydrogen chloride gas was bubbled through a suspension of 2-cyano-5-hydroxybenzofuran (Rene, L.; Buisson, J. P.; Royer, R. Reaction induites par le chlorhydrate de pyridine. XVI.-Sur la desalcoylation des derives Bz-methoxyles de nitriles et amides coumariliques. *Bull. Soc. Chim.* 1974, 475–476; 5.0 g, 31.4 mmol) in methanol (125 mL) at 4° C. for 0.5 h. The reaction stirred overnight at ambient temperature. The reaction was concentrated in vacuo and the residue dissolved in methanol (200 mL). Ammonia gas was bubbled through the suspension of the imidate at 4° C. for 1 h and then 50° C. for 2 h. The reaction was stirred 72 h at room temperature for convenience. The solution was concentrated in vacuo and the residue was suspended in saturated $NaHCO_3$ (150 mL). The carbonate was collected by filtration, washed with water and dried at ambient temperature for 4 h. The salt (7.71 g, 29.7 mmol) was suspended in methanol (15 mL) and methanesulfonic acid (2.33 mL, 35.6 mmol) was added dropwise over a few minutes. The suspension was sonicated, ether (100 mL) was added and the reaction was again sonicated. The solid was collected by filtration and dried at ambient temperature overnight. The solid was recrystallized from methanol-ether and collected by filtration to give 4.9 g (57%) of 2-amidino-5-hydroxybenzofuran methanesulfonate as a brown solid, mp 247–248° C.

| Analysis: | Calc for $C_9H_8N_2O_2$. $CH_3SO_3H$: | C, 44.11; H, 4.44; N, 10.29 |
|---|---|---|
| | Found: | C, 44.08; H, 4.45; N, 10.17 |

1-(3-Dimethylaminopropyl)-3-ethylcarbodiimide methiodide (Aldrich, 1.09 g, 3.67 mmol) was added to a cooled solution of 2-furoic acid (Aldrich, 0.41 g, 3.67 mmol) in anhydrous pyridine (10 mL) and the reaction mixture was stirred for 30 min. To this cooled (~4° C.) reaction mixture was added 2-amidino-5-hydroxybenzofuran methanesulfonate (from Example 1, 1.0 g, 3.67 mmol) in one portion, and the reaction mixture allowed to warm to room temperature with stirring for 16 h. The reaction mixture was triturated with $Et_2O$ (10 mL) and the $Et_2O$ layer was removed by decantation. This process was repeated twice and the residue was dissolved in methanol (10 mL). Saturated $NaHCO_3$ solution (30 mL) was added and the precipitated material was collected by filtration, washed with water (2×10 mL) and then dried in vacuo over $P_2O_5$ for 1 h to give 0.82 g of the desired material as a carbonate. The carbonate (0.82 g) was suspended in 5 mL of ethanol and then treated with methanesulfonic acid (0.35 g, 3.64 mmol). The reaction mixture was warmed gently for 2 min, sonicated for 2 min, and the precipitated solid was collected to give 0.79 g (59%) of the title compound. Recrystallization from ethanol afforded an analytical sample as a tan solid, mp 243–244° C.

| Analysis: | Calc for $C_{14}H_{10}N_2O_4$. $CH_3SO_3H$: | C, 49.18; H, 3.85; N, 7.65 |
|---|---|---|
| | Found | C, 48.98; H, 3.91; N, 7.63 | of the imidate at 4° C. for 1 h and then 50° C. for 2 h. The reaction was stirred 72 h at room temperature for convenience. The solution was concentrated in vacuo and the residue was suspended in saturated $NaHCO_3$ (150 mL). The carbonate was collected by filtration, washed with water and dried at ambient temperature for 4 h. The salt (7.71 g, 29.7 mmol) was suspended in methanol (15 mL) and methanesulfonic acid (2.33 mL, 35.6 mmol) was added dropwise over a few minutes. The suspension was sonicated, ether (100 mL) was added and the reaction was again sonicated. The solid was collected by filtration and dried at ambient temperature overnight. The solid was recrystallized from methanol-ether and collected by filtration to give 4.9 g (57%) of 2-amidino-5-hydroxybenzofuran methanesulfonate as a brown solid, mp 247–248° C.

| Analysis: | Calc for $C_9H_8N_2O_2$. $CH_3SO_3H$: | C, 44.11; H, 4.44; N, 10.29 |
|---|---|---|
| | Found: | C, 44.08; H, 4.45; N, 10.17 |

1-(3 Dimethylaminopropyl)-3-ethylcarbodiimide methiodide (Aldrich, 1.09 g, 3.67 mmol) was added to a cooled solution of 2-furoic acid (Aldrich, 0.41 g, 3.67 mmol) in anhydrous pyridine (10 mL) and the reaction mixture was stirred for 30 min. To this cooled (~4° C.) reaction mixture was added 2-amidino-5-hydroxybenzofuran methanesulfonate (from Example 1, 1.0 g, 3.67 mmol) in one portion, and the reaction mixture allowed to warm to room temperature with stirring for 16 h. The reaction mixture was triturated with $Et_2O$ (10 mL) and the $Et_2O$ layer was removed by decantation. This process was repeated twice and the residue was dissolved in methanol (10 mL). Saturated $NaHCO_3$ solution (30 mL) was added and the precipitated material was collected by filtration, washed with water (2×10 mL) and then dried in vacuo over $P_2O_5$ for 1 h to give 0.82 g of the desired material as a carbonate. The carbonate (0.82 g) was suspended in 5 mL of ethanol and then treated with methanesulfonic acid (0.35 g, 3.64 mmol). The reaction mixture was warmed gently for 2 min, sonicated for 2 min, and the precipitated solid was

EXAMPLE 5

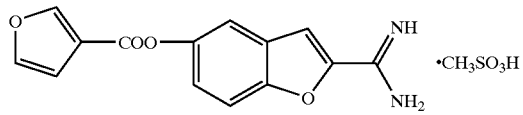

2-Amidino-5-benzofuranyl 3-furanylcarboxylate methanesulfonate 1-(3-Dimethylaminopropyl)-3-ethylcarbodiimide methiodide (Aldrich, 1.09 g, 3.67 mmol) was added to a cooled solution of 3-furoic acid (Aldrich, 0.41 g, 3.67 mmol) in anhydrous pyridine (10 mL) and the reaction mixture was stirred for 30 min. To this cooled (~° C.) reaction mixture was added 2-amidino-5-hydroxybenzofuran methanesulfonate (from Example 3, 1.0 g, 3.67 mmol) in one portion, and the reaction mixture allowed to warm to room temperature with stirring for 16 h. The reaction mixture was triturated with $Et_2O$ (10 mL) and the $Et_2O$ layer was removed by decantation. This process was repeated twice and the residue was suspended in methanol (10 mL). Saturated $NaHCO_3$ solution (30 mL) was added and the precipitated material was collected by filtration, washed with water (10 mL) and then dried for 3 h to give 0.5 g of the desired material as a carbonate. The carbonate (0.5 g) was suspended in 2 mL of ethanol and then treated with methanesulfonic acid (0.46 g, 4.79 mmol). The reaction mixture was warmed gently for 2 min, sonicated for 2 min, and the precipitated solid was recrystallized from ethanol to give 0.462 g (34%) of the title compound as an off-white solid, mp 248–250° C.

| Analysis: | Calc for $C_{14}H_{10}N_2O_4$. $CH_3, SO_3H$: | C, 49.18; H, 3.85; N, 7.65 |
|---|---|---|
| | Found: | C, 48.91; H, 3.89; N, 7.47 |

EXAMPLE 6

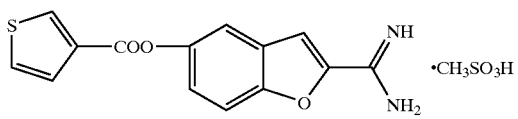

2-Amidino-5-benzofuranyl 3-thiophenecarboxylate methanesulfonate 1-(3-Dimethylaminopropyl)-3-ehtylcarbodiimide methiodide (Aldrich, 0.69 g, 2.31 mmol) was added to a cooled solution of 3-thiophenecarboxylic acid (Aldrich, 0.3 g, 2.31 mmol) in anhydrous pyridine (8 mL) and the reaction mixture was stirred for 30 min. To this cooled (~4° C.) reaction mixture was added 2-amidino-5-hydroxybenzofuran methanesulfonate, (from Example 3, 0.6 g, 2.20 mmol) in one portion, and the rection mixture allowed to warm to room temperature with stirring for 16 h. The reaction mixture was triturated with $Et_2O$ (10 mL) and the $Et_2O$ layer was removed by decantation. This process was repeated twice and the residue was dissolved in methanol (10 mL). Saturated $NaHCO_3$ soltuion (20 mL) was added and the precipitated material was collected by filtration, washed with water (2×10 mL) and then dried *in vacuo* over $P_2O_5$ for 1 h to give 0.42 g of the desired material as a carbonate. The carbonate (0.42 g) was suspended in 5 mL of ethanol and then treated with methanesulfonic acid (0.25 g, 2.60 mmol). The reaction mixture was warmed gently for 2 min, sonicated for 2 min, and the precipitated solid was collected to give 0.34 g (40%) of title compound. Recrystallization from ethanol afforded an analytical sample as a tan solid, mp 260–262° C.

| Analysis: | Calc for $C_{14}H_{10}N_2O_3S$. $CH_3SO_3H$: | C, 47.11; H, 3.69; N, 7.33 |
|---|---|---|
| | Found: | C, 46.97; H, 3.70; N, 7.34 |

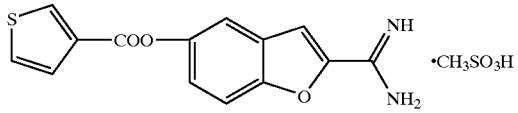

2-Amidino-5-benzofuranyl 3-thiophenecarboxylate methanesulfonate 1-(3-Dimethylaminopropyl)-3-ethylcarbodiimide methiodide (Aldrich, 0.69 g, 2.31 mmol) was added to a cooled solution of 3-thiophenecarboxylic acid (Aldrich, 0.3 g, 2.31 mmol) in anhydrous pyridine (8 mL) and the reaction mixture was stirred for 30 min. To this cooled (~4° C.) reaction mixture was added 2-amidino-5-hydroxybenzofuran methanesulfonate, (from Example 3, 0.6 g, 2.20 mmol) in one portion, and the reaction mixture allowed to warm to room temperature with stirring for 16 h. The reaction mixture was triturated with $Et_2O$ (10 mL) and the $Et_2O$ layer was removed by decantation. This process was repeated twice and the residue was dissolved in methanol (10 mL). Saturated $NaHCO_3$ solution (20 mL) was added and the precipitated material was collected by filtration, washed with water (2×10 mL) and then dried in vacuo over $P_2O_5$ for 1 h to give 0.42 g of the desired material as a carbonate. The carbonate (0.42 g) was suspended in 5 mL of ethanol and then treated with methanesulfonic acid (0.25 g, 2.60 mmol). The reaction mixture was warmed gently for 2 min, sonicated for 2 min, and the precipitated solid was collected to give 0.34 g (40%) of title compound. Recrystallization from ethanol afforded an analytical sample as a tan solid, mp 260–262° C.

| Analysis: | Calc for $C_{14}H_{10}N_2O_3S$. $CH_3SO_3H$: | C, 47.11; H, 3.69; N, 7.33 |
|---|---|---|
| | Found: | C, 46.97; H, 3.70; N, 7.34 |

EXAMPLE 7

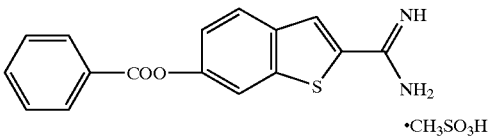

2-Amidino benzo[b]thien-6-yl benzoate methanesulfonate

A 2.5 M solution of n-BuLi (39.65 mL, 99.13 mmol) was added at −20° C. to a stirred solution of 14.8 g (90.12 mmol) of 6-methoxybenzo[b]thiophene (S. L. Grahm, et al. Topically Active Carbonic Anhydride Inhibitor. 2. Benzo[b] thiophenesulfonamide Derivatives with Ocular Hypotensive Activity. *J. Med. Chem.* 1989, 32 2548–2554) in 100 mL of anhydrous tetrahydrofuran with 5 mg of 2,2'-dipyridyl over 15 min. The resulting solution was stirred at −78° C. for 10 min and a tetrahydrofuran (100 mL) solution of $ZnI_2$ (31.63 g, 99.12 mmol) was added during 30 min. After warming up to 0° C. for 5 min and cooling back to −78° C. p-toluenesulfonyl cyanide (17.15 g, 94.64 mmol) in tetrahydrofuran (100 mL) was added over a period of 30 min, and the reaction mixture was warmed to room temperature and stirred for 16 h. The mixture was quenched with $NH_4Cl$ solution (300 mL) and then extracted with $Et_2O$ (3×250 mL). The combined $Et_2O$ layers were washed with $H_2O$, dried ($Na_2SO_4$) and evaporated in vacuo. The residue was purified by flash chromatography (silica-gel:450 g; hexane-EtOAc 95:5) to give 3.2 g (16%) of 6-methoxybenzo[b]thiophene-2-carbonitrile as a pink solid, mp 82–83° C. ($Et_2O$).

| Analysis: | Calc for $C_{10}H_7NOS$: | C, 63.47; H, 3.73; N, 7.40 |
|---|---|---|
| | Found: | C, 63.44; H, 3.78; N, 7.33 |

A mixture of 6-methoxybenzo[b]thiophene-2-carbonitrile (2.6 g, 13.74 mmol) and pyridinium chloride (12.5 g, 108.17 mmol) was heated at 190–200° C. for 1.5 h. The mixture was allowed to cool to room temperature and then triturated with cold water (30 mL). The precipitated solid was collected by filtration, washed with water (10 mL), and recrystallized from toluene to give 1.7 g (71%) of 6-hydroxybenzo[b]thiophene-2-carbonitrile as a brown solid, mp 195–198° C.

| Analysis: | Calc for $C_9H_5NOS$: | C, 61.70; H, 2.88; N, 7.99 |
|---|---|---|
| | Found: | C, 62.12; H, 3.12; N, 7.70 |

6-Hydroxybenzo[b]thiophene-2-carbonitrile (1.2 g, 6.85 mmol) was added to a cooled, saturated MeOH-HCl solution (15 mL) and the mixture was stirred for 24 h at ambient temperature. The reaction mixture was concentrated in vacuo to give a solid. The solid was suspended in anhydrous MeOH (60 mL) and gaseous NH$_3$ was introduced into the mixture at ambient temperature for 1 h and then at 50° C. for 20 h to give a homogeneous solution. The solvent was evaporated in vacuo and the resulting thick syrup was then treated with a saturated solution of NaHCO$_3$ (40 mL). The precipitate was collected by filtration, washed with water (2×10 mL), Et$_2$O (2×5 mL) and then dried in open air for 3 h to give the desired material as a carbonate. The carbonate (1.3 g) was suspended in 5 mL of methanol and then treated with methanesulfonic acid (0.94 g, 9.78 mmol). The precipitated material was recrystallized from MeOH to give 1.2 g (61%) of 2-amidino-6-hydroxybenzo[b]thiophene methanesulfonate as a yellow solid, mp 258–260° C.

| Analysis: | Calc C$_9$H$_8$N$_2$OS. CH$_3$SO$_3$H: | C, 41.66; H, 4.20; N, 9.72 |
|---|---|---|
| | Found: | C, 41.82; H, 4.16; N, 9.65 |

Benzoyl chloride (Aldrich, 0.31 g, 2.18 mmol) was added to a cooled, stirred suspension of 2-amidino-6-hydroxybenzo[b]thiophene methanesulfonate (0.6 g, 2.08 mmol) in dry pyridine (6 mL) and the reaction mixture was allowed to warm to ambient temperature with stirring for 16 h. The reaction mixture was triturated with Et$_2$O (10 mL) and the Et$_2$O layer was removed by decantation. This process was repeated. The residue was suspended in 2 mL of MeOH and saturated NaHCO$_3$ solution (20 mL) was added. The precipitated material was collected by filtration, washed with H$_2$O (2×5 mL) and Et$_2$O (2 mL) and then dried in vacuo over P$_2$O$_5$ for 2 h to give 0.5 g of the desired material as a carbonate. The carbonate (0.52 g) was suspended in 5 mL of MeOH and then treated with methanesulfonic acid (0.27 g, 2.81 mmol). The reaction mixture was warmed gently for 2 min, sonicated for 2 min, and the precipitated solid was recrystallized from MeOH to give 0.39 g (47%) of the title compound as a tan solid, mp 255–256° C.

| Analysis: | Calc for C$_{16}$H$_{12}$N$_2$O$_2$S. CH$_3$SO$_3$H: | C, 52.03; H, 4.11; N, 7.14 |
|---|---|---|
| | Found: | C, 51.99; H, 4.16; N, 7.12 |

EXAMPLE 8

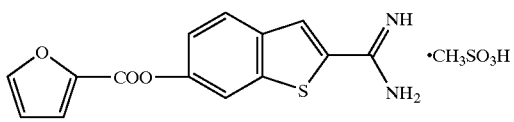

2-Amidino benzo[b]thien-6-yl 2-furancarboxylate methansulfonate

2-Furoyl chloride (Aldrich, 0.252 g, 1.93 mmol) was added to a cooled, stirred suspension of 2-amidino-6-hydroxybenzo[b]thiophene methanesulfonate, (from Example 7, 0.53 g, 1.84 mmol) in dry pyridine (6 mL) and the reaction mixture allowed to warm to ambient temperature with stirring for 16 h. The reaction mixture was triturated with Et$_2$O (20 mL) and the Et$_2$O layer was removed by decantation, This process was repeate to give a residue. The residue was triturated with saturated NaHCO$_3$ solution (20 mL) and the precipitated material was collected by filtration, washed with water (5 mL), Et$_2$O (5 mL) and then dried in vacuo over P$_2$O$_5$ for 1 h to give 0.44 g of the desired material as a carbonate. The carbonate (0.44 g) was suspended in 5 mL of methanol and then treated with methanesulfonic acid (0.62 g, 6.45 mmol). The reaction mixture was warmed gently for 2 min, sonicated for 2 min, and the precipitated solid was recrystallized from methanol to give 0.31 g (44%) of the title compound as a tan solid, mp 244–245° C.

| Analysis: | Calc for C$_{14}$H$_{10}$N$_2$O$_3$S. CH$_3$SO$_3$H: | C, 47.11; H, 3.69; N, 7.33 |
|---|---|---|
| | Found: | C, 46.98; H, 3.62; N, 7.28 |

EXAMPLE 9

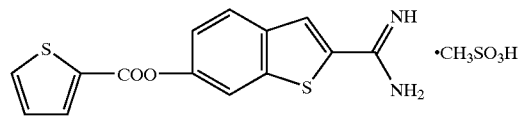

2-Amidino benzo[b]thien-6-yl 2-thiophenecarboxylate methanesulfonate

2-Thiophenecarbonyl chloride (Aldrich, 0.3 g, 2.04 mmol) was added to a cooled, stirred suspension of 2-amidino-6-hydroxybenzo[b]thiophene methanesulfonate (from Example 7, 0.56 g, 1.94 mmol) in dry pyridine (6 mL) and the reaction mixture allowed to warm to ambient temperature with stirring for 16 h. The reaction mixture was triturated with Et$_2$O (10 mL) and the Et$_2$O layer was removed by decantation. This process was repeated. The residue was triturated with saturated NaHCO$_3$ solution (15 mL) and the precipitated material was collected by filtration, washed with water (5 mL), Et$_2$O (5 mL) and then dried in vacuo over P$_2$O$_5$ for 1 h to give 0.46 g of the desired material as a carbonate. The carbonate (0.46 g) was suspended in 5 mL of methanol and then treated with methanesulfonic acid (0.26 g, 2.71 mmol). The reaction mixture was warmed gently for 2 min, sonicated for 2 min, and the precipitated solid was recrystallized from methanol to give 0.32 g (41%) of the title compound as an off-white solid, mp 248–250° C.

| Analysis: | Calc for C$_{14}$H$_{10}$N$_2$O$_2$S$_2$. CH$_3$SO$_3$H: | C, 45.21; H, 3.54; N, 7.03 |
|---|---|---|
| | Found: | C, 45.30; H, 3.59; N, 7.08 |

EXAMPLE 10

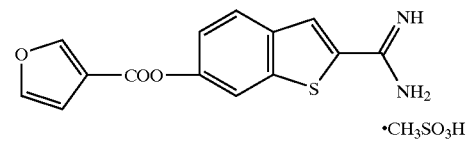

2-Amidino benzo[b]thien-6-yl 3-furancarboxylate methanesulfonate

3-Furancarbonyl chloride (Chou, C.; Trahanovsky. W. S. The [4+4] dimerization of 2,3-dimethyl-2,3-dihydrofuran: secondary deuterium kinetic isotope effect evidence for a two step mechanism. *J. Am. Chem. Soc.* 1986, 108, 4138–4144; 0.7 g, 2.43 mmol) in dry pyridine (7 mL) and the reaction mixture was allowed to warm to ambient temperature with stirring for 16 h. The reaction mixture was triturated with Et$_2$O (10 mL) and the Et$_2$O layer was removed by decantation. This process was repeated. The residue was triturated with a saturated NaHCO$_3$ solution (20 mL), and the precipitated material was collected by filtration, washed with H$_2$O (10 mL), Et$_2$O (5 mL) and then dried in vacuo over P$_2$O$_5$ for 1 h to give 0.51 g of the desired material as a carbonate. The carbonate (0.51 g) was suspended in 5 mL of MeOH and then treated with methanesulfonic acid (0.42 g, 4.37 mmol). The reaction mixture was warmed gently for 2 min, sonicated for 2 min, and the precipitated solid was recrystallized from MeOH to give 0.39 g (42%) of the title compound as a tan solid, mp 233–235° C.

| Analysis: | Calc for C$_{14}$H$_{10}$N$_2$O$_3$S. CH$_3$SO$_3$H: | C, 47.11; H, 3.69; H, 7.33 |
|---|---|---|
| | Found: | C, 47.02; H, 3.74; N, 7.32 |

EXAMPLE 11

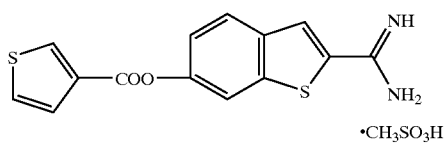

2-Amidino benzo[b]thien-6-yl 3-thiophenecarboxylate methanesulfonate

3-Thiophenecarbonyl chloride (Aldrich, 0.3 g, 2.04 mmol) was added to a cooled, stirred suspension of 2-amidino-6-hydroxybenzo[b]thiophene methanesulfonate, (from Example 7, 0.56 g, 1.94 mmol) in dry pyridine (6 mL) and the reaction mixture was allowed to warm to ambient temperature with stirring for 16 h. The reaction mixture was triturated with Et$_2$O (10 mL) and the Et$_2$O layer was removed by decantation. This process was repeated. The residue was suspended in 5 mL of MeOH, saturated NaHCO$_3$ solution (15 mL) was added and the precipitated material was collected by filtration, washed with H$_2$O (2×5 mL), Et$_2$O (2 mL) and then dried in vacuo over P$_2$O$_5$ for 2 h to give 0.52 g of the desired material as a carbonate. The carbonate (0.52 g) was suspended in 3 mL of MeOH and then treated with methanesulfonic acid (0.26 g, 2.71 mmol). The reaction mixture was warmed gently for 2 min, sonicated for 2 min, and the precipitated solid was recrystallized from MeOH to give 0.35 g (45%) of the title compound as a tan solid, mp 246–248° C.

| Analysis: | Calc for C$_{14}$H$_{10}$N$_2$O$_2$S$_2$. CH$_3$SO$_3$H: | C, 45.21; H, 3.54; H, 7.03 |
|---|---|---|
| | Found: | C, 45.09; H, 3.60; N, 6.97 |

EXAMPLE 12

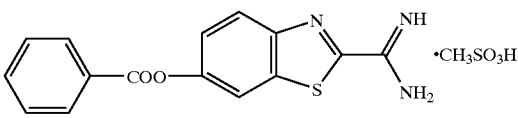

2-Amidino-6-benzothiazolyl benzoate methanesulfonate

2-Cyano-6-hydroxybenzothiazole, (White, E. H.; McCapra, F.; Field, G. F. The structures and synthesis of firefly luciferin. *J. Am. Chem. Soc.* 1963, 85, 337–342; 0.8 g, 4.54 mmol) was added to a cooled, saturated methanol-HCl solution (15 mL) and the mixture was stirred for 24 h at ambient temperature. The reaction mixture was concentrated in vacuo to give a solid. The solid was suspended in anhydrous methanol (40 mL) and gaseous NH$_3$ was introduced into the mixture at ambient temperature for 1 h and then at 50° C. for 2 h to give a homogenous solution. The solvent was evaporated in vacuo, and the resulting brown solid was suspended in methanol (15 mL) and then treated with a saturated solution of NaHCO$_3$ (50 mL). The precipitate was collected by filtration, washed with water (2×10 mL) and then dried in open air for 3 h. The solid (0.94 g) was suspended in 3 mL of methanol and then treated with methanesulfonic acid (0.45 g, 4.69 mmol). The precipitated material was recrystallized from methanol to give 0.75 g (57%) of 2-amidino-6-hydroxybenzothiazole methanesulfonate as a yellow solid, mp 276–278° C.

| Analysis: | Calc for C$_8$H$_7$N$_3$OS. CH$_3$SO$_3$H: | C, 37.36; H, 3.82; N, 14.52 |
|---|---|---|
| | Found: | C, 37.49; H, 3.86; N, 14.45 |

Benzoyl chloride (Aldrich, 0.39 g, 2.77 mmol) was added to a cooled, stirred suspension of 2-amidino-6-hydroxybenzothiazole methanesulfonate (0.8 g, 2.77 mmol) in dry pyridine (10 mL) and the reaction mixture allowed to warm to room temperature with stirring for 16 h. The reaction mixture was triturated with Et$_2$O (20 mL), and the Et$_2$O layer was removed by decantation. This process was repeated and the precipitated solid was collected by filtration. A solution of the precipitate in methanol (10 mL) was added to a saturated NaHCO$_3$ solution (50 mL), and water (20 mL) was added to precipitate a solid. The solid was collected by filtration, washed with water (15 mL) and then dried in vacuo over P$_2$O$_5$ for 2 h to give 0.29 g of the desired material as a carbonate. The carbonate was suspended in 2 mL of methanol and then treated with methanesulfonic acid (0.14 g, 1.46 mmol). The reaction mixture was warmed gently for 2 min, sonicated for 2 min, and the precipitated solid was collected to give 0.26 g (24%) of the title compound. Recrystallization from methanol afforded an analytical sample as a tan solid, mp 236–238° C.

| Analysis: | Calc for C$_{15}$H$_{11}$N$_3$O$_2$S. CH$_3$SO$_3$H: | C, 48.85; H, 3.84; N, 10.68 |
|---|---|---|
| | Found: | C, 48.74; H, 3.86; N, 10.58 |

EXAMPLE 13

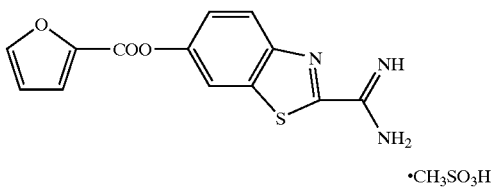

2-Amidino-6-benzothiazolyl 2-furancarboxylate methanesulfonate

2-Furoyl chloride (Aldrich, 0.293 g, 2.25 mmol) was added to a cooled, stirred suspension of 2-amidino-6-hydroxybenzothiazole methanesulfonate (from Example 12, 0.65 g, 2.25 mmol) in dry pyridine (7 mL) and the reaction mixture allowed to warm to room temperature with stirring for 16 h. The reaction mixture was triturated with $Et_2O$ (20 mL) and the precipitated solid was collected by filtration. A suspension of the precipitate in methanol (8 mL) was added to a saturated $NaHCO_3$ solution (30 mL), and water (20 mL) was added to precipitate a solid. The solid was collected by filtration, washed with water (15 mL) and then dried in vacuo over $P_2O_5$ for 3 h to give 0.65 g of the desired material as a carbonate. The carbonate was suspended in 3 mL of methanol and then treated with methanesulfonic acid (0.3 g, 3.12 mmol). The reaction mixture was warmed gently for 2 min, sonicated for 2 min, and the precipitated solid was collected to give 0.48 g (56%) of the title compound. Recrystallization from methanol afforded an analytical sample as an off-white solid, mp 232–234° C.

| Analysis: | Calc for $C_{13}H_9N_3O_3S$·$CH_3SO_3H$: | C, 43.86; H, 3.42; N, 10.96 |
|---|---|---|
| | Found: | C, 43.99; H, 3.45; N, 10.79 |

EXAMPLE 14

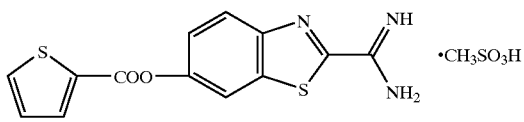

2-Amidino-6-benzothiazolyl 2-thiophenecarboxylate methanesulfonate

2-Thiophenecarbonyl chloride (Aldrich, 0.405 g, 2.77 mmol) was added to a cooled, stirred suspension of 2-amidino-6-hydroxybenzothiazole methanesulfonate (from Example 12, 0.8 g, 2.77 mmol) in dry pyridine (10 mL) and the reaction mixture allowed to warm to room temperature with stirring for 16 h. The reaction mixture was triturated with $Et_2O$ (20 mL) and the precipitated solid was collected by filtration. A suspension of the precipitate in methanol (8 mL) was added to a saturated $NaHCO_3$ solution (30 mL), and water (20 mL) was added to precipitate a solid. The solid was collected by filtration, washed with water (15 mL) and then dried in vacuo over $P_2O_5$ for 3 h to give 0.36 g of the desired material as a carbonate. The carbonate was suspended in 5 mL of methanol and then treated with methanesulfonic acid (0.4 g, 4.16 mmol). The reaction mixture was warmed gently for 2 min, sonicated for 2 min, and the precipitated solid was collected to give 0.31 g (28%) of the title compound. Recrystallization from methanol afforded an analytical sample as an off-white solid, mp 257–258° C.

| Analysis: | Calc for $C_{13}H_9N_3O_2S_2$·$CH_3SO_3H$: | C, 42.10; H, 3.28; N, 10.52 |
|---|---|---|
| | Found: | C, 42.08; H, 3.34; N, 10.38 |

EXAMPLE 15

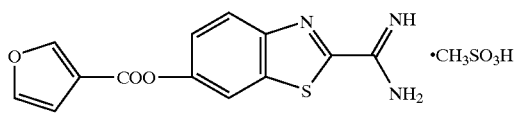

2-Amidino-6-benzothiazolyl 3-furancarboxylate methanesulfonate

3-Furoyl chloride (Chou, C.; Trahanovsky, W. S. The [4+4] dimerization of 2,3-dimethyl-2,3-dihydrofuran: secondary deuterium kinetic isotope effect evidence for a two-step mechanism. *J. Am. Chem. Soc.* 1986, 108, 4138–4144; 0.361 g, 2.77 mmol) was added to a cooled, stirred suspension of 2-amidino-6-hydroxybenzothiazole methanesulfonate (from Example 12, 0.8 g, 2.77 mmol) in dry pyridine (10 mL) and the reaction mixture allowed to warm to room temperature with stirring for 16 h. The reaction mixture was triturated with $Et_2O$ (20 mL), and the $Et_2O$ layer was removed by decantation. This process was repeated once more and the precipitated solid was collected by filtration. A suspension of the precipitate in methanol (10 mL) was added to a saturated $NaHCO_3$ solution (50 mL), and water (20 mL) was added to precipitate a solid. The solid was collected by filtration, washed with water (15 mL) and then dried in vacuo over $P_2O_5$ for 2 h to give 0.36 g of the desired material as a carbonate. The carbonate was suspended in 2 mL of methanol and then treated with methanesulfonic acid (0.3 g, 3.12 mmol). The reaction mixture was warmed gently for 2 min, sonicated for 2 min, and the precipitated solid was collected to give 0.36 g (34%) of the title compound. Recrystallization from methanol afforded an analytical sample as a brown solid, mp 235–236° C.

| Analysis: | Calc for $C_{13}H_9N_3O_3S$·$CH_3SO_3H$: | C, 43.86; H, 3.42; N, 10.96 |
|---|---|---|
| | Found: | C, 43.91; H, 3.46; N, 10.88 |

EXAMPLE 16

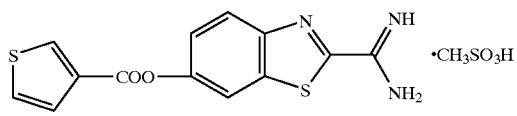

2-Amidino-6-benzothiazolyl 3-thiophenecarboxylate methanesulfonate

3-Thiophenecarbonyl chloride (Slocum, D. W.; Gierer, P. L. Directed Metalation reactions. 8. Directed Metalation of 3-Mono and 2,5-Disubstituted Thiophenes. *J Org. Chem.* 1976, 41, 3668–3673; 0.253 g, 1.73 mmol) was added to a cooled, stirred suspension of 2-amidino-6-hydroxybenzothiazole methanesulfonate (from Example 12, 0.5 g, 1.73 mmol) in dry pyridine (6 mL) and the reaction mixture allowed to warm to ambient temperature with stirring for 16 h. The reaction mixture was triturated with Et₂O (15 mL) and the Et₂O layer was removed by decantation. This process was repeated twice and the residue was dissolved in methanol (10 mL). Saturated NaHCO₃ solution (35 mL) was added and the precipitated material was collected by filtration, washed with water (2×10 mL) and then dried in vacuo over P₂O₅ for 1 h to give 0.26 g of the desired material as a carbonate. The carbonate (0.26 g) was suspended in 5 mL of methanol and then treated with methanesulfonic acid (0.2 g, 2.08 mmol). The reaction mixture was warmed gently for 2 min, sonicated for 2 min, and the precipitated solid was collected to give 0.27 g (52%) of the title compound as an off-white solid, mp 242–244° C. (methanol).

| Analysis: | Calc for C₁₃H₉N₃O₂S₂. CH₃SO₃H: | C, 42.10; H, 3.28; N, 10.52 |
|---|---|---|
| | Found: | C, 42.28; H, 3.33; N, 10.47 |

EXAMPLE 17

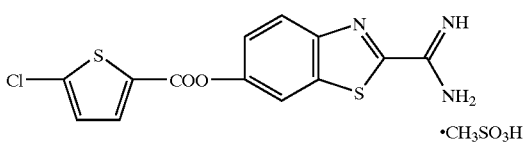

2-Amidino-6-benzothiazolyl 2-(5-chlorothiophene) carboxylate methanesulfonate 1-(3-Dimethylaminopropyl)-3-ethylcarbodiimide methiodide (Aldrich, 0.647 g, 2.18 mmol) was added to a cooled solution of 5-chlorothiophene-2-carboxylic acid (Aldrich, 0.354 g, 2.18 mmol) in dry pyridine (10 mL) and the reaction mixture was stirred for 30 min. To this cooled (~4° C.) reaction mixture was added 2-amidino-6-hydroxybenzothiazole methanesulfonate (from Example 12, 0.6 g, 2.07 mmol) in one portion, and the reaction mixture was allowed to warm to ambient temperature with stirring for 16 h. The reaction mixture was triturated with Et₂O (10 mL) and the Et₂O layer was removed by decantation. This process was repeated. The residue was suspended in 5 mL of MeOH, saturated NaHCO₃ solution (20 mL) was added and the precipitated material was collected by filtration, washed with H₂O (2×5 mL), Et₂O (2 mL) and then dried in vacuo over P₂O₅ for 2 h to give 0.29 g of the desired material as a carbonate. The carbonate (0.29 g) was suspended in 5 mL of MeOH and then treated with methanesulfonic acid (0.14 g, 1.45 mmol). The reaction mixture was warmed gently for 2 min, sonicated for 2 min, and the precipitated solid was recrystallized from MeOH to give 0.2 g (22%) of the title compound as a yellow solid, mp 247–248° C.

| Analysis: | Calc for C₁₃H₈ClN₃O₂S₂. CH₃SO₃H: | C, 38.74; H, 2.79; N, 9.68 |
|---|---|---|
| | Found: | C, 38.60; H, 2.87; N, 9.84 |

EXAMPLE 18

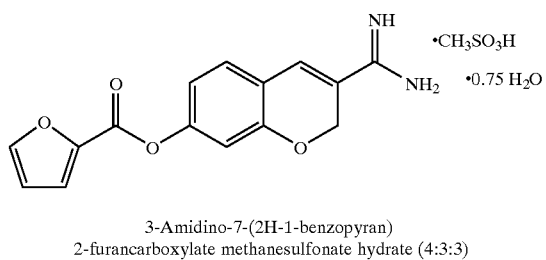

3-Amidino-7-(2H-1-benzopyran) 2-furancarboxylate methanesulfonate hydrate (4:3:3)

Imidazole (Aldrich, 14.8 g, 217 mmol) was added to a stirred solution of tert-butyldimethylsilylchloride (Aldrich, 32.8 g, 218 mmol) in dry CH₂Cl₂ (400 mL, distilled over P₂O₅ prior to use). After 5 min, 2,4-dihydroxybenzaldehyde (Aldrich, 20.0 g, 145 mmol) was added to the reaction mixture and stirred at 25° C. for 6 h. The reaction mixture was washed with H₂O (3×100 mL), brine (3×100 mL) and dried (Na₂SO₄). The solvent was removed in vacuo to yield a mixture of the desired product, 4-[(tert-butyldimethysilyl) oxy]-2-hydroxybenzadelhyde (Seidel, J. L.; Epstein, W. W.; Davidson, D. W. Neotropical ant gardens: chemical constituents. *J. Chem. Ecol.* 1990, 16, 1791–1816) contaminated with 2,4-[(di-tert-butyldimethylsilyl)oxyl] benzaldehyde (46.04 g) which was carried on to the next step without further purification.

A portion of the above mixture (30 g). was combined with 1,4-diazobicyclo[2.2.2]octane (Aldrich, 3.1 g, 27.7 mmol) and acrylonitrile (20 mL, 304 mmol) and heated at 80° C. for 4 h. The reaction mixture was concentrated in vacuo leaving an oily residue which was dissolved in a tetrahydrofuran/ ether mixture (1:1), washed with 10% NaHCO₃ (3×100 mL), dried (Na₂SO₄), and concentrated in vacuo to provide a crude mixture (36.1 g). The separated NaHCO₃ layer was extracted with EtOAc (3×50 mL). The combined EtOAc layers were dried (Na₂SO₄) and concentrated in vacuo to yield 3-cyano-7-hydroxy-2H-1-benzopyran (3.2 g) which was ~98% pure by ¹H NMR.

3-Cyano-7-hydroxy-2H-1-benzopyran (2.0 g, 11.5 mmol) was added to a cold, saturated solution of methanolic HCl (30 mL). This mixture was stirred at 25° C. for 48 h. The solvent was removed in vacuo leaving a solid which was dissolved in dry methanol (30 mL) and cooled in an ice bath. Ammonia (g) was bubbled into the cold solution for 1 h. This reaction mixture was removed from the ice bath and stirred at 25° C. for 24 h. The solvent was removed in vacuo to provide an orange solid which was converted to the carbonate by mixing with saturated NaHCO₃ (15 mL) and collecting the resulting solid by filtration. This solid was dried overnight and then converted to the methanesulfonate by combining the dry solid with methanol and adding methanesulfonic acid (1.8 g) dropwise. The resulting solid was filtered and dried to yield 3-amidino-7-hydroxy-2H-1-benzopyran methanesulfonate (1.46 g. 66%) as a yellow solid, mp 255–256° C. (ethanol).

| Analysis: | C₁₀H₁₀N₂O₂.CH₃SO₃H: | C, 46.15; H, 4.94; N, 9.78 |
|---|---|---|
| | Found: | C, 46.41; H, 4.96; N, 9.57 |

1-(3-Dimethylaminopropyl)-3-ethylcarbodiimide methiodide (Aldrich, 1.3 g, 4.37 mmol) was added to a cold solution of 2-furoic acid (Aldrich, 0.48 g, 4.28 mmol) in dry pyridine (10 mL). This mixture was stirred for 20 minutes and 3-amidino-7-hydroxy-2H-1-benzopyran methanesulfonate (1.2 g, 4.19 mmol) was added in one portion. This mixture was allowed to stir and warm to ambient temperature overnight. The solid that formed was triturated with ether (3×15 mL) and then converted to the carbonate by adding NaHCO$_3$ (15 mL) which yielded a yellow solid. This solid was dried overnight, dissolved in methanol (6 mL), and converted to the methanesulfonate by adding methanesulfonic acid (0.8 g) dropwise to yield the title compound as a yellow solid, 1.04 g (65%), mp 254–255° C.

| Analysis: | $C_{15}H_{12}N_2O_4 \cdot CH_3SO_3H$ 0.75 $H_2O$: | C, 48.81; H, 4.44; N, 7.11 |
|---|---|---|
| | Found: | C, 48.79; H, 4.23; N, 6.95 |

EXAMPLE 19

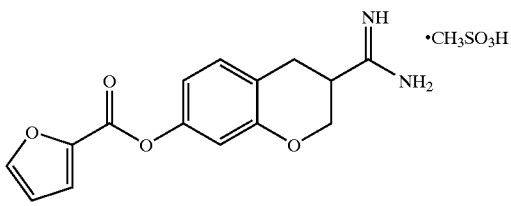

3-Amidino-7-(3,4-dihydro-1-benzopyran) 2-furancarboxylate methanesulfonate

A sample of 3-amidino-7-(2H-1-benzopyran) 2-furancarboxylate methanesulfonate (Example 18, 0.25 g, 0.657 mmol) was combined with dry dimethylformamide (6.0 mL) and 10% Pd/C (0.05 g) in a Parr pressure bottle and hydrogenated at 40 psi for 7 h. The reaction mixture was filtered through Celite® to remove the catalyst and the cake washed with MeOH (25 mL). The filtrate was concentrated in vacuo to yield a yellow solid which was triturated with EtOH to yield 0.15 g (58%) of the title compound as a tan solid, mp 220–222° C.

| Analysis: | Calc for $C_{15}H_{14}N_2O_4 \cdot$ $CH_3SO_3H$: | C, 50.26; H, 4.75; N, 7.32 |
|---|---|---|
| | Found: | C, 46.41; H, 4.40; N, 6.71 |

EXAMPLE 20

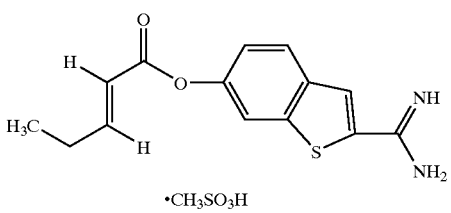

trans-2-Amidino-6-benzo[b]thienyl 2-Pentenoate methanesulfonate 1-(3-Dimethylaminopropyl)-3-ethylcarbodiimide methiodide (0.68 g, 2.29 mmol) was added to a cooled solution of trans-2-pentenoic (0.229 g, 2.29 mmol) in dry pyridine (6 mL) and the reaction mixture was stirred for 30 min. To this cooled (~4° C.) reaction mixture was added 2-amidino-6-hydroxybenzo[b]thiophene methanesulfonate (0.6 g, 2.08 mmol) in one portion and the reaction mixture was allowed to warm to room temperature with stirring for 16 h. The reaction mixture was triturated with Et$_2$O) (10 mL) and the Et$_2$O layer was removed by decantation. This process was repeated once more to get a residue. The residue was triturated with saturated NaHCO$_3$ solution (20 mL) and the precipitated material was collected by filtration, washed with H$_2$O (10 mL), Et$_2$O (5 mL) and then dried in vacuo over P$_2$O$_5$ for 1 h to give 0.45 g of the desired material as a carbonate. The carbonate (0.41 g) was suspended in 5 mL of MeOH and then treated with methanesulfonic acid (0.26 g, 2.71 mmol). The reaction mixture was warmed gently for 2 min, sonicated for 2 min, and the precipitated solid was recrystallized from MeOH to give 0.1 g (13%) of BCX-1588 as a light-yellow solid, mp 220–222° C.

BIOCHEMICAL DATA

Purification of Factor D

A modification of the procedure of Volanakis (Volankis, J. E.; Barnum, S. R.; Kilpatrick, J. M. Purification and properties of human factor D. *Methods in Enzymol.* 1993, 223, 82–97) for purification of Factor D was utilized as described by Yamauchi (Yamauchi, Y.; Stevens, J. W.; Macon, K. J.; Volanakis, J. E. Recombinant and native zymogen forms of human complement factor D. *J. Immunol.* 1994, 152, 3645–3653. Briefly, Factor D was purified from the urine of a patient with Fanconi syndrome by ion exchange chromatography using BioRex 70 and two rounds of ion-exchange chromatography in a Pharmacia FPLC system using a HR5/5 Mono S column.

Inhibition Assays

The compounds to be tested were dissolved in a stock solution of DMSO at 10.0 or 100 mM. A portion of this stock solution was added to assay buffer in a final volume of 100 μL containing the enzyme of interest. Controls included buffer alone and enzyme solutions to which DMSO was added. Substrate was added to the reaction wells immediately or after incubation at room temperature. The reaction rates were measured spectrophotometrically by the generation of product at 405 nm for 200 sec. Background absorbance at 690 nm was measured and subtracted from the absorbance at 405 nm for each well.

The reaction rate for enzyme alone was compared to the rate of enzyme in the presence of inhibitor and the percent inhibition was calculated as shown below:

Percent Inhibition=[Rate without inhibitor−Rate with inhibitor)/ (Rate without inhibitor)]×100

An IC$_{50}$, a compound concentration which inhibits 50% of the enzymatic activity, was calculated. Compounds in the examples were tested a minimum of three times.

Esterolytic Assays

1. Factor D

An established esterolytic assay for the measurement of Factor D activity and inhibition of Factor D activity was used (Kam, C. M.; McRae, B. J.; Harper, J. W.; Niemann, M. A.; Volanakis, J. E.; Powers, J. C. Human complement proteins D, C2, and B Active site mapping with peptide thioester substrates. *J Biol. Chem.* 1987, 262, 3444–3451). For this assay Z-Lys-SBzl, 1.29 mM (Kim, S.; Narayana, S. V. L; Volanakis, J. E. Mutational analysis of the substrate binding site of human complement Factor D. *Biochemistry.* 1994, 33, 14393–14399.) was used as the substrate for Factor D (104 mM). Hydrolysis of this compound by Factor D liberated a free sulfhydryl group which is then reacted with 5,5'-dithiobis(2nitrobenzoic acid) producing an intense yellow color (Habeeb, A. F. S. A. Reaction of protein sulfhydryl groups with Ellman's Reagent. *Methods in Enzymol.* 1976, 25, 457–464.). The assays were performed in 96 well microtiter plates and rates of hydrolysis were monitored at 405 nm in a Anthos Labtec HT2 plate reader. Hydrolysis rates were reported as change in mOD/min. The assay was conducted in 100 mM HEPES, 500 mM NaCl, pH 7.5 containing 10% DMSO in a final volume of 200 µL per well.

2. C1s

C1s esterolytic activity was assayed using a modification of the technique originally described by Kam using Z-Lys-SBzl, 1.29 mM as substrate and C1s at 3 to 13 nM.

3. Thrombin, Factor Xa, Plasmin, Factor XIIa and Kallikrein

Thrombin was assayed at 12.5 U/ml using 0.37 mM N-Benzoyl-Phe-Val-Arg-p-nitroanilide (Svendsen, L.; Blomback B.; Blomback, M.; Olsson, P. I. Substrate for determination of trypsin, thrombin and thrombin-like enzymes. *Folia Haematol.* 1972, 98, 446–454.) as the substrate in 100 mM HEPES, 10 mM $CaCl_2$, 10% DMSO, pH 7.5. Factor Xa, 0.5 U/mL, was assayed in 50 mM HEPES, 150 mM NaCl, 10 mM $CaCl_2$, pH 8.0 using Chromozyme X, 0.17 mM, as the substrate. Plasmin (0.004 units/mL), factor XIIa (30–60 mM) and kallikrein (0.02 units/mL were assayed using modifications of the techniques originally described by McRae, et al. (*Biochemistry*. 1981, 20, 7196–7206). The assays were run in 200 mM triethanolamine, pH 7.8 and 100 mM Tris-HCl, 100 mM EDTA, pH 3.5 using Z-Lys-SBzl, 0.13 mM and 2-Gly-Arg-SBzl, 0.16 mM, as substrates, respectively.

TABLE 6

Serine Protease Inhibitory Data

LCORCNH₂

Esterolytic and Amidolytic Assays
($IC_{50}$, nM)

| Example | L | R | Factor D | C1s | Thrombin | Xa | Kallikrein | XIIa | Plasmin |
|---|---|---|---|---|---|---|---|---|---|
| reference | nafamostat | | 11000 | 22 | 678 | 1010 | 12 | 114 | 50 |
| reference | 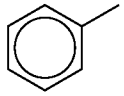 |  | 4000 | 40 | 3110 | 7170 | | | |
| 1 | 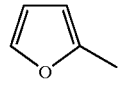 | 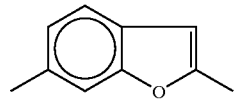 | 3650 | 37 | 57 | 60 | 5.4 | 20 | 42 |
| 2 | 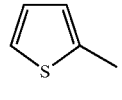 | 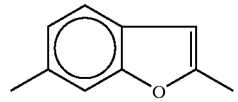 | 9110 | 519 | 520 | 996 | | | 817 |
| 3 | 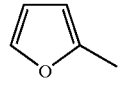 | 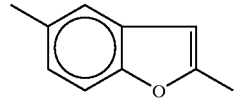 | 460 | 56 | 65 | 4.0 | 5.4 | 20.2 | 23 |
| 4 | 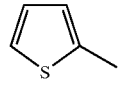 | 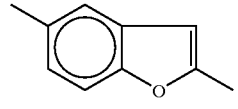 | 5590 | 50 | 124 | 880 | | | 116 |
| 5 | 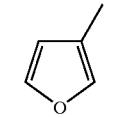 | 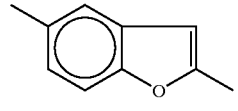 | 2850 | 76 | 104 | 1580 | | | 325 |
| 6 | 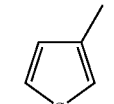 | 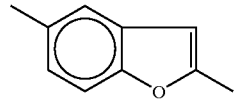 | 10800 | 122 | 361 | 500 | | | 546 |
| 7 | 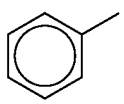 | 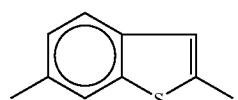 | 500 | 11 | 39 | 23 | 1.3 | 901 | 11 |

TABLE 6-continued

Serine Protease Inhibitory Data

LCORCNH₂

Esterolytic and Amidolytic Assays
($IC_{50}$, nM)

| Example | L | R | Factor D | C1s | Thrombin | Xa | Kallikrein | XIIa | Plasmin |
|---|---|---|---|---|---|---|---|---|---|
| 8 | 2-furyl | methylbenzothiophene | 147 | 1.7 | 44 | 1.0 | 1.4 | 5.4 | 1.0 |
| 9 | 2-thienyl | methylbenzothiophene | 96 | 1.6 | 42 | 3.2 | 1.4 | 6.0 | 4.1 |
| 10 | 3-furyl | methylbenzothiophene | 177 | 4.1 | 47 | 1 | 1.6 | 17.4 | 1 |
| 11 | 3-thienyl | methylbenzothiophene | 175 | 4.3 | 39 | 6 | 1.6 | 12.7 | 9 |
| 12 | phenyl | methylbenzothiazole | 564 | 5.3 | 44 | 52 | 3.8 | 13 | 37 |
| 13 | 2-furyl | methylbenzothiazole | 421 | 3 | 25 | 1 | 4 | 9 | 2 |
| 14 | 2-thienyl | methylbenzothiazole | 250 | 2 | 18 | 12 | 2 | 5 | 6 |
| 15 | 3-furyl | methylbenzothiazole | 286 | 2 | 15 | 22 | 5 | 6 | 15 |
| 16 | 3-thienyl | methylbenzothiazole | 205 | 2.5 | 42 | 31 | 2.6 | 10 | 21 |
| 17 | 5-chloro-2-thienyl | methylbenzothiazole | 260 | 2 | 48 | 2 |  |  | 3 |
| 18 | 2-furyl | methylchromene | 347 | 2.9 | 51 | 3.9 | 3.6 | 6.1 | 1.5 |

TABLE 6-continued

Serine Protease Inhibitory Data $$\underset{\text{LCORCNH}_2}{\overset{\text{O NH}}{\|\ \|}}$$

Esterolytic and Amidolytic Assays
($IC_{50}$, nM)

| Example | L | R | Factor D | C1s | Thrombin | Xa | Kallikrein | XIIa | Plasmin |
|---|---|---|---|---|---|---|---|---|---|
| 19 | | | 50,000 | 750 | | | 661 | | |
| 20 | | | 190 | 6 | 47 | 5 | 12 | 27 | 6 |

A broad spectrum serine protease inhibitor is considered useful in certain procedures such as cardiopulmonary bypass surgery (Sundaram, S. et al. *Thrombosis and Hemostasis* 75: 76–82, 1996). For example, nafamostat (6'-amidino-2-naphthyl-p-guanidinobenzoate) has inhibitory activity on thrombin, plasma kallikrein, plasmin, and complement factor C1s. The compound has anti-fibrinolytic and anticoagulant activity. Nafomostat, however, is a relatively weak inhibitor of the alternate pathway enzymes Factor B ($IC_{50}$ = 60 μM. Ikari, N. et al. *Immunology* 49: 685–691, 1983) and Factor D ($IC_{50}$=25 μm, Inagi, R et al, *Nephron* 66: 285–290, 1994). Nafomostat clearly reduces post-operative bleeding by means of its inhibition of plasmin and kallikrein, but may have little benefit in suppressing complement activation during procedures such as cardiopulmonary bypass (Sundaram, S. et al, *Thrombosis and Hemostasis* 75: 76–82, 1996). Broad spectrum serine protease inhibitors with more potent inhibitory actions on complement enzymes such as Factor D and C1s are expected to have significant anti-inflammatory utility in surgical procedures where blood is exposed to foreign surfaces, or where tissue is exposed to vascular occlusion and reperfusion. Indeed, nafamostat may have some moderate beneficial effect on myocardial reperfusion inflammatory injury during cardiopulmonary bypass (Sawa, Y. et al, *J Thor Cardiovasc. Surg.* 111: 29–35, 1996).

From the results presented in the above table of data, it can be seen that the compounds of the present invention have markedly superior potency on Factor D and C1s compared to the reference compounds. In particular, examples 6–10 are more than one order of magnitude more potent on Factor D and C1s than nafamostat while retaining high potency on factor Xa, factor XIIa, plasmin and kallikrein.

Thus, the compounds of the present invention are expected to have improved anti-inflammatory as well as anticoagulant and anti-fibrinolytic activity in surgical procedures such as cardiopulmonary bypass and organ transplant rejection where blood is exposed to foreign surfaces. In addition, because the compounds of the present invention are potent inhibitors of enzymes in both the classical and alternate pathways, they will be useful in the treatment of numerous complement mediated disorders, including but not limited to, reperfusion injury, glomerulonephritis, lupus erythematosus, rheumatoid arthritis, multiple sclerosis, myesthenia gravis, Alzheimer's disease, adult respiratory distress syndrome, anaphylaxis, and inflammatory bowel disease.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. Compound formula (I) or (II):

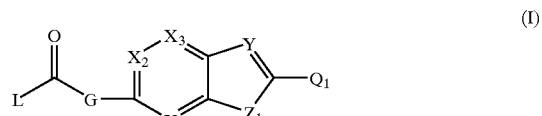
(I)

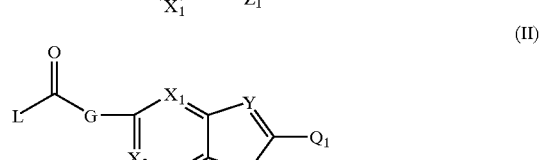
(II)

wherein

G is O or

L is selected from the group consisting of the group $L_1$ consisting of

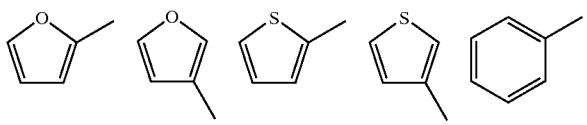

and each member of said group can have 0, 1, 2 or 3 pendant groups selected from the group $J_1$; wherein each $J_1$ is individually selected from the group consisting of
H, halogen
$CF_3$
alkyl groups, straight or branched chain, of 1–5 carbon atoms,
alkoxy groups having 1–5 carbon atoms,
aryl, and
heterocyclic;
$Q_1$ is, $C(=NH)NH_2$;
$X_1$, $X_2$ and $X_3$ are each C;
Y is $C(J_2)$;
$Z_1$ is O or S;
each $J_2$ is individually selected from the group consisting of
H, halogen,
$CF_3$, and
lower alkyl, straight or branched chain, of 1–5 carbon atoms;
each $J_3$ is individually selected from the group consisting of
H, and
lower alkyl, straight or branched, of 1–5 carbon atoms; and pharmaceutically acceptable salts thereof.

2. The compound of claim 1 wherein $Q_1$ is $C(=NH)NH_2$.

3. The compound of claim 1 being selected from the group consisting of:
2-amidino-5 or 6-benzofuranyl 2-furanyl carboxylate,
2-amidino-5 or 6-benzofuranyl 2-thiophene carboxylate,
2-amidino-5-benzofuranyl 3-furanyl carboxylate,
2-amidino-6-benzothiazolyl 2- or 3-furanyl carboxylate,
2-amidino-6-benzothiazolyl 2-thiophene carboxylate,
2-amidino-6-benzothiazolyl benzoate,
2-amidino-5-benzofuranyl 3-thiophene carboxylate,
2-amidino-benzo[b]thien-6-yl benzoate,
2-amidino-benzo[b]thien-6-yl 2-furancarboxylate,
2-amidino-benzo[b]thien-6-yl 3-thiophenecarboxylate,
2-amidino-benzo[b]thien-6-yl 3-furancarboxylate,
2-amidino-benzo[b]thien-6-yl 3-thiophenecarboxylate,
2-amidino-6-benzothiazolyl 3-thiophenecarboxylate,
2-amidino-6-benzothiazolyl 2-(5-chlorothiophene carboxylate,
3-amidino-7-(3-furancarboxy)-2H-1-benzopyran,
3-amidino-7-(2-thiophenecarboxy)-2H-1-benzopyran,
3-amidino-7-(3-thiophenecarboxy)-2H-1-benzopyran,
trans-2-amidino-6-benzo[b]thienyl 2-pentenoate, or pharmaceutically acceptable salts thereof.

4. The compound of claim 1 being 2-amidino-5- or 6-benzofuranyl 2-furanyl carboxylate or a pharmaceutically acceptable acid condition salt thereof.

5. The compound of claim 1 being 2-amidino-5 or 6-benzofuranyl 2-thiophene-carboxylate or a pharmaceutically acceptable salt thereof.

6. The compound of claim 1 being 2-amidino-5-benzofuranyl 3-furanylcarboxylate or a pharmaceutically acceptable salt thereof.

7. The compound of claim 1 being 2-amidino-6-benzothiazolyl 2- or 3-furancarboxylate or a pharmaceutically acceptable salt thereof.

8. The compound of claim 1 being 2-amidino-6-benzothiazolyl 2-thiophenecarboxylate or a pharmaceutically acceptable salt thereof.

9. The compound of claim 1 being 2-amidino-6-benzothiazolyl benzoate or a pharmaceutically acceptable salt thereof.

10. The compound of claim 1 being 2-Amidino-5-benzofuranyl 3-thiophenecarboxylate methanesulfonate.

11. The compound claim 1 being 2-Amidino benzo[b]thien-6-yl benzoate methanesulfonate.

12. The compound of claim 1 being 2-Amidino benzo[b]thien-6-yl 2-furancarboxylate methanesulfonate.

13. The compound of claim 1 being 2-Amidino benzo[b]thien-6-yl 2-thiophenecarboxylate methanesulfonate.

14. The compound of claim 1 being 2-Amidino benzo[b]thien-6-yl 3-furancarboxylate methanesulfonate.

15. The compound of claim 1 being 2-Amidino benzo[b]thien-6-yl 3-thiophenecarboxylate methanesulfonate.

16. The compound of claim 1 being 2-Amidino-6-benzothiazolyl 3-thiophenecarboxylate methanesulfonate.

17. The compound of claim 1 being 2-Amidino-6-benzothiazolyl 2-(5-chlorothiophene)carboxylate methanesulfonate.

18. A pharmaceutically composition for use in the complement, coagulation and kallikrein pathways comprising a compound according to claim 1 or pharmaceutically acceptable addition salt thereof that inhibits a broad spectrum of serine proteases; and a pharmaceutical carrier.

19. A pharmaceutically composition for the induction of "blood anesthesia" comprising a compound according to claim 1 or pharmaceutically acceptable addition salt thereof that acts at multiple sites of the coargulation and complement components; and a pharmaceutical carriers.

* * * * *